(12) United States Patent
Califano et al.

(10) Patent No.: US 10,777,299 B2
(45) Date of Patent: Sep. 15, 2020

(54) SYSTEMS AND METHODS FOR MATCHING ONCOLOGY SIGNATURES

(71) Applicant: THE TRUSTEES OF COLUMBIA UNIVERSITY IN THE CITY OF NEW YORK, New York, NY (US)

(72) Inventors: Andrea Califano, New York, NY (US); Mariano Javier Alvarez, Cortlandt Manor, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 15/249,069

(22) Filed: Aug. 26, 2016

(65) Prior Publication Data

US 2017/0056530 A1 Mar. 2, 2017

Related U.S. Application Data

(60) Provisional application No. 62/211,562, filed on Aug. 28, 2015, provisional application No. 62/253,342, filed on Nov. 10, 2015.

(51) Int. Cl.
*G16B 5/00* (2019.01)
*G01N 33/574* (2006.01)
*G01N 33/68* (2006.01)

(52) U.S. Cl.
CPC ......... *G16B 5/00* (2019.02); *G01N 33/57484* (2013.01); *G01N 33/68* (2013.01); *G01N 2500/20* (2013.01)

(58) Field of Classification Search
None
See application file for complete search history.

(56) References Cited

U.S. PATENT DOCUMENTS

| | | | |
|---|---|---|---|
| 2004/0209942 A1 | 10/2004 | Li | |
| 2009/0163564 A1* | 6/2009 | Borden | A61K 31/4196 514/383 |
| 2011/0172929 A1 | 7/2011 | Califano | |
| 2013/0144887 A1 | 6/2013 | Chen et al. | |
| 2013/0156795 A1 | 6/2013 | Iavarone et al. | |
| 2014/0199692 A1* | 7/2014 | Jamieson, Jr. | A61K 31/4196 435/6.11 |
| 2015/0213115 A1 | 7/2015 | Mukherjee et al. | |

FOREIGN PATENT DOCUMENTS

| WO | WO 2000/054046 A2 | 9/2000 |
|---|---|---|
| WO | WO 2009/092024 A1 | 7/2009 |
| WO | WO 2015/127101 A1 | 8/2015 |
| WO | WO 2015/127104 A1 | 8/2015 |

OTHER PUBLICATIONS

Bild et al. Nature 439, 353-357,2006.*
Lefebvre et al. Molecular Systems Biology 6:377, 1-10.*
Margolin et al. BMC Bioinformatics 2006, 7(Suppl 1):S7, p. 1-15.*
Zhang et al. Science, vol. 276, pp. 1268-1272, 1997.*
Ajani et al. Seminars in Oncology, 2005, vol. 32, No. 6 Suppl 8, p. 2-4.*
Zhang et al. PLoS One (2013), 8(11), e79444/1-e79444/9.*
Bansal et al. PLoS One (2011), 6(10), e26156.*
Alvarez et al., "Correlating measurements across samples improves accuracyof large-scale expression profile experiments," Genome Biol. 10:R143 (2009).
Alvarez et al., "Functional characterization of somatic mutations in cancer using network-based inference of protein activity," Nature Genetics, 48(8):838-847 (2016).
Alvarez et al., "Using viper, a package for Virtual Inference of Protein-activity by Enriched Regulon analysis," Bioconductor Website, pp. 1-15 (Oct. 17, 2016).
Aytes et al., "Cross-Species Regulatory Network Analysis Identifies a Synergistic Interaction between FOXM1 and CENPF that Drives Prostate Cancer Malignancy," Cancer Cell 25:638-651 (2014).
Bansal et al., "A community computational challenge to predict the activity of pairs of compounds," Nat. Biotechnol. 32(12):1213-1222 (2014).
Borelli et al., "Gene regulatory networks inference using a multi-GPU exhaustive search algorithm," BMC Bioinformatics 14(Suppl. 18): S5 (2013).
Bozdag et al., "Master Regulators, Regulatory Networks, and Pathways of Glioblastoma Subtypes," Cancer Informatics 13(S3):33-44 (2014).
Califano, "National Center: Multiscale Analysis of Genomic and Cellular Networks (Magnet)," NIH Grant #:5U54CA121852-08, U.S. Dept. of Health and Human Services, NIH Research Portfolio Online Reporting Tools (Accessed on Feb. 8, 2017).
Califano, "Systems Biology of Tumor Progression and Drug Resistance," NIH Grant #: 1U01CA168426-01, U.S. Dept. of Health and Human Services, NIH Research Portfolio Online Reporting Tools (Accessed on Feb. 8, 2017).
Carro et al., "The transcriptional network for mesenchymal transformation of brain tumours," Nature 463:318-325 (2010).
Chen et al., "Identification of Causal Genetic Drivers of Human Disease through Systems-Level Analysis of Regulatory Networks," Cell 159:402-414 (2014).

(Continued)

*Primary Examiner* — Michael L Borin
(74) *Attorney, Agent, or Firm* — Barry L. Davison; Davis Wright Tremaine LLP

(57) ABSTRACT

Techniques to profile a disease or a disorder (e.g., a tumor) based on a protein activity signature are disclosed herein. An example method can include measuring quantitatively protein activity of a plurality of master regulator proteins in a sample from a disease or disorder; and profiling the tumor from the quantitative protein activity of the master regulator proteins. Also disclosed are methods of identifying a compound or compounds that treats diseases or disorders (e.g., inhibit tumor cell growth).

12 Claims, 43 Drawing Sheets
(40 of 43 Drawing Sheet(s) Filed in Color)

(56) References Cited

OTHER PUBLICATIONS

Della Gatta et al., "Reverse engineering of TLX oncogenic transcriptional networks identifies RUNX1 as tumor suppressor in T-ALL," Nat. Med. 18(3):436-440 (2012).
Hajingabo et al., "Predicting interactome network perturbations in human cancer: application to gene fusions in acute lymphoblastic leukemia," Mol Biol Cell 25:3973-3985 (Dec 2014).
Hanahan, D. & Weinberg, R. a. Hallmarks of cancer: The next generation. Cell 144, 646-674 (2011).
Hu, "An efficient algorithm to identify coordinately activated transcription factors," Genomics 95(3):143-150 (2010).
Ikiz et al., "The Regulatory Machinery of Neurodegeneration in In Vitro Models of Amyotrophic Lateral Sclerosis," Cell Reports 12:335-345 (2015).
International Search Report and Written Opinion dated Nov. 23, 2016 in International Application No. PCT/US2016/049070.
International Search Report and Written Opinion dated Nov. 23, 2016 in International Application No. PCT/US2016/049063.
Keith et al., "Multicomponent therapeutics for networked systems," Nat. Rev. Drug Discov. 4:71-78 (2005).
Lefebvre et al. "A human B-cell interactome identifies MYB and FOXM1 as master regulators of proliferation in germinal centers," Mol. Syst. Biol. 6:377 (2010).
Margolin et al., "ARACNE: an algorithm for the reconstruction of gene regulatory networks in a mammalian cellular context," BMC Bioinformatics 7(Suppl. 1):S7 (2006).
Palomero et al., "NOTCH1 directly regulates c-MYC and activates a feed-forward-loop transcriptional network promoting leukemic cell growth," PNAS 103(48):18261-18266 (2006).
Phillips et al., "Molecular subclasses of high-grade glioma predict prognosis, delineate a pattern of disease progression, and resemble stages in neurogenesis," Cancer Cell 9:157-173 (2006).
Piovan et al., "Direct Reversal of Glucocorticoid Resistance by AKT Inhibition in Acute Lymphoblastic Leukemia," Cancer Cell 24:766-776 (2013).
Prat et al. "Phenotypic and molecular characterization of the claudin-low intrinsic subtype of breast cancer," Breast Cancer Res. 12:R68 (2010).
Vaske et al., "Inference of patient-specific pathway activities from multi-dimensional cancer genomics data using PARADIGM," Bioinformatics 26(12):i237-i245 (2010).
Weinstein, I. B. Cancer. Addiction to oncogenes—the Achilles heal of cancer. Science 297, 63-4 (2002).
Zhang et al., "Network motif-based identification of transcription factor-target gene relationships by integrating multi-source biological data," BMC Bioinformatics 9:203 (2008).

Affara, M., et al., "Vasohibin-1 is Identified as a Master-Regulator of Endothelial Cell Apoptosis Using Gene Network Analysis," BMC Genomics 14(23):1-12, 2013.
Alvarez, M.J., et al., "Using Viper, a Package for Virtual Inference of Protein-Activity by Enriched Regulon Analysis," <https://static1.squarespace.com/static/5697c2e5e0327ca6778bc453/t/56f40934f8baf3727f8e7e78/1458833718573/Viper.pdf> [retrieved Feb. 8, 2019], Jul. 22, 2013, pp. 1-14.
Alvarez, M.J., et al., "Using Viper, a Package for Virtual Inference of Protein-Activity by Enriched Regulon Analysis," <http://citeseerx.ist.psu.edu/viewdoc/download;jsessionid=A046487756888564E244A5E5AB118F22?doi=10.1.1.671.7432&rep=rep1&type=pdf> [retrieved Feb. 11, 2019], Oct. 13, 2014, pp. 1-14.
Baca-López, K., et al., "The Role of Master Regulators in the Metabolic/Transcriptional Coupling in Breast Carcinomas," Plos One 7(8)(e42678):1-17, Aug. 2012.
Fletcher, M.n. C., et al., "Master Regulators of FGFR2 Signalling and Breast Cancer Risk," Nature Communications 4(1):1-12, Sep. 17, 2013.
Giorgi, F.M., et al., "Inferring Protein Modulation From Gene Expression Data Using Conditional Mutual Information," PLOS One 9(10)(e109569):1-9, Oct. 2014.
Paull, E., et al., "Master Regulator and Network Diffusion Analysis Reveals Convergent Cancer Driver Programs Across Pan-Cancer Samples," The Cancer Genome Atlas 4th Annual Scientific Symposium May 11-12, 2015, <http://www.capconcorp.com/meeting/2015/TCGASymposium/TCGA-Abstracts_(050815).pdf> [retrieved Feb. 11, 2019], p. 81.
Woo, J.H., et al., "Elucidating Compound Mechanism of Action by Network Perturbation Analysis," Cell 162(2):441-451, Jul. 16, 2015.
Partial European Search Report dated Feb. 15, 2019, issued in European Patent Application No. 16842698.9, filed Aug. 26, 2016, 6 pages.
Extended European Search Report dated Feb. 21, 2019, issued in European Patent Application No. 16842702.9, filed Aug. 26, 2016, 3 pages.
Niola, F., et al., "Mesenchymal High-Grade Glioma is Maintained by the ID-RAP1 Axis," The Journal of Clinical Investigation 123(1):405-417, Dec. 17, 2012.
Supplemental European Search Report dated May 14, 2019, issued in European Patent Application No. 16842698.9, filed Aug. 26, 2016, 13 pages.
Subramanian, A., et al., "Gene Set Enrichment Analysis: A Knowledge-Based Approach for Interpreting Genome-Wide Expression Profiles," Proceedings of the National Academy of Sciences of the United States of America 102(43):15545-15550, Oct. 25, 2005.
U.S. Appl. No. 15/248,975, filed Aug. 26, 2016.

* cited by examiner

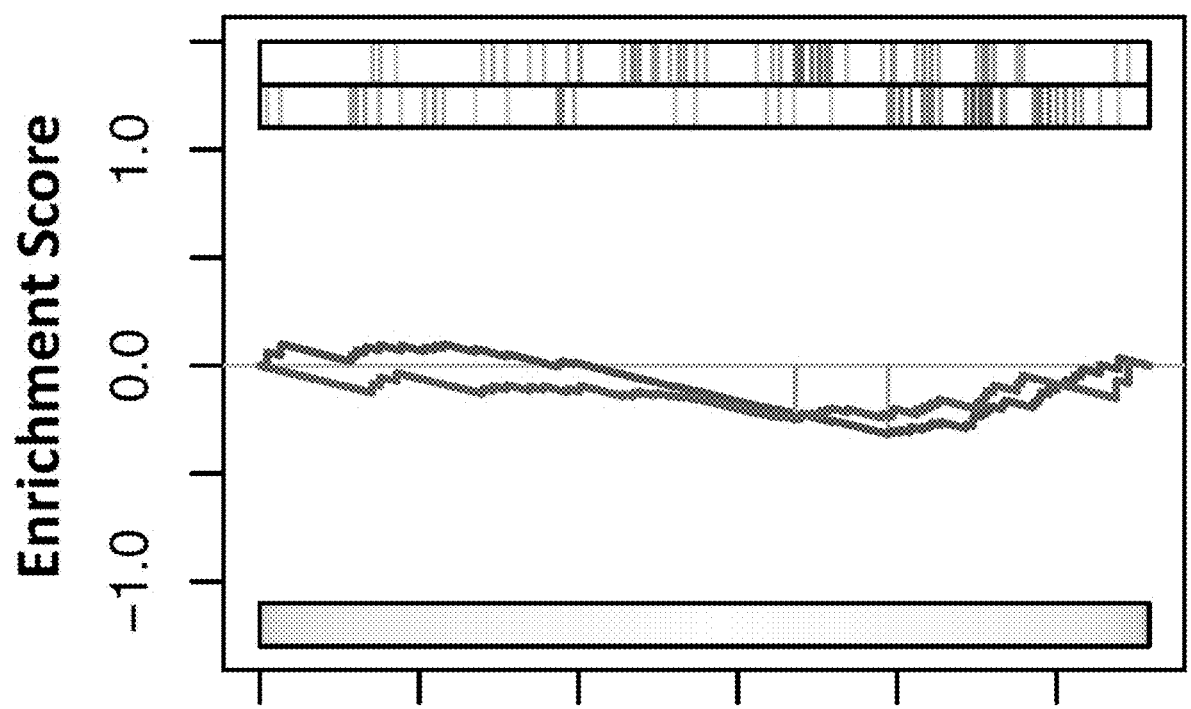

H-STS MR activity

H-STS Xenograft MR activity

SYSTEMS AND METHODS FOR MATCHING ONCOLOGY SIGNATURES

CROSS-REFERENCE TO RELATED APPLICATIONS

This application claims priority to U.S. Provisional Application Ser. No. 62/211,562, filed on Aug. 28, 2015, and 62/253,342, filed on Nov. 10, 2015, the content of which is incorporated by reference in its entirety, and to which priority is claimed.

GRANT INFORMATION

This invention was made with Government Support under Grant Nos. CA121852 and CA168426 awarded by National Institutes of Health. The Government has certain rights in the invention.

BACKGROUND

Certain efforts in precision cancer medicine are predicated on the identification of "actionable oncogene mutations", under the assumption that their pharmacological inhibition will elicit oncogene addiction[1]. Despite integration of this methodology into clinical cancer care, challenges remain.

First, stratification of cancer patients based on actionable mutations[2] has shown that certain adult malignancies lack actionable alterations altogether or present with mutations in undruggable oncogenes (e.g. RAS/MYC family proteins) or in genes of uncharacterized therapeutic value[3]. Additionally, while oncogene targeting can achieve initial responses, these can be followed by rapid relapse due to emergence of drug-resistance[4,5]. Also, analysis of hundreds of cell lines and compounds shows that, with the exception of a handful of well-characterized targets (e.g., ERBB2, EGFR, mTOR, ALK, MET, PI3K and ESR1, among others), single-gene mutations can be poor overall predictors of sensitivity to inhibitors of the corresponding protein[6].

Drug sensitivity represents a multifactorial, polygenic (i.e., complex) phenotype, highlighting the need for novel approaches that complement and extend the actionable alteration paradigm. Accordingly, there is a need for a novel approach that complements and extends the actionable alteration paradigm.

SUMMARY

The presently disclosed subject matter provides systems and methods to identify signatures representing aberrant activity of specific proteins (e.g., Master Regulator ("MR") proteins) in a tissue and to match said signatures to other tissue signatures, including following treatment with specific small molecules or biologics. As used herein, the term "Master Regulator (MRs)" refers to aberrantly activated/inactivated proteins in a tissue including these signatures, based on a predefined statistical threshold, e.g., at a p-value of about 0.01 or less, corrected for multiple hypothesis testing. These MR proteins can be necessary for tumor viability, and thus represent a novel class of therapeutic target, usually distinct from classical oncoproteins.

In accordance with certain embodiments of the presently disclosed subject matter, the systems and methods can be used to identify biological samples that represent diseases or disorders (e.g., tumors) with similar drug sensitivity based on MR activity signature similarity, to identify drugs and small molecule compounds that revert MR activity in a specific tissue, and to identify drugs that have complementary effect in reverting the activity of MR proteins, thus representing candidate synergistic drug-pairs.

The presently disclosed subject matter can be based on identification and reversal of tumor checkpoint activity (e.g., of the specific MR proteins driving the tumor cell state). For example, tumors, models, and drug responses can be matched based on the state and/or effect of the actual MR proteins regulating the tumor cell phenotype.

The presently disclosed subject matter provides methods of profiling a disease or a disorder. In certain embodiments, an example method includes measuring quantitatively protein activity of a plurality of MR proteins in a sample from the disease or disorder; and profiling the disease or disorder from the quantitative protein activity of the MR proteins. The sample can be selected from the group consisting of tissue extracts, cells, tissues, organs, blood, blood serum, body fluids and combinations thereof.

In certain embodiments, the profiling assesses or identifies MR proteins dysregulation status. In certain embodiments, the MR proteins dysregulation status includes aberrantly activated MR proteins and aberrantly inactivated MR proteins.

In certain embodiments, the profiling results in a MR signature profile for the disease or disorder. The MR signature profile for the disease or disorder subtype can be used in a method of identifying a cell line or a model as an in vivo or in vitro model for such disease or disorder. Such method can include measuring quantitatively protein activity of the MR proteins in a cell line or model, and profiling the cell line or model from the quantitative protein activity of the MR proteins to obtain a MR signature profile for the cell line or model. In certain embodiments, the method includes assessing the similarity between the MR signature profile for the cell line or model and the MR signature profile for the disease or disorder. The method can result in identification of a matched disease/disorder cell line or model whose MR signature profile is substantially statistically similar (p-value of about $1 \times 10^{-5}$ or less) to the MR signature profile for the disease or disorder. In certain embodiments, the model is selected from patient derived tumor xenograft models, mouse xenograft models and transgenic mouse models.

The presently disclosed subject matter further provides methods of identifying a compound that treats a disease or a disorder. In certain embodiments, an example method includes measuring quantitatively protein activity of a plurality of MR proteins in a sample from the disease or disorder; exposing the sample to the compound; measuring quantitatively protein activity of the plurality of MR proteins in the compound-treated sample; and assessing quantitatively inversion of protein activity of the plurality of MR proteins in the compound-treated sample compared to a sample from the disease or disorder without treatment with the compound or a model exposed to a vehicle used to deliver the compound. In certain embodiments, the vehicle can be Dimethyl sulfoxide (DMSO). A compound that induces global inversion of protein activity of the plurality of MR proteins indicates that the compound inhibits tumor cell growth of the tumor.

The presently disclosed subject matter further provides methods for identifying a pair of a first compound and a second that synergistically treats a disease or a disease. In certain embodiments, such method includes measuring quantitatively protein activity of a plurality of MR proteins in a sample from the disease or disorder; exposing a first sample from the disease or disorder to a first compound; exposing a second sample from the disease or disorder to a second compound; and assessing quantitatively inversion of protein activity of the plurality of MR proteins in the compound-treated first and second samples compared to a sample from the disease or disorder without treatment with the first or second compound or a model exposed to a vehicle used to deliver the first or second compound. In certain embodiments, a pair is identified as being capable of synergistically treating the disease or disorder if one or more of the following criteria are met: (a) if intersection of the MR proteins that the first and second compounds activate or inactivate represents a more statistically significant inversion of protein activity of the MR proteins; (b) if union of the MR proteins that the first and second compounds activate or inactivate represents a more statistically significant inversion of protein activity of the MR proteins; and (c) if the MRs that the first and second compounds individually invert have been predicted to be synergistic regulators of tumor state.

Furthermore, the presently disclosed subject matter provides methods of assessing in vivo therapeutic effect of a compound for treating a disease or disorder. In certain embodiments, an example method includes measuring quantitatively protein activity of a plurality of MR proteins in a sample from the disease or disorder; exposing the sample to the compound; measuring quantitatively protein activity of the plurality of MR proteins in the compound-treated sample; and assessing quantitatively inversion of protein activity of the plurality of MR proteins in the compound-treated sample compared to a sample from said disease or disorder without treatment with the compound or a model exposed to a vehicle used to deliver the compound. A compound that induces global inversion of protein activity of the plurality of MR proteins indicates that the compound will likely be effective for treating the disease or disorder in vivo.

The compound can be selected from small molecule chemical compounds, peptides, nucleic acids, oligonucleotides, antibodies, aptamers, modifications thereof, and combinations thereof.

The disease or disorder can be a tumor or a tumor subtype. The tumor can be selected from glioblastoma, meningioma, leukemia, lymphoma, sarcoma, carcinoid, neuroendocrine, paraganglioma, melanoma, prostate, pancreatic, bladder, stomach, colon, breast, head & neck, kidney, gastric, small intestine, ovarian, hepatocellular, uterine corpus, and lung carcinoma.

In any of the methods disclosed herein, measuring quantitatively protein activity of the plurality of MR proteins can be based directly or indirectly on expression of regulons of the MR proteins, and/or be based directly or indirectly on enrichment of regulons of the MR proteins. In certain embodiments, a regulon of a specific protein (e.g., a MR protein) is differentially expressed in a specific tissue, compared to a control tissue (e.g., the average of all disease/disorder (e.g., tumor)-related samples, normal samples, or untreated samples).

In any of the methods disclosed herein, measuring quantitatively protein activity of the plurality of MR proteins can include computationally inferring protein activity of the plurality of MR proteins from gene expression profiles of regulons of the MR proteins. In certain embodiments, the gene expression profiles are derived from in vivo models. In certain embodiments the gene expression profiles are derived from in vitro models. A regulon of a MR protein can be inferred by the Algorithm for the Reconstruction of Accurate Cellular Networks (ARACNe). The computationally inferring protein activity of the plurality of MR proteins can be performed by techniques such as the Master Regulator Inference algorithm (MARINA), and Virtual Inference of Protein-activity by Enriched Regulon analysis (VIPER).

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 9A-9E depict conservation of metastasis Master Regulators in NET cell lines and a xenograft model. (A) Enrichment of the top 100 most dysregulated proteins from each metastasis on each cell line and the H-STS xenograft model protein activity signature. (B-E) Gene Set Enrichment Analysis for the top 50 most activated and the top 50 most de-activated proteins in each selected metastasis on the protein activity signature of the H-STS cell line (B and C), and the H-STS xenograft model (D and E).

DETAILED DESCRIPTION

The presently disclosed subject matter provides methods to match signatures, including protein activity signatures inferred from gene expression profiling. The protein activity signatures can be, for example, inferred by VIPER. The methods disclosed herein can be used to identify: (a) biological samples that are similar because of their protein activity profiles, with the special case of matching models (cell lines, organoids, mouse models, etc.) to patient-derived tissue samples (e.g. tumor) because they recapitulates the activity of the key proteins that determine the tissue cellular phenotype, (b) drugs and small molecule compounds that as single agents revert the master regulators of cell state and hence, specifically destabilize the cellular phenotype thus abrogating tumor viability, and (c) drugs showing a synergistic (i.e. more than additive) effect in reverting the master regulators of cell state and hence, act synergistically in destabilizing the cellular phenotype and in abrogating tumor viability.

The key proteins, which are referred to as Master Regulators (MRs), are those having the highest positive (aberrantly activated) and highest negative (aberrantly inactivated) differential activity, compared to a control tissue, based on a statistical significance threshold (e.g., a p-value of about 0.01 or less corrected for multiple hypothesis testing). Control tissues can include the normal tissue from which a tumor is derived (e.g. normal breast epithelium for breast adenocarcinoma), the primary tumor for a metastatic sample, or a drug-sensitive tumor for one that is drug-resistant. The full set of MRs for a specific tumor is called a tumor checkpoint.

In the case of tumor tissue, MR proteins have been shown to constitute key determinant of tumor state and thus tumor specific dependencies whose aberrant activity is necessary for tumor viability. Thus, drugs that act as single agent or combinations revert the specific set of MRs for a particular tumor (e.g., a tumor checkpoint) represent potentially valuable therapeutic options.

Figure 1A:
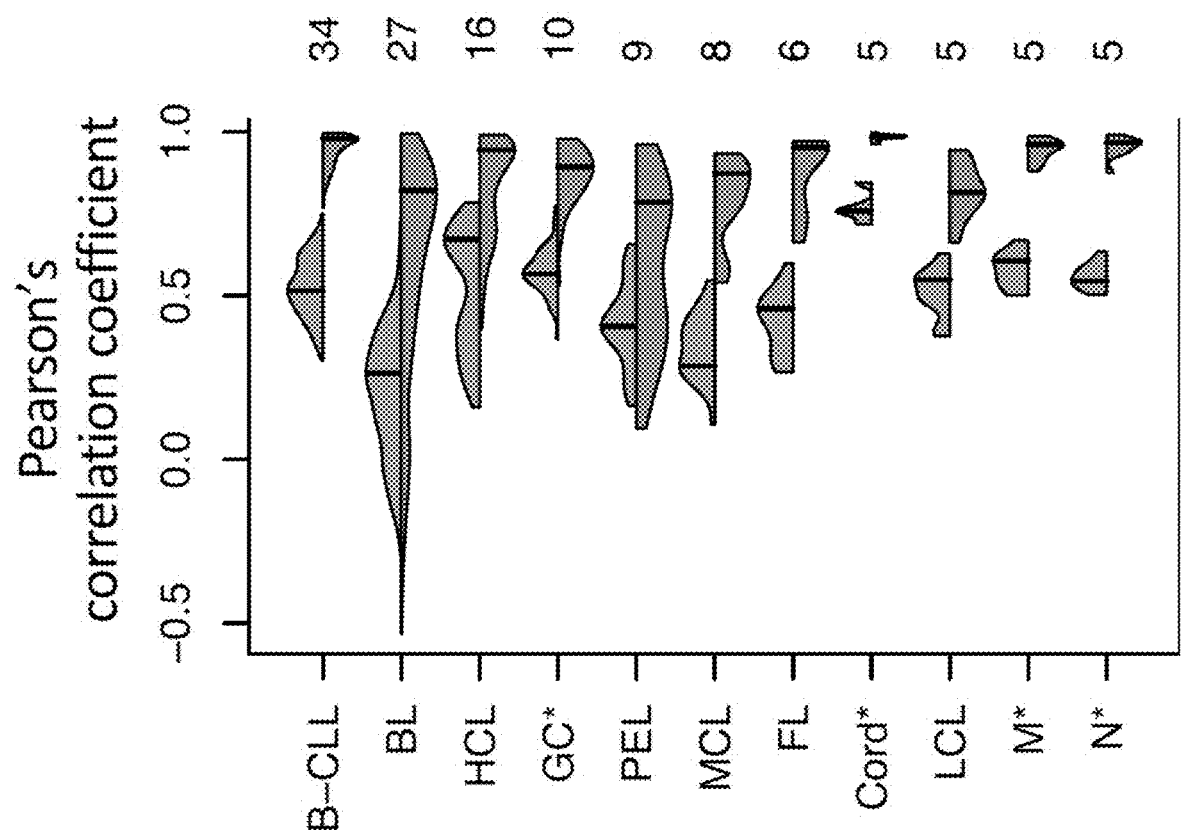
FIGS. 1A and 1B depict probability density for correlation coefficient and relative rank position for mRNA (yellow), Reverse Phase Protein Arrays (green) and VIPER-inferred protein activity (cyan) signatures.
Figure 1B:
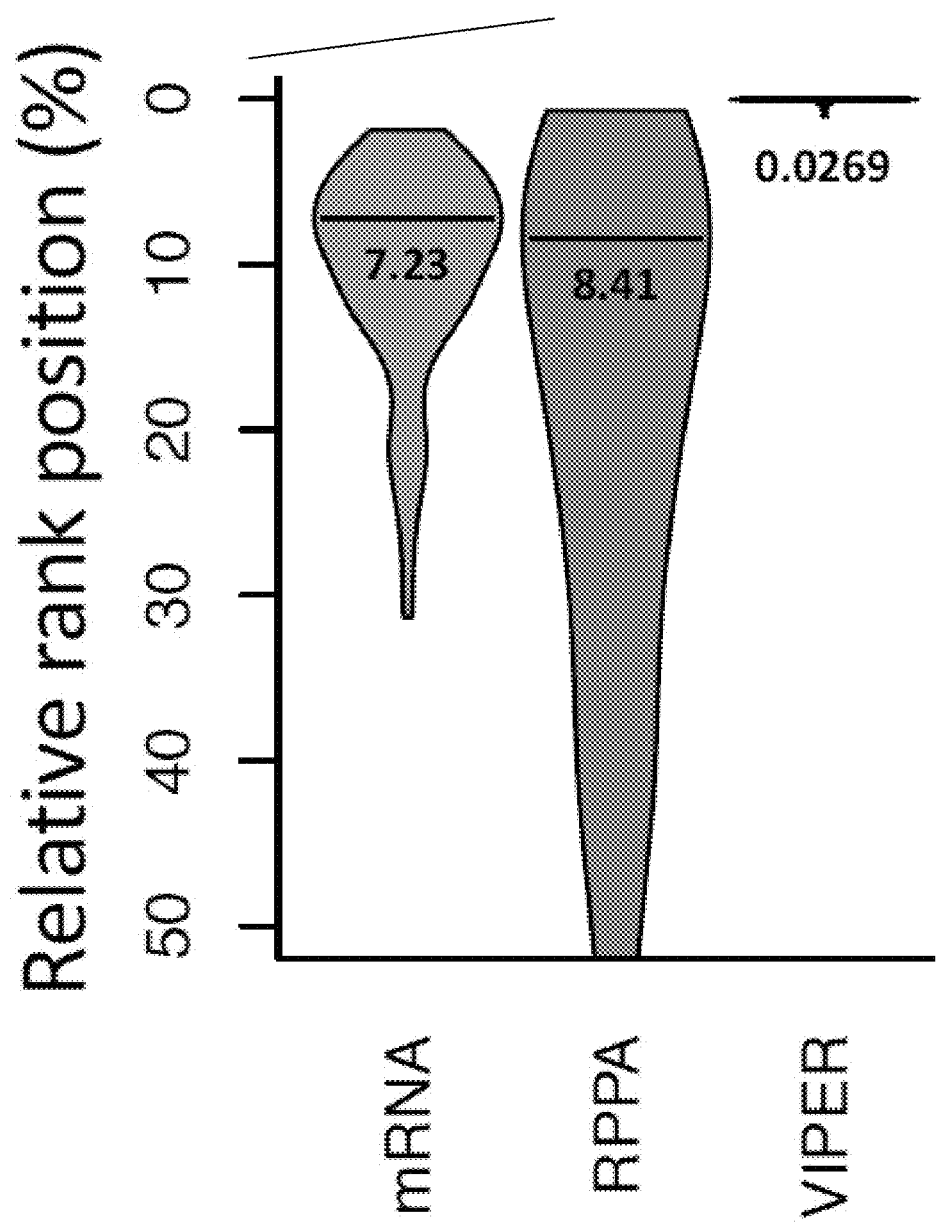
Figure 2A:
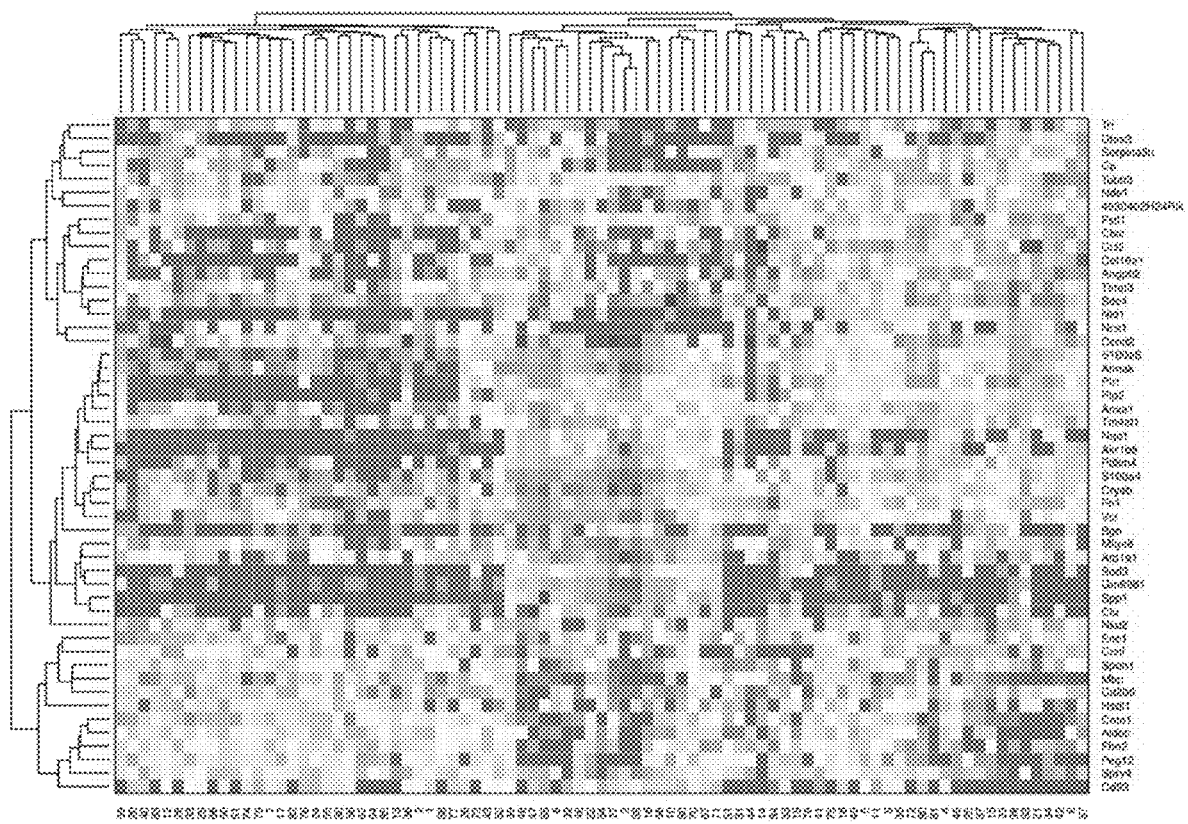
FIGS. 2A-2C depict heatmaps for gene expression (A and C) and VIPER-inferred protein activity (B). Red indicates upregulated genes or activated proteins, blue indicates downregulated genes or inactivated proteins, gray indicates missing data.
Figure 2B:
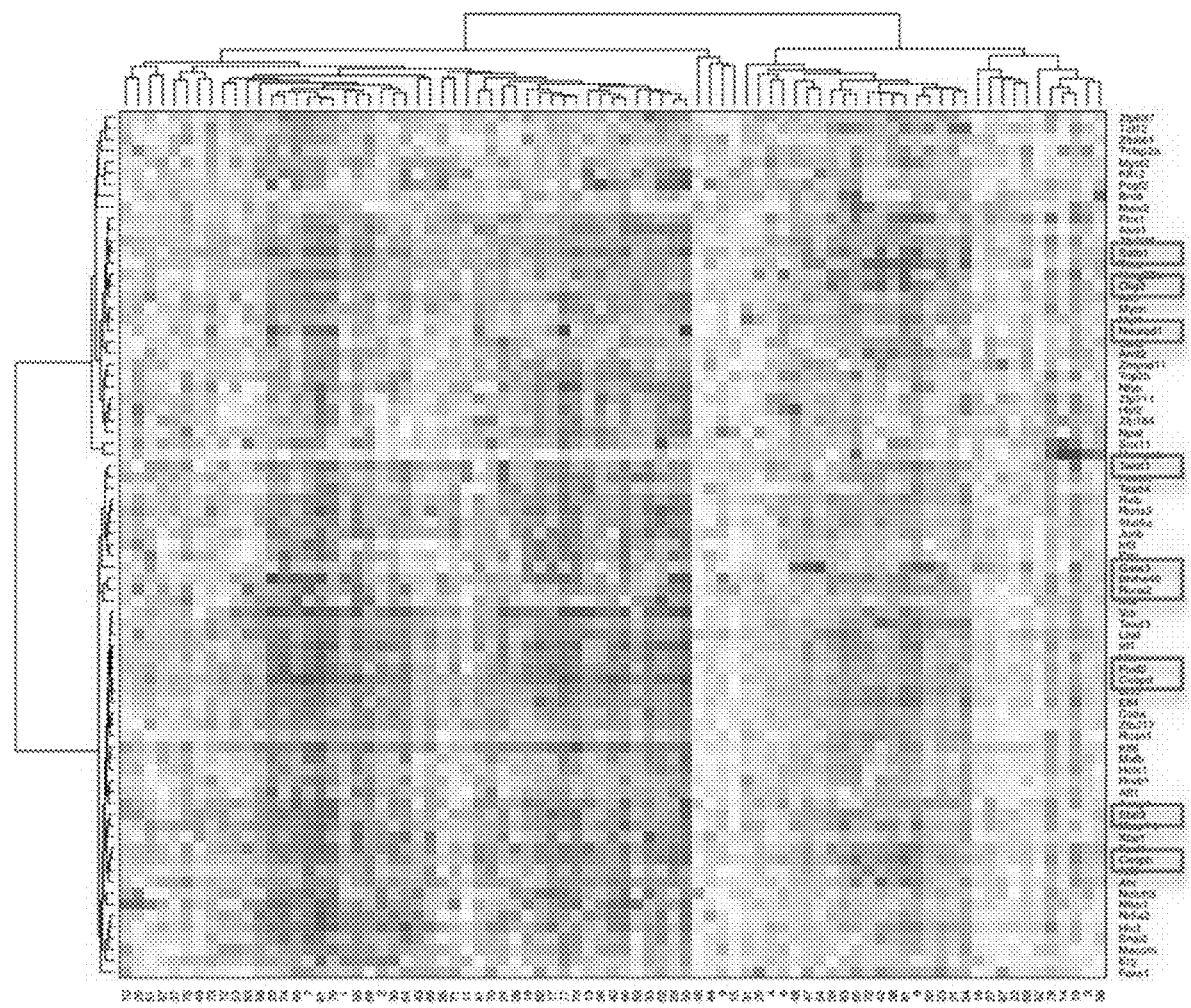
Figure 2C:
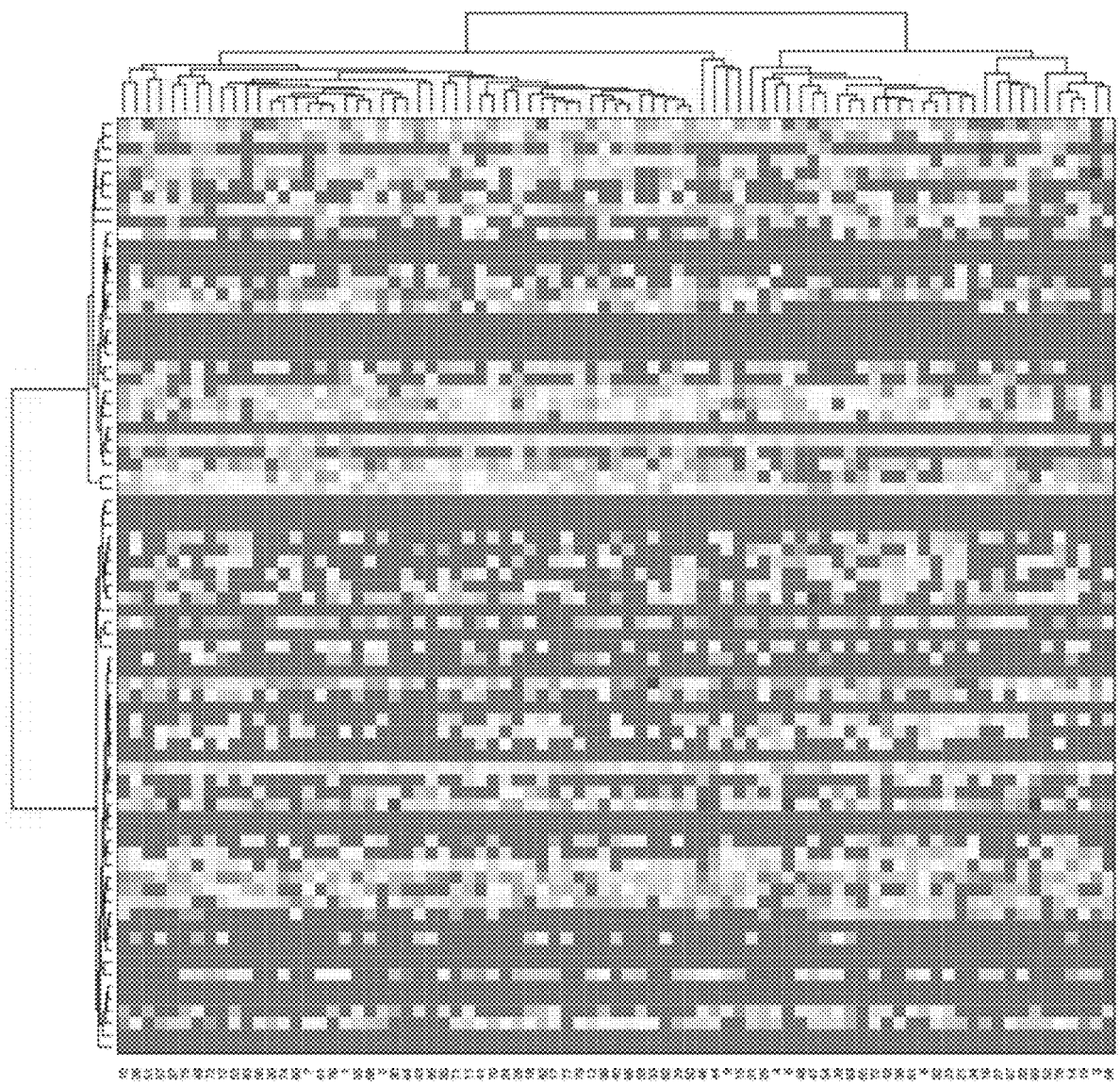

Certain methods to compare samples, tumors and models are based on their similarity at their gene expression or protein abundance levels, or conservation of genetic alterations. While the first two can be reliable at the population level and be useful for subtype discovery, they can be noisy (i.e. poorly reproducible) at the single tumor and single cell level (see FIGS. 1A, 1B and 2B). FIG. 1A illustrates the probability density for the correlation coefficient computed between samples from the same B-cell subtype based on expression (yellow) and VIPER-inferred protein activity (cyan). FIG. 1B illustrates the probability density for the relative rank position of the most over-expressed gene (mRNA, yellow), abundant protein (RPPA, green) or activated protein (VIPER, cyan) from one basal breast carcinoma tumor on the other basal breast carcinoma tumor profiled by TCGA. On the other hand, conservation of genetic alterations can be poorly reproducible, given the high number of possible combinations of genetic alterations and the poor correlate between such alterations and tumor subtypes. An unsupervised cluster analysis of single cells isolated from a single glioblastoma tumor was performed based on gene expression or VIPER-inferred protein activity, and the results are shown in FIGS. 2A (for gene expression) and 2B-2C (for VIPER-inferred protein activity). While no clear stratification can be detected based on gene expression (see FIG. 2A), the analysis that involved VIPER-inferred protein activity showed a strong separation of the cells in two sub-populations, which are defined by the differential protein activity of previously characterized regulators of the proneural and mesenchymal subtypes (see FIG. 2B). FIG. 2C shows the same arrangement of cells (columns) and genes (rows) as in FIG. 2B, indicating that the sub-populations and associated genes cannot be identified directly from the gene expression profile data.

An exemplary disclosed method that involves protein activity-signatures inferred from gene expression profiling (e.g., VIPER-inferred protein activity-signatures), and in particular tumor checkpoints, can be robust when compared to gene expression and protein abundance (RPPA) (see FIGS. 1A and 1B). This can involve two key properties of the protein activity inferred from gene expression profiling (e.g., VIPER-inferred protein activity): (1) protein activity is inferred by integrating the expression of tens to hundreds of genes (e.g., VIPER-inferred protein activity), which constitute an endogenous multiplexed reporter assay for the activity of the assessed protein (its regulon), while RNA expression and RPPA rely on the noisy measurement of a single species; and (2) only gene expression patterns produced by transcriptional regulatory programs can be captured (e.g., by VIPER), and hence patterns produced by technical artifacts, including batch effects, are efficiently removed (e.g., by VIPER).

Exemplary disclosed methods (e.g., OncoMatch and OncoTreat methodologies discussed below) can involve conservation of tumor checkpoints (e.g., on proteins driving tumor cell state), and thus can match tumors, models and drug response based on the state and effect of the actual proteins regulating the tumor cell phenotype.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

1. Master Regulator Proteins and Tumor Checkpoints

In accordance with the presently disclosed subject matter, master regulator (MR) proteins include proteins whose activity is statistically significantly dysregulated (including both activated and inactivated proteins)—whose transcriptional targets (regulon) are differentially expressed in a disease or disorder (e.g., a tumor), at a specific statistical significance threshold (e.g., a p-value of about 0.01 or less).

As used herein, the term "tumor checkpoint" refers to a pivotal regulatory module comprising a plurality of MR proteins (e.g., MR proteins whose coordinated activity is necessary for maintaining tumor viability) for a specific tumor. Coordinated aberrant activity of MR proteins in a tumor checkpoint is necessary to maintain a tumor cell state and thus to ensure tumor viability.

The reasons for calling these modules tumor checkpoints because—much as a highway checkpoint—they channel and integrate the signaling traffic originating from a wide and diverse range of upstream mutations and aberrant signals.

Genetic and/or pharmacological MR protein inhibition can lead to tumor checkpoint collapse and loss of tumor viability both in vitro and in vivo, e.g., as shown in lymphoma[7,8], glioblastoma[9], prostate[10,11] and breast cancer[12]. Further extension of this concept to drug-resistance has led to identification of MR proteins whose pharmacologic inhibition rescues drug sensitivity, including in leukemia[13] and breast cancer[12]. Stat3, CEBP-beta, and CEBP-delta were identified as the tumor checkpoint for glioblastoma; FOXM1, and CENPF were identified as the tumor checkpoint for prostate cancer; Notch-1, RUNX1, TLX1 and TLX3 were identified as the tumor checkpoint for leukemia; Myc, BCL6, and BCL2 were identified as the tumor checkpoint for lymphoma; AKT1 was identified as the tumor checkpoint for T-cell acute lymphoblastic leukemia (T-ALL) resistant to glucocorticoid therapy; and MYCN and TEAD4 were identified as the tumor checkpoint for neuroblastoma.

MRs in tumor checkpoints are rarely mutated or even differentially expressed[9,10]; rather they implement tightly autoregulated modules that integrate the effect of a large and diverse repertoire of genetic and epigenetic alterations in upstream pathways[7,14].

MR proteins elicit tumor essentiality[7] and synthetic lethality[8-10,12], thus representing classic non-oncogene dependencies[15,16] and can suggest a novel class of pharmacological targets. MR proteins can be efficiently and systematically prioritized by interrogating genome-wide regulatory networks with tumor-related gene expression signatures representing either an entire tumor subtype or individual tumor samples using the Master Regulator Inference algorithm (MARINa)[9,17] and its single sample equivalent Virtual Inference of Protein-activity by Enriched Regulon analysis (VIPER)[18]. Functional and biochemical evaluation of MARINa/VIPER inferred MR proteins has yielded validation rates in the 70% to 80% range[8-10,12].

2. Methods of Profiling a Disease or a Disorder

The presently disclosed method quantifies the extent of conservation, at the level of protein activity, between a tissue, cell culture or single cell sample, or a specific perturbation, and a cellular state of interest, characterized by its master regulator (MR) proteins of cell state, or tumor checkpoint in the case of tumor. The analysis can be performed by inferring the MR proteins of cell state for the phenotype of interest, and then computing the enrichment of such master regulators on the full regulatory protein activity signature of the second tissue or cell, or obtained in response to chemical perturbations. The enrichment can be computed by the analytic Rank Enrichment Analysis algorithm, part of VIPER.

In certain embodiments, the method of profiling a disease or a disorder (e.g., a tumor) includes measuring quantitatively protein activity of a plurality of MR proteins in a sample from the disease or disorder; and profiling the disease or disorder from the quantitative protein activity of the MR proteins.

The method results in determination of a Master Regulator (MR) signature profile for a disease or a disorder, e.g., a tumor. As used herein, a "Master Regulator (MR) signature profile for a disease or a disorder" refers to a protein activity profile of Master Regulators (MRs) which is characteristic of the disease or disorder. Such a MR signature profile is the result of a quantitative determination of protein activity of a plurality of MR proteins in a sample from the disease or disorder compared to the protein activity of such MR proteins in an adequate control or reference (e.g., healthy individuals, different types of the disease or disorder, or different stages of the disease or disorder), thereby identifying which combination of MR proteins allows for differentiation of the disease, type or stage of disease or disorder over the control or reference.

The signature profile obtained from the presently disclosed method allows for diagnosis of a general disease or disease (e.g., tumor) condition, distinction between different types (subtypes) of the disease or disorder (e.g., tumor), distinction between different stages (e.g., metastatic progression) of the disease or disorder (e.g., tumor), predictive diagnosis of further evolution of the disease or disorder (e.g., tumor), and identification of responsiveness to a specific therapy. The profiling methods can be used to identify a cancer type, including, but not limited to, a malignant tumor, a benign tumor, a primary tumor, a secondary tumor, an aggressive tumor, and a non-aggressive tumor.

Profiling the disease or disorder (e.g., tumor) can assess or identify MR proteins dysregulation status. In certain embodiments, the MR proteins dysregulation status includes aberrantly activated MR proteins and aberrantly inactivated MR proteins.

In certain embodiments, the ability to identify MR proteins depends on the availability of accurate models of tissue-specific regulation, representing both direct targets of transcription factors (TFs) and least-indirect targets of signaling proteins (SPs). TFs and SPs can be effectively inferred by analyzing large, tumor-specific gene expression profile datasets using the Algorithm for the Accurate Reconstruction of Cellular Networks (ARACNe)[19,20], as supported by extensive experimental validation assays[9,10,17,21]. ARACNe analysis of tumor-specific gene expression profile can produce a tumor-specific regulatory network (interactome), which can be used both to assess protein activity on an individual sample basis, for optimal cluster analysis, as well as to elucidate novel MRs.

Protein activity of the MR proteins can be based directly or indirectly on expression of regulons of the MR proteins. Additionally or alternatively, protein activity can be based directly or indirectly on enrichment of regulons of the MR proteins. As used herein, the term "regulon" refers to the transcriptional targets of a protein, e.g., a MR protein. Regulon of a specific protein (e.g., a MR protein) can be differentially expressed in a specific tissue, compared to a control tissue (e.g., the average of all tumor-related samples, normal samples, or untreated samples). A regulon of a specific protein (e.g., a MR protein) can be inferred by the Algorithm for the Reconstruction of Accurate Cellular Networks (ARACNe).

In certain embodiments, measuring quantitatively protein activity of the MR proteins include computationally inferring protein activity of the MR proteins from gene expression profiles of regulons of the MR proteins. The gene expression profiles can be derived from in vivo models. Additionally or alternatively, the gene expression profiles can be derived from in vitro models. Computational inference of protein activity of MR proteins can be performed by a suitable data analysis system, e.g., MARINA and/or VIPER techniques. In certain embodiments, the technique is VIPER.

VIPER allows computational inference of protein activity, on an individual sample basis, from gene expression profile data. VIPER infers protein activity by systematically analyzing expression of the protein's regulon[18]. VIPER uses the expression of genes that are most directly regulated by a given protein, such as the targets of a TF, as an accurate reporter of its activity. Analysis of TF targets inferred by ARACNe[19,20], using MARINA[17], can be effective in identifying drivers of specific cellular phenotypes, which can be experimentally validated[9,7]. While VIPER exploits the same principle as MARINA, it implements a dedicated algorithm specially formulated to estimate regulon activity, which takes into account the regulator mode of action, the regulator-target gene interaction confidence and the pleiotropic nature of each target gene regulation. In addition, VIPER can effectively extend to signal transduction proteins. The VIPER technique is described in Alvarez et al., Nat. Genet. (2016); 48(8): 838:847, U.S. Patent Provisional Application No. 62/211,373, and U.S. patent application Ser. No. 15/248, 975 entitled "Virtual Inference Of Protein Activity By Regulon Enrichment Analysis" filed contemporaneously herewith, which are incorporated by reference in their entireties.

Protein activity, inferred from single-sample transcriptome readouts using VIPER, can be a more robust descriptor of cell state than gene expression[18]. The reason is three-fold. First, VIPER-inferred protein activity represents a more direct and mechanistic determinant of cell state, compared to gene expression; second, while individual gene expression measurements are quite noisy (i.e. poorly reproducible) and poorly reproducible, VIPER infers protein activity from the expression of a large number (tens to hundreds) of its transcriptional targets (e.g., the protein's regulon), thus resulting in much higher accuracy and reproducibility[18]; third, bias and technical noise that is inconsistent with the regulatory model is effectively filtered out, thus effectively removing a major source of confounding data. VIPER can effectively segregate samples according to tissue of origin.

Figure 3:
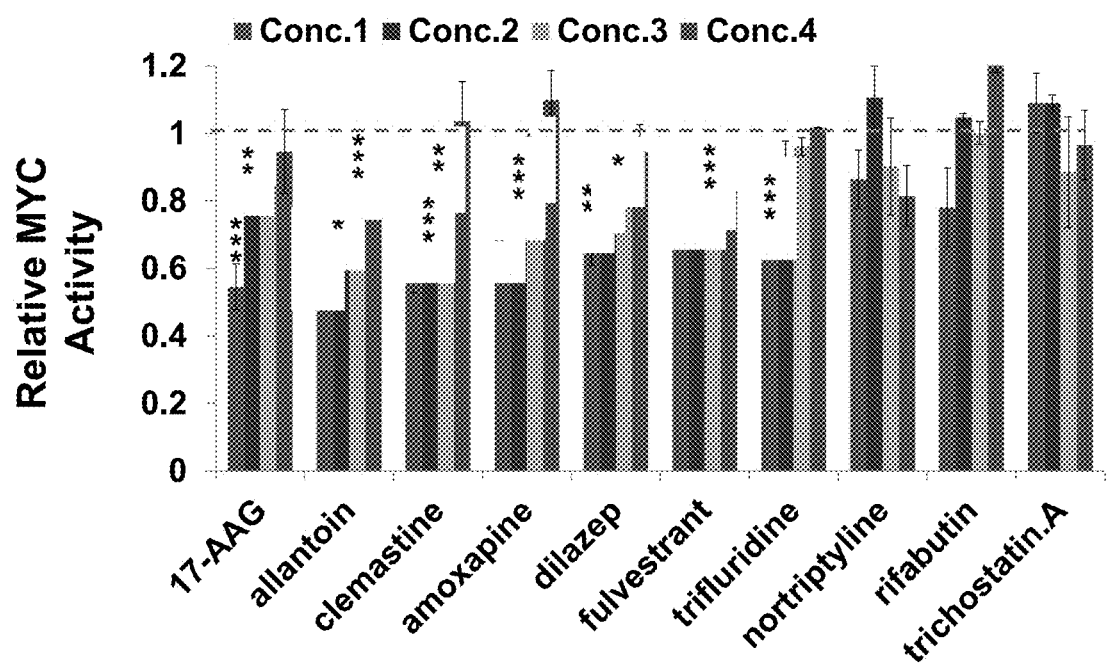
FIG. 3 depicts validation of VIPER-inferred MYC inhibitors in MCF7 cells. * $p<0.05$;  $p<0.01$; * $p<0.001$.

VIPER analysis of gene expression signatures representing cellular responses to compound perturbations in vitro or in vivo can identify MRs representing physical compound targets (e.g., enzymes for which the compound represents a high-affinity substrate) and effectors (e.g., proteins not directly bound by the drug but necessary for it to perform its pharmacological activity), also known as the compound Mechanism of Action (MoA). VIPER can outperform gene expression analysis in the elucidation of compound MoA. This can be because small molecules generally act post-translationally to affect the activity (rather than expression) of their targets/effectors which affects the expression their transcriptional targets. In fact, this analysis can be used to identify agents effectively targeting the MR protein activity (see FIG. 3). FIG. 3 shows the results of TERT-promoter-luciferase based reporter assay activity in response to 4 serial dilutions at ½ starting from each compound IC20 at 24 h, to ensure operation at sub-lethal regime. Seven of the top 10 compounds predicted by VIPER to inhibit MYC protein activity showed a dose-dependent inhibition of its activity on the TERT-promoter-based reporter assay.

In certain embodiments, the disease or disorder is a tumor or a tumor subtype. As used herein, the term "tumor subtype" refers to a collection of tumors with similar molecular characteristics. Non-limiting examples of samples include tissue extracts, cells, tissues, organs, blood, blood serum, body fluids and combinations thereof. Non-limiting examples of tumors include glioblastoma, meningioma, leukemia, lymphoma, sarcoma, carcinoid, neuroendocrine, paraganglioma, melanoma, prostate, pancreatic, bladder, stomach, colon, breast, head & neck, kidney, gastric, small intestine, ovarian, hepatocellular, uterine corpus, and lung carcinoma. Other diseases or disorders include, but are not limited to, neurogenerative disorders (e.g., amyotrophic lateral sclerosis, Parkinson's disease, and Alzheimer disease etc.), diabetes, obesity, and other metabolic diseases.

3. Methods of Identifying Compounds that Treats a Disease or a Disorder

When activity of an essential MR or MRs (e.g., a pair of MRs) is abrogated, the entire MR activity pattern can collapse. This is because MRs generally operate as tight (i.e., highly-interconnected) regulatory modules, acting as regulatory switches to maintain cell state, normal or tumor-related. As a result, a compound that inhibits an essential MR or MRs can be screened or identified by measuring the global protein activity change of VIPER-inferred tumor-MRs, following treatment in representative cells (see FIG.

4A). Compounds with greatest effect in inverting the activity of the full repertoire of tumor checkpoint, can do so by targeting one or more essential MRs or MR-pairs, and can thus abrogate tumorigenesis in vivo.

The presently disclosed method relates to prioritization of compounds (e.g., small molecules) as MR inhibitors to induce drug-mediated tumor checkpoint collapse and regression in vivo, including on an individual patient basis. Candidate MR proteins have been individually validated to identify essential MRs[7,12] or synthetic lethal MR pairs[8-10]. This process can be slow, costly, and inefficient for prioritizing patient treatment in a precision cancer medicine context. Yet, since inhibition of essential MRs or MR-pairs can induce global tumor checkpoint collapse (i.e., global inversion of the activity of all MRs in the module), there is a strong rational to using the patient-specific tumor checkpoint activity (i.e. the signature of the entire MR proteins signature) as a gene reporter assay to identify compounds capable of inducing tumor checkpoint collapse and consequent loss of tumor viability in vivo, without requiring extensive and time consuming MR validation.

The presently disclosed subject matter provides for a method of identifying a compound that treats a disease or a disorder (e.g., inhibits tumor cell growth). In certain embodiments, the disease or disorder is a tumor or a tumor subtype. In certain embodiments, the method includes: measuring quantitatively protein activity of a plurality of MR proteins in a sample from the disease or disorder (e.g., tumor); exposing the sample to the compound; measuring quantitatively protein activity of the plurality of MR proteins in the compound-treated sample; and assessing quantitatively inversion of protein activity of the plurality of MR proteins in the compound-treated sample compared to a sample from the disease or disorder (e.g., tumor) without treatment with the compound or a model exposed to a vehicle that is used to deliver the compound, e.g., DMSO. A compound that induces global inversion of protein activity of the plurality of MR proteins indicates that the compound treats the disease or disorder (e.g., tumor).

Global inversion of protein activity f a plurality of MR proteins following treatment with compound(s) can be assessed based on the statistical significance of enrichment of MR proteins that are inactivated following compound treatment in MR proteins that are aberrantly activated in the tumor, and/or enrichment of MR proteins that are activated following compound treatment in MR proteins that are aberrantly inactivated in the tumor. The aREA technique can be used to measure the statistical significance of protein enrichment. The statistical significance of protein enrichment can be measured by any suitable enrichment analysis, including, but not limited to, Gene Set Enrichment Analysis or related methodologies at a pre-defined p-value threshold (e.g., a p-value of about 0.01 or less, e.g., $1\times10^{-5}$, corrected for multiple hypothesis testing).

Non-limiting examples of compounds include small molecule chemical compounds, peptides, nucleic acids, oligonucleotides, antibodies, aptamers, modifications thereof, and combinations thereof.

Figure 4A:
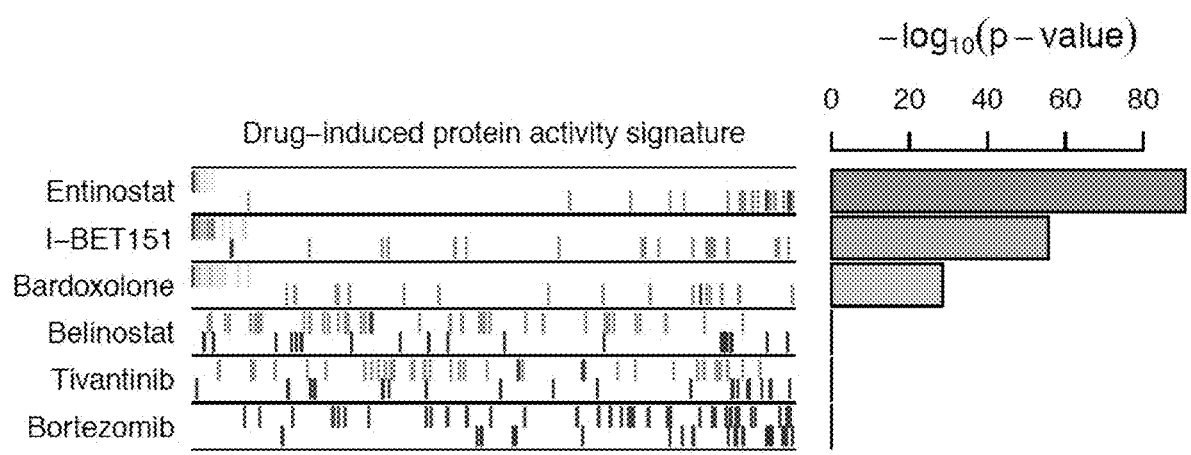
FIGS. 4A and 4B. (A) Enrichment of NET-MET checkpoint MRs on drug-response VIPER-inferred protein activity signatures. (B) Effect of Entinostat (HDAC inhibitor identified by oncoMatch approach), Belinostat (HDAC inhibitor not affecting NET-MET checkpoint) and Tivantinib on H-STS xenograft growth.
Figure 4B:
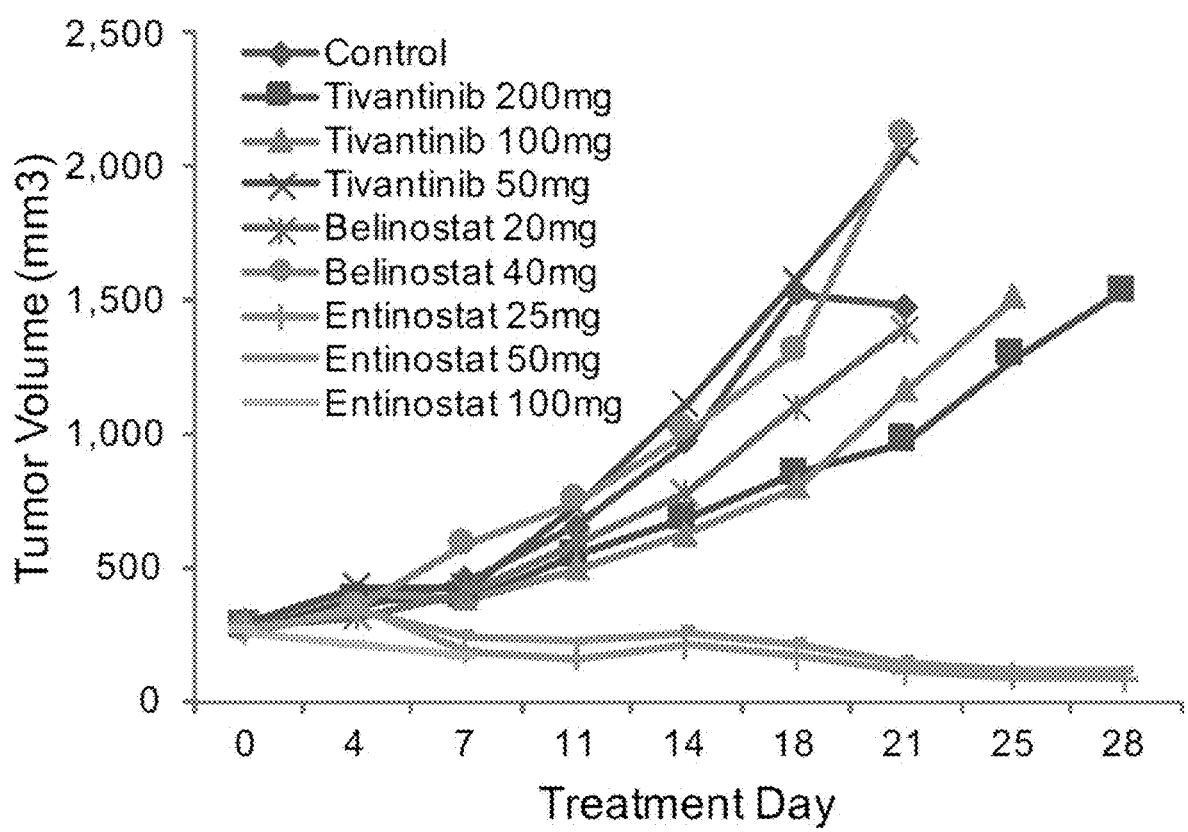
Figure 6A:
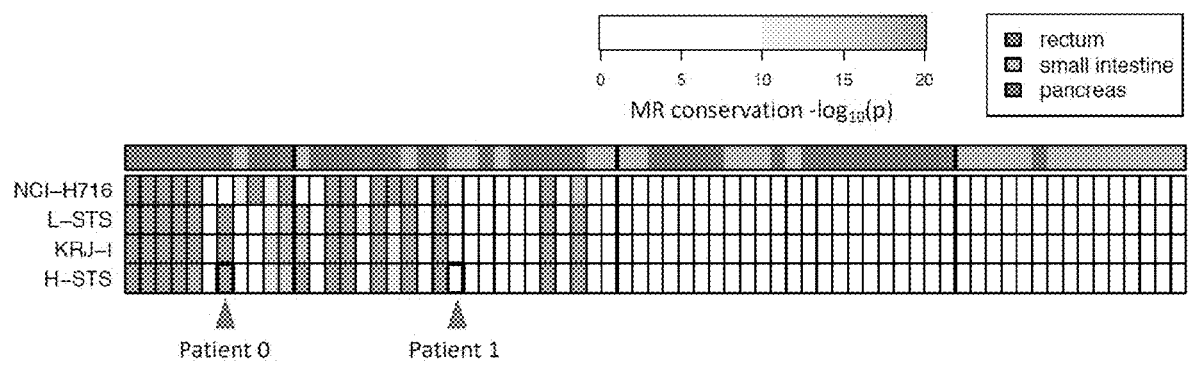
FIGS. 6A-6E. (A) OncoMatch scores for 4 cell lines indicating the extent to which they recapitulate the NET-MET checkpoint of individual tumor metastasis. (B and C) Enrichment of the NET-MET checkpoint for two patients on H-STS cell line VIPER-inferred protein activity signature. (D) Heatmap indicating the oncoMatch score for 55 cell lines (columns) as models for each of 173 basal breast carcinoma samples (rows). Only matches at p-value $<10^{-10}$ are shown with orange color. (E) Selection of 3 cell lines best covering the basal breast carcinoma tumor space (173 tumors). Blue bars indicate cell line-specific coverage. Red bars show the cumulative coverage.

By utilizing a presently disclosed screening method, entinostat was identified as the most potent agent for reverting the rectal neuroendocrine tumor metastasis (NET-MET) tumor checkpoint (see FIG. 4A). Drug MoA information was inferred using a NET liver metastasis-derived cell line (H-STS), which recapitulated the tumor checkpoint inferred from patient's samples (FIG. 6A). When tested in xenograft models, entinostat abrogated completely tumor growth (FIG. 4B).

The presently disclosed subject matter further provides a method of identifying a pair of compounds (a first compound and a second compound) that synergistically treats a disease or a disorder (e.g., inhibits tumor cell growth). In certain embodiments, such method includes: measuring quantitatively protein activity of a plurality of MR proteins in a sample from the disease or disorder (e.g., tumor); exposing a first sample from the disease or disorder to a first compound; exposing a second sample from the disease or disorder (e.g., tumor) to a second compound; and assessing quantitatively inversion of protein activity of the plurality of MR proteins in the first and second compound-treated samples to a sample from the disease or disorder (e.g., tumor) without treatment with the compound or a model exposed to a vehicle that is used to deliver the compound, e.g., DMSO.

Assessment on whether a pair of the first and second compounds is synergistic can be based on one or more of the following criteria: (a) if intersection of the MR proteins that the first and second compounds activate or inactivate represents a more statistically significant inversion of protein activity of the MR proteins; (b) if union of the MR proteins that the first and second compounds activate or inactivate represents a more statistically significant inversion of protein activity of the MR proteins; and (c) if the MRs that the first and second compounds individually invert have been predicted to be synergistic regulators of disease/disorder (e.g., tumor) state. More statistically significant in this context is defined by the difference in the statistical significance obtained by the combination of compounds and the most significant individual compound. Such difference can be calculated at the normalized enrichment score level.

Synergistic interaction between compounds is obtained when the effect of the combination is higher than the additive effect of the individual agents. This is critical because with synergistic compound combinations, it is possible to achieve the therapeutic effect while using doses lower than the ones that would be required if the compounds are used in isolation, decreasing in this way compound-related toxicity and unwanted secondary effects. Following a similar reasoning to the one used to match individual compounds to tumor checkpoints (see FIG. 4A), compounds that affect complementary subsets of the tumor checkpoint MRs can synergize in inducing loss of cell viability.

4. Methods of Identifying Cell Lines and Models for Diseases or Disorders

By directly matching the dysregulated protein activity for the MRs that constitute the tumor checkpoint, a presently disclosed method can be used to identify a cell line or a model (e.g., a genetically engineered mouse model or a patient derived xenograft (PDX) model) that represents the best surrogate model to study a patient-specific disease or disorder (e.g., a tumor) because it recapitulates the key MRs in the tumor checkpoint. The quality of the match can be assessed based on the statistical significance of the enrichment of activated and inactivated MR proteins in proteins that are most activated or inactivated in the cell line or model, as computed by gene set enrichment analysis methods such as GSEA or aREA.

Thus, the presently disclosed subject matter provides for a method of identifying a cell line or a model as an in vitro or in vivo model for a patient-specific disease or disorder, e.g., to increase the confidence that drugs that can abrogate viability in these models may work in the patient(s). In certain embodiments, the disease or disorder is a tumor or a tumor subtype.

Such method can include measuring quantitatively protein activity of the MR proteins in the cell line or model, and profiling the cell line or model from the quantitative protein activity of the MR proteins to obtain a MR signature profile for the cell line or model. Additionally, the method can include assessing the similarity between the MR signature profile for the cell line or model and the MR signature profile for the disease or disorder (e.g., tumor or tumor subtype) to identify a matched disease/disorder (e.g., tumor or tumor subtype) cell line or model whose MR signature profile is substantially statistically similar (p-value of $1\times10^{-5}$ or less) to the MR signature profile for the disease or disorder (e.g., tumor or tumor subtype). Non-limiting examples of models include PDX models, mouse xenograft models, and transgenic mouse models.

This analysis was performed to select H-STS as the NET cell line recapitulating the tumor checkpoint of several rectal NET-MET (see FIGS. 6A and 6B), to prioritize a set of 3 cell lines recapitulating the checkpoint of 95% of TCGA basal breast carcinoma tumors (see FIGS. 6D and 6E), and to select the most appropriate genetically engineered mouse model of aggressive prostate carcinoma.

5. Methods of Assessing In Vivo Therapeutic Effects of Compounds for Treatments

The presently disclosed method can be used to assess the extent at which the predicted effect of a compound or a pair of compounds in vitro, is recapitulated in vivo in preclinical models before its therapeutic application in patients with diseases or disorders (e.g., tumors). This can be performed by computing the enrichment of the tumor checkpoint MRs on compound(s)-induced protein activity signature obtained by VIPER-analysis of in vivo models-derived expression profile data.

The presently disclosed subject matter provides for methods of assessing in vivo therapeutic effect of a compound for treating a disease or a disorder. In certain embodiments, the disease or disorder is a tumor. Such method can include measuring quantitatively protein activity of a plurality of MR proteins in a sample from the disease or disorder (e.g., tumor); exposing the sample to the compound; measuring quantitatively protein activity of the plurality of MR proteins in the compound-treated sample; and assessing quantitatively inversion of protein activity of the plurality of master regulator proteins in the compound-treated sample compared to a sample from the disease or disorder (e.g., tumor) without treatment with the compound or a model exposed to a vehicle used to deliver the compound (e.g., DMSO). A compound that induces global inversion of protein activity of the plurality of MR proteins indicates that the compound will likely be effective for treating the disease or disorder (e.g., tumor) in vivo (see FIGS. 10D and 10E).

EXAMPLES

The following examples are merely illustrative of the presently disclosed subject matter and should not be considered as a limitation in any way.

Example 1

Validation of Myc Inhibitors Predicted by VIPER

17-AAG, allantoin, amoxapine, chlorthalidone, clemastine, dilazep, etoposide, fulvestrant, furazolidone, and ionomycin were predicted by VIPER to be Myc inhibitors. TERT-promoter-luciferase based reporter assay was performed on these compounds to assess their Myc inhibitory activity. As shown in FIG. 3, seven of these 10 compounds predicted by VIPER to inhibit Myc protein activity showed a dose-dependent inhibition of its activity on the TERT-promoter-based reporter assay.

Example 2

Identification of Compounds that Synergistically Reverting Tumor Checkpoints

Figure 5A:
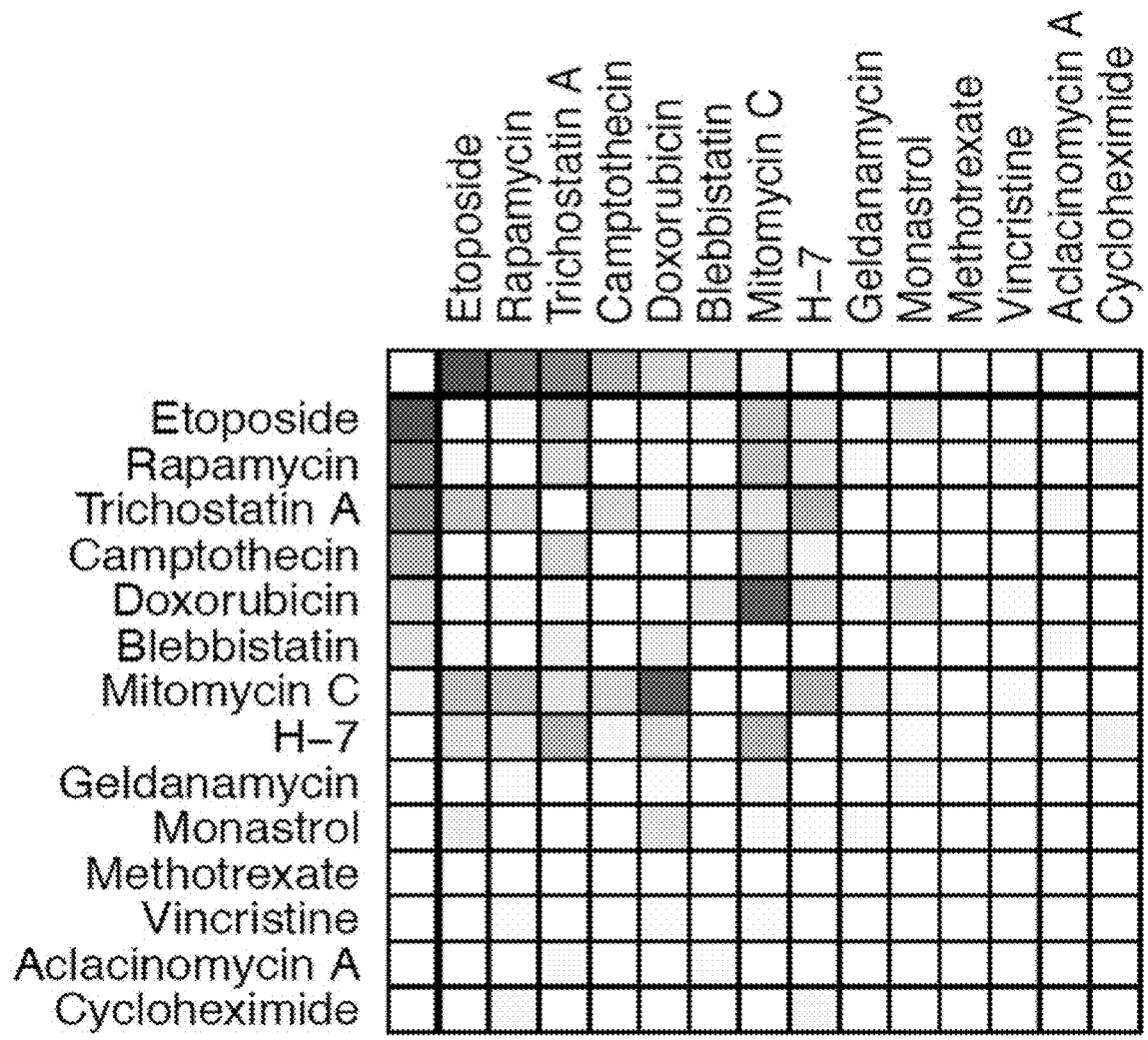
FIGS. 5A and 5B. (A) Heatmap showing the synergistic score (indicated as red color intensity), inferred as the increase in enrichment of each drug pair combination MoA compared to the single compounds MoA (indicated as blue color intensity in the first row and column). (B) Receiver operating characteristic curve showing the prediction of synergistic interaction for all combinations of the 14 assessed compounds. Indicated are the 16 compound pairs found by Bliss additivity to be synergistic (2012 DREAM challenge dataset). 8/16 (50%) synergistic pairs were identified at a 10% FPR.
Figure 5B:
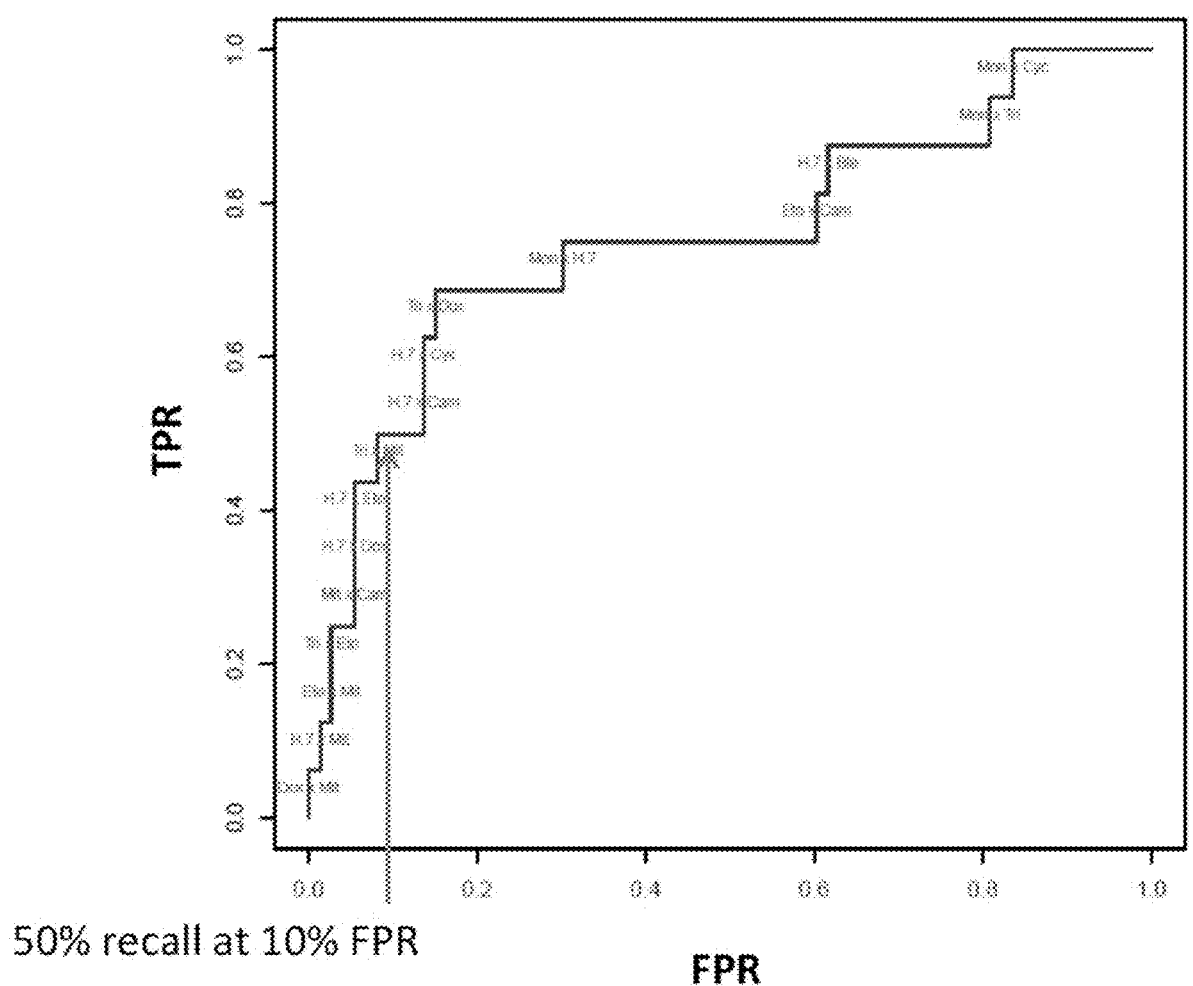

Gene expression profiles were generated following OCI-LY3 DLBCL cell perturbation with 14 distinct compound at three time points (6 h, 12 h, and 24 h) and 2 concentrations (IC20 at 24 h and ⅒th of that), in triplicate. These data were used to predict compound synergy. A second dataset of CellTiterGlo cell viability assays at 60 h, following treatment with each of 91 unique compound-pairs, using a 4×4 dilution matrix starting at each compound IC50, was generated to evaluate the disclosed approach and 31 additional submissions to the DREAM/NCI drug sensitivity challenge. Synergy was experimentally assessed by using the second set to compute the Excess Over Bliss (EOB); that is, whether the combined effect of two compounds is significantly greater or smaller than the sum of their individual effects (Bliss Independence). Statistical significance was assessed by comparing the difference in the mean of multiple assessment compared to the standard deviation of these measurements. Compound pairs were thus ranked from most synergistic to most antagonistic using the EOB. The disclosed approach was not developed to predict antagonism and was thus evaluated only on synergy. In this context, it outperformed all other 31 methods, essentially doubling the sensitivity of the next best technique. Indeed, of the top 10% most significant predictions, ~60% were experimentally validated as synergistic (see FIGS. 5A and 5B).

Example 3

Identification of Entinostat as the Most Potent Agent for Reverting Rectal Neuroendocrine Tumor Metastasis (NET-MET) Tumor Checkpoint Drug-induced VIPER-inferred protein activity signatures were obtained for a few drugs including entinostat. As shown in FIG. 4A, among all the tested drugs, entinostat was the most potent agent for reverting the rectal neuroendocrine tumor metastasis (NET-MET) tumor checkpoint. Drug MoA information was inferred using a NET liver metastasis-derived cell line (H-STS), which recapitulated the tumor checkpoint inferred from patient's samples, as shown in FIG. 6A. When tested in xenograft models (H-STS xenograft models), entinostat abrogated completely tumor growth, while belinostat (an HDAC inhibitor not affecting NET-MET checkpoint) did not abrogate tumor growth, as shown in FIG. 4B.

Example 4

Selection of Cell Lines Recapitulating Tumor Checkpoint

Figure 6B:
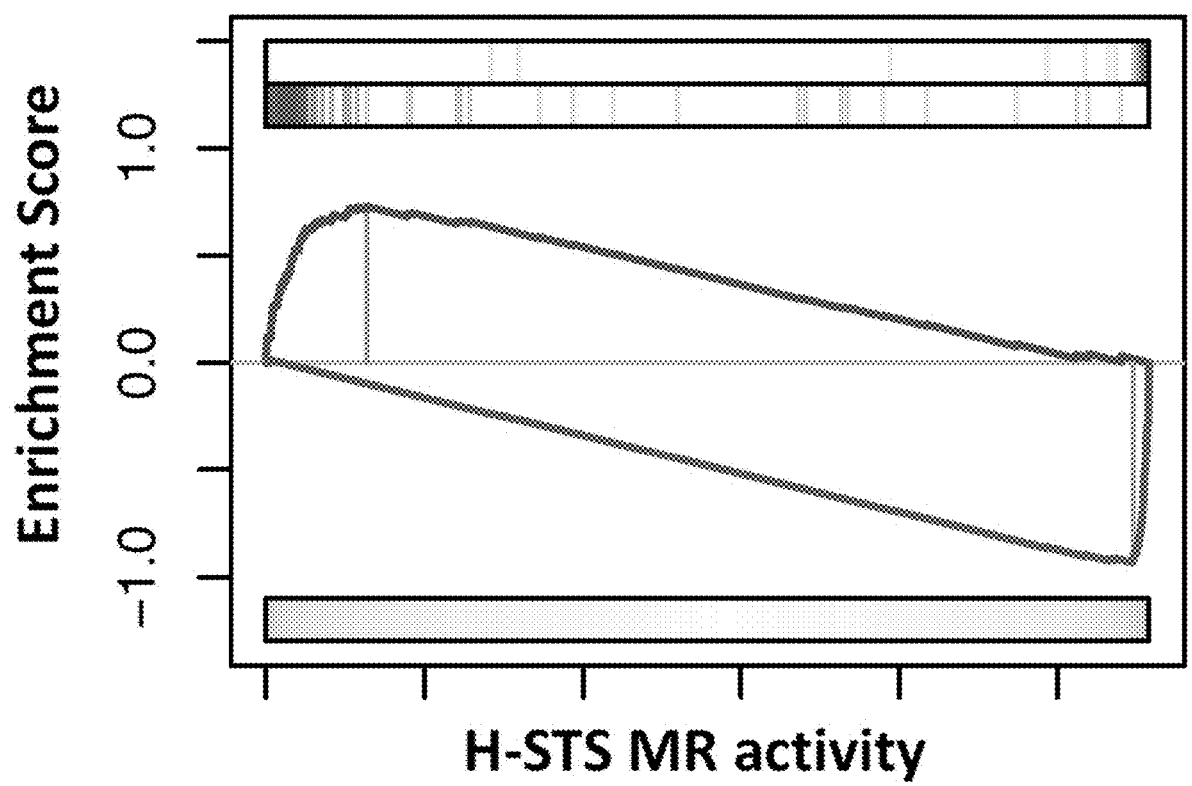
Figure 6C:
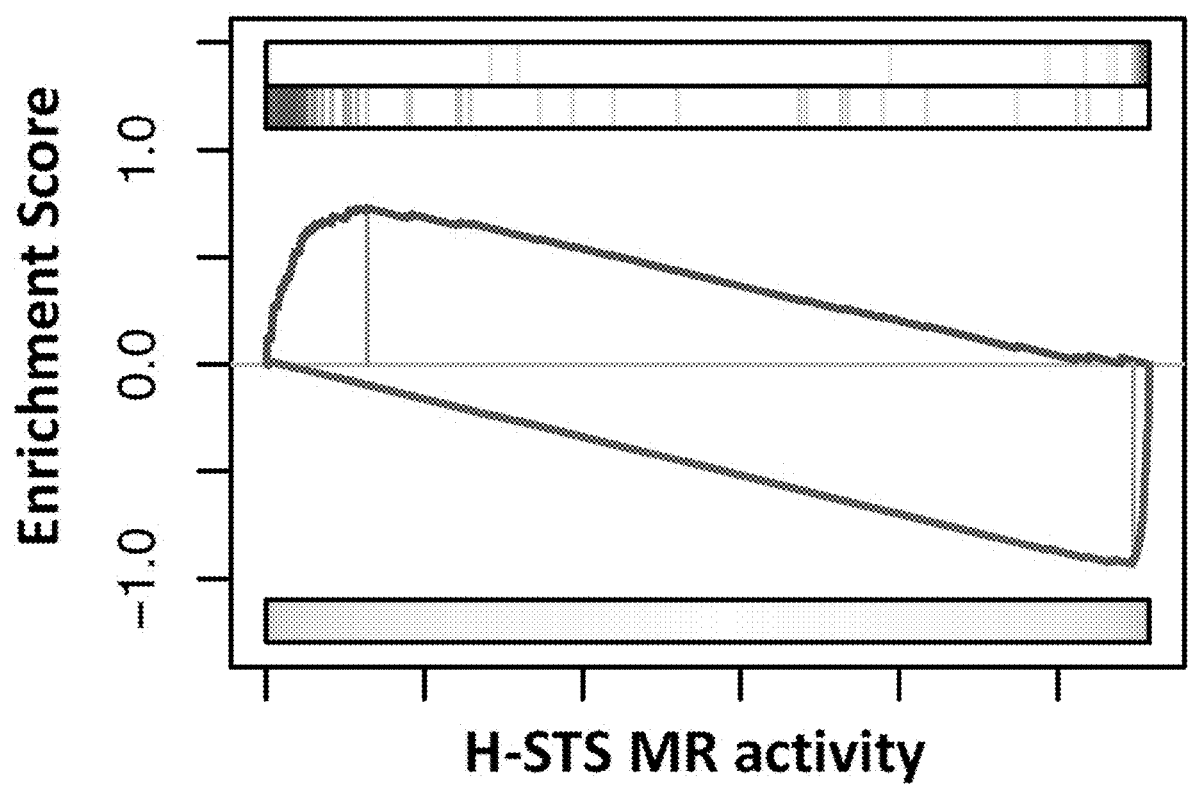
Figure 6D:
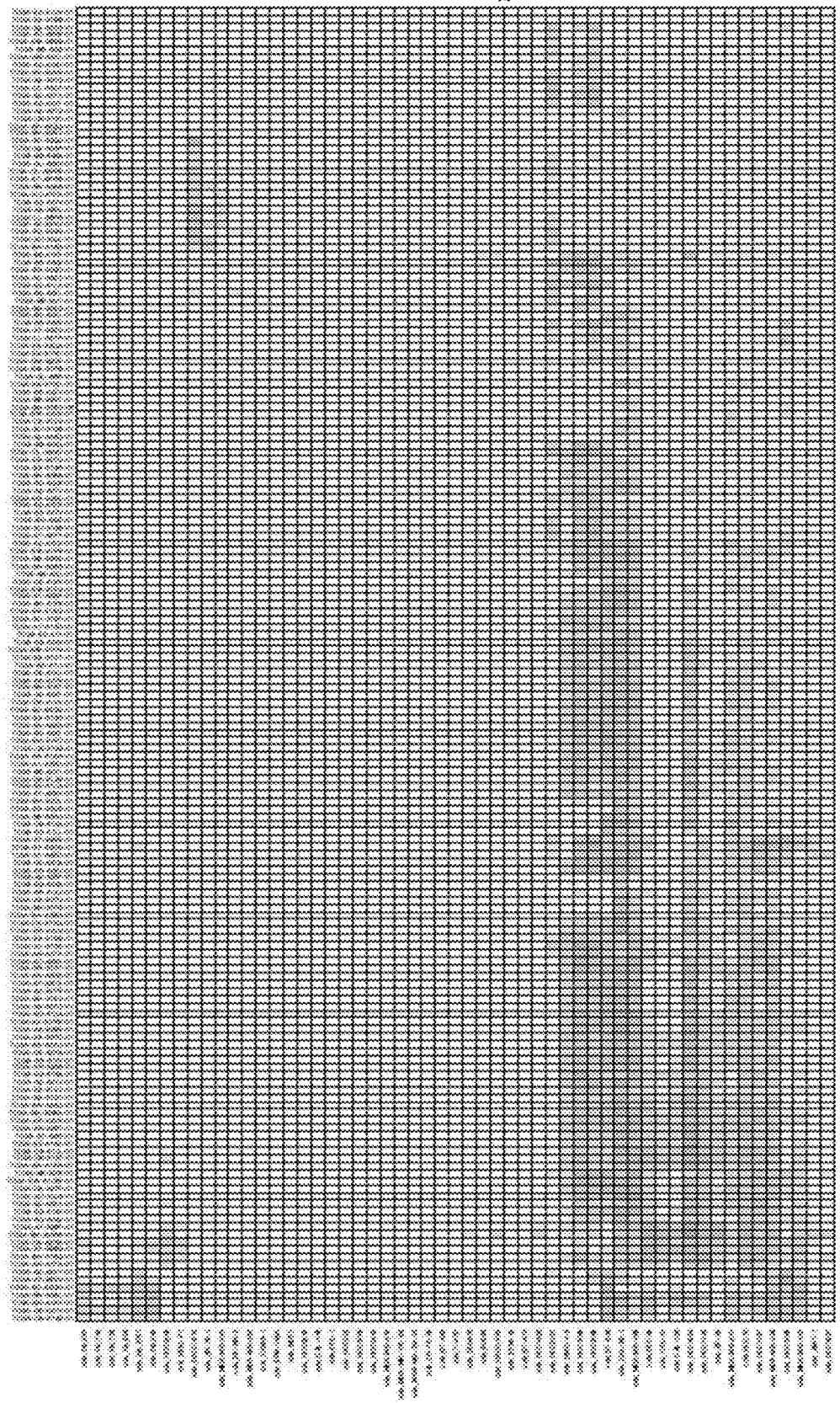
Figure 6E:
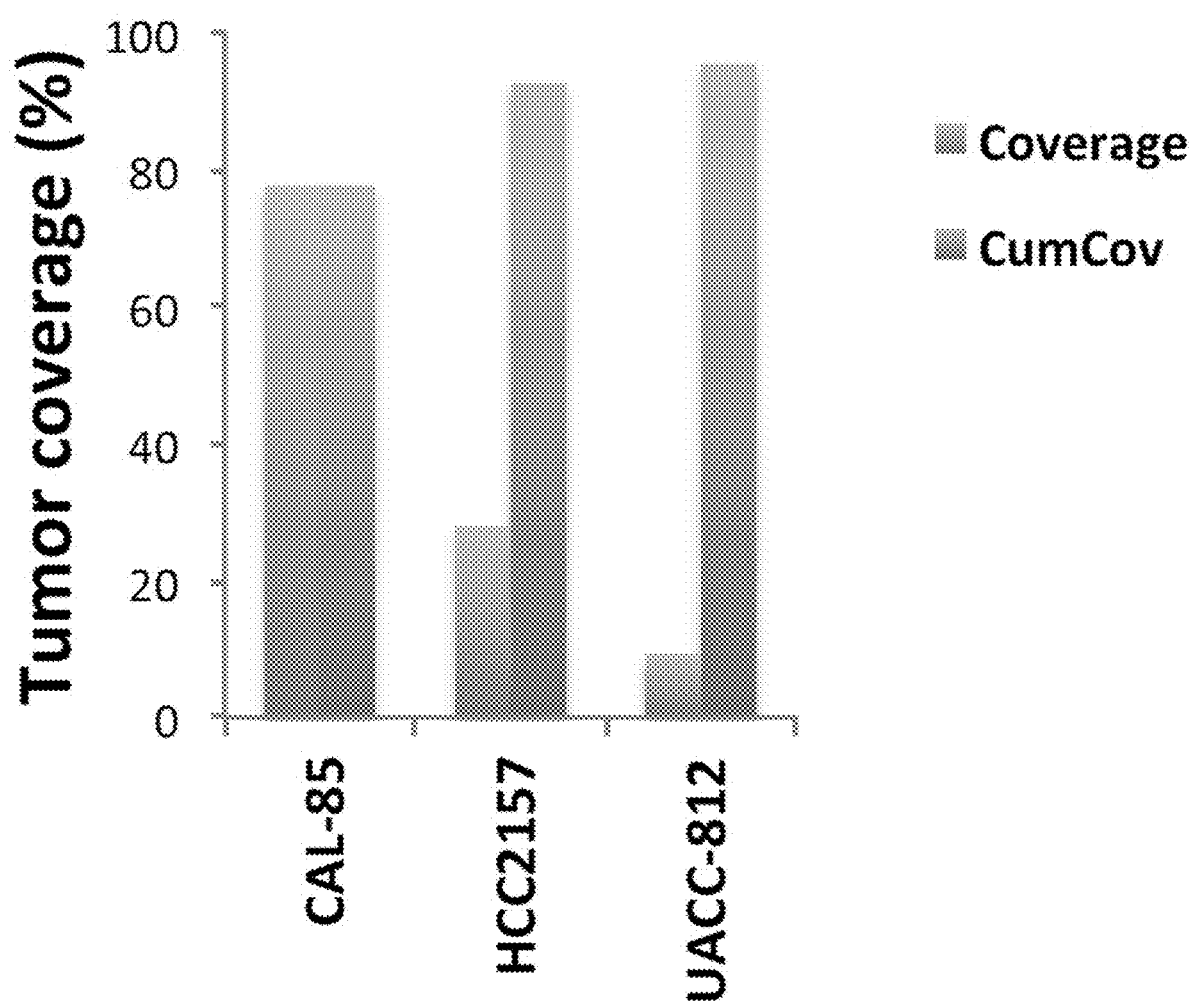

By directly matching the dysregulated protein activity for the MRs that constitute the tumor checkpoint, H-STS was selected as the NET cell line recapitulating the rectal NET-MET tumor checkpoint (see FIGS. 6A and 6B, and a set of 3 cell lines were prioritized as breast carcinoma cell lines recapitulating the checkpoint for 95% of TCGA basal breast carcinoma tumors (see FIGS. 6D and 6E).

Example 5

Systematic Pharmacological Targeting of Master Regulator Proteins in Neuroendocrine Tumors: A Novel Strategy for Precision Cancer Medicine Applications Summary This example is directed to a novel precision cancer medicine approach ("OncoTreat"; also referred to as "OncoMatch") using the systematic identification and pharmacological inhibition of master regulator (MR) proteins, whose concerted aberrant activity represents a critical dependency of cancer cells. FDA-approved and investigational compounds were prioritized based on their ability to abrogate MR activity based on analysis of large-scale perturbational assays. OncoTreat was applied to a cohort of 211 enteropancreatic neuroendocrine tumors (EP-NET) originating from pancreatic (PAN-NET), small intestine (SI-NET) and colorectal (RE-NET) primaries. RNASeq profiles were first used to assemble an EP-NET-specific regulatory model, whose interrogation identified MR proteins necessary for maintenance of metastatic tumor state. Analysis of RNASeq profiles representing EP-NET cell perturbation with 108 compounds prioritized them based on their ability to abrogate the MR activity patterns of individual patients. In vivo validation confirmed that the compound inducing the most profound checkpoint MR activity inversion elicited dramatic response in vivo, suggesting that the approach can extend and complement precision cancer medicine approaches based on oncogene addiction.

Introduction

Emerging efforts in precision cancer medicine are almost invariably predicated on the identification of "actionable oncogene mutations", under the assumption that their pharmacological inhibition will elicit oncogene addiction[1]. Despite remarkable initial successes, which have led to rapid integration of this methodology into clinical cancer care, significant challenges are emerging. First, stratification of cancer patients based on actionable mutations[2] has shown that a majority of adult malignancies lack actionable alterations altogether or present with mutations in undruggable oncogenes (e.g. RAS/MYC family proteins) or in genes of uncharacterized therapeutic value[3]. Additionally, while oncogene targeting can achieve initial responses that are at times remarkable, these are frequently followed by rapid relapse due to emergence of drug-resistance[4,5]. Finally, analysis of hundreds of cell lines and compounds shows that, with the exception of a handful of well-characterized targets (e.g., ERBB2, EGFR, mTOR, ALK, MET, PI3K and ESR1, among others), single-gene mutations are poor overall predictors of sensitivity to inhibitors of the corresponding protein[6]. This is not entirely surprising, as drug sensitivity clearly represents a multifactorial, polygenic (i.e., complex) phenotype, thus further highlighting the urgent need for novel approaches that complement and extend the actionable alteration paradigm.

OncoTreat or OncoMatch explored systematic strategies for the prioritization of small molecule compounds as MR inhibitors to induce drug-mediated tumor checkpoint collapse and regression in vivo, including on an individual patient basis. Candidate MR proteins have been individually validated to identify essential MRs[7,12] or synthetic lethal MR pairs[8-10]. This process can be slow, costly, and inefficient for prioritizing patient treatment in a precision cancer medicine context. Yet, since inhibition of essential MRs or MR-pairs has been shown to induce global tumor checkpoint collapse (i.e., global inversion of the activity of all MRs in the module), there is a strong rational to using the patient-specific tumor checkpoint activity (i.e. the signature of the entire MR proteins signature) as a gene reporter assay to identify compounds capable of inducing tumor checkpoint collapse and consequent loss of tumor viability in vivo, without requiring extensive and time consuming MR validation.

OncoTreat or OncoMatch was tested on a rare class of enteropancreatic neuroendocrine tumors (EP-NET), representing pancreatic, small-bowel, and rectal NETs. Once they undergo metastatic progression, these tumors are essentially incurable and have poor prognosis. Using a cohort of 211 fresh frozen EP-NET patient samples collected at 17 institutions, MR proteins responsible for metastatic progression can be prioritized on an individual tumor basis and then prioritized a set of 108 compounds with differential EP-NET cell sensitivity, based on their ability to globally invert the activity pattern of these MRs rather than on the basis of viability assays. Validation in tumor xenografts selected to specifically match the MR-activity profile of individual patients confirmed the utility of the OncoTreat or OncoMatch program and support that OncoTreat or OncoMatch program can provide a valuable complement to genetic based strategies in precision cancer medicine.

Methods

Agent Efficacy Evaluation:

All test agents were formulated according to manufacturer's specifications. Beginning Day 0, tumor dimensions were measured twice weekly by digital caliper and data, including individual and mean estimated tumor volumes (Mean TV±SEM), were recorded for each group. Tumor volume was calculated using the formula: $TV = width^2 \times length \times \pi/2$.

Tumor Growth Inhibition and RECIST:

At study completion, percent tumor growth inhibition (% TGI) values were calculated and reported for each treatment group (T) versus control (C) using initial (i) and final (f) tumor measurements by the formula: $\% TGI = [1-(T_f-T_i)/(C_f-C_i)] \times 100$. Individual mice reporting a tumor volume >120% of the Day 0 measurement were considered to have progressive disease (PD). Individual mice with neither sufficient shrinkage nor sufficient tumor volume increases are considered to have stable disease (SD). Individual mice reporting a tumor volume ≤70% of the Day 0 measurement for two consecutive measurements over a seven day period were considered partial responders (PR). If the PR persisted until study completion, percent tumor regression (% TR) was determined using the formula: $\% TR = (1-T_f/T_i) \times 100$; a mean value was calculated for the entire treatment group. Individual mice lacking palpable tumors for two consecutive measurements over a seven day period were classified as complete responders (CR). All data collected in this study were managed electronically and stored on a redundant server system.

Results

Assembling and Characterizing an EP-NET Tumor Cohort:

To identify and pharmacologically target MR proteins presiding over metastatic EP-NET cell state, a large collection of 211 fresh-frozen samples assembled at 17 distinct institutions across North America, Europe, and Asia (i.e., The International NET Consortium, iNETCon) can be leveraged. The collection includes both primary and metastatic samples from pancreatic (PanNET: 83 and 30 respectively), small intestine (SI-NET: 44 and 37, respectively), and colorectal (RE-NET: 3 and 15, respectively) EP-NETs. Total RNA was isolated and sequenced by Illumina TruSeq profiling, at an average depth of 30M SE reads (Table 1).

TABLE 1

EP-NET profiled samples. Mapper reads in millions.

| SampleID | Type | Tissue Origin | Mapped Reads |
|---|---|---|---|
| AC47 | liver met | rectum | 351.3 |
| AC452 | liver met | rectum | 170.8 |
| AC455 | liver met | rectum | 136.2 |
| AC508 | liver met | rectum | 110.6 |
| AC509 | liver met | rectum | 148.2 |
| AC510 | liver met | rectum | 141.9 |
| AC241 | liver met | rectum | 250.5 |
| AC242 | liver met | rectum | 206.7 |
| AC243 | liver met | rectum | 245.3 |
| AC246 | liver met | rectum | 172.6 |
| AC261 | liver met | small intestine | 160.9 |
| AC274 | liver met | small intestine | 179.6 |
| AC534 | primary | rectum | 183.8 |
| AC535 | primary | rectum | 202.7 |
| AC100 | primary | pancreas | 32.1 |
| AC103 | primary | pancreas | 28.8 |
| AC105 | primary | pancreas | 30.4 |
| AC106 | primary | pancreas | 28 |
| AC108 | primary | pancreas | 28.6 |
| AC110 | primary | pancreas | 32.9 |
| AC111 | primary | small intestine | 25.7 |
| AC113 | primary | small intestine | 38.6 |
| AC114 | primary | pancreas | 32.6 |
| AC115 | primary | pancreas | 30.9 |
| AC116 | primary | pancreas | 34.8 |
| AC121 | primary | pancreas | 26.1 |
| AC123 | primary | pancreas | 31.6 |
| AC125 | primary | pancreas | 34.5 |
| AC126 | primary | pancreas | 33.3 |
| AC127 | primary | small intestine | 30.3 |
| AC130 | primary | pancreas | 31 |
| AC133 | primary | small intestine | 25.3 |
| AC137 | primary | pancreas | 33.8 |
| AC139 | primary | pancreas | 32.7 |
| AC141 | primary | small intestine | 36.3 |
| AC143 | primary | small intestine | 30.4 |
| AC146 | primary | small intestine | 24.5 |
| AC147 | primary | small intestine | 28.7 |
| AC153 | primary | pancreas | 35.4 |
| AC157 | primary | small intestine | 35.1 |
| AC158 | primary | small intestine | 33.5 |
| AC162 | primary | small intestine | 43.8 |
| AC188 | primary | small intestine | 23.9 |
| AC196 | primary | small intestine | 15.6 |
| AC199 | primary | small intestine | 26.4 |
| AC203 | primary | small intestine | 35.5 |
| AC205 | primary | small intestine | 26.8 |
| AC206 | primary | small intestine | 28 |
| AC208 | primary | small intestine | 25.8 |
| AC209 | primary | pancreas | 18.6 |
| AC210 | primary | pancreas | 23.9 |
| AC211 | primary | pancreas | 27.7 |
| AC212 | primary | pancreas | 28.4 |
| AC213 | primary | pancreas | 29.5 |
| AC214 | primary | pancreas | 25.9 |
| AC215 | primary | pancreas | 27.3 |
| AC216 | primary | pancreas | 38.8 |
| AC218 | primary | pancreas | 23.7 |
| AC219 | primary | pancreas | 31.2 |
| AC221 | primary | pancreas | 27.3 |
| AC224 | primary | pancreas | 33.4 |
| AC226 | primary | pancreas | 28.5 |
| AC227 | primary | pancreas | 25.6 |
| AC231 | primary | pancreas | 27.4 |
| AC233 | primary | pancreas | 28.2 |
| AC234 | primary | pancreas | 30.8 |
| AC235 | liver met | pancreas | 28.5 |
| AC236 | primary | small intestine | 30.1 |
| AC249 | liver met | pancreas | 28.7 |

TABLE 1-continued

EP-NET profiled samples. Mapper reads in millions.

| SampleID | Type | Tissue Origin | Mapped Reads |
|---|---|---|---|
| AC255 | liver met | pancreas | 34.8 |
| AC270 | liver met | small intestine | 30.2 |
| AC271 | liver met | small intestine | 40.3 |
| AC273 | liver met | small intestine | 32.6 |
| AC276 | liver met | pancreas | 28.9 |
| AC277 | liver met | small intestine | 1.3 |
| AC279 | liver met | pancreas | 23.7 |
| AC281 | liver met | small intestine | 30.6 |
| AC282 | liver met | pancreas | 29.5 |
| AC283 | liver met | small intestine | 29.4 |
| AC286 | liver met | small intestine | 32.3 |
| AC288 | liver met | small intestine | 32.8 |
| AC291 | liver met | pancreas | 35.2 |
| AC292 | liver met | pancreas | 34.3 |
| AC300 | liver met | small intestine | 29 |
| AC301 | liver met | small intestine | 23.4 |
| AC302 | liver met | pancreas | 32.3 |
| AC305 | liver met | pancreas | 29.5 |
| AC309 | liver met | pancreas | 37.5 |
| AC310 | liver met | pancreas | 30.6 |
| AC312 | liver met | pancreas | 25.2 |
| AC314 | liver met | small intestine | 25.8 |
| AC315 | liver met | small intestine | 30.9 |
| AC316 | liver met | small intestine | 34.3 |
| AC318 | liver met | pancreas | 20.1 |
| AC319 | liver met | small intestine | 30.9 |
| AC322 | primary | pancreas | 23.2 |
| AC323 | primary | pancreas | 25.9 |
| AC325 | primary | pancreas | 24.5 |
| AC326 | primary | pancreas | 24 |
| AC328 | primary | pancreas | 29.2 |
| AC329 | primary | pancreas | 28.9 |
| AC333 | primary | pancreas | 35.6 |
| AC337 | primary | pancreas | 30.3 |
| AC339 | primary | pancreas | 25 |
| AC341 | primary | pancreas | 33.2 |
| AC343 | primary | pancreas | 30.7 |
| AC346 | primary | pancreas | 25.5 |
| AC347 | primary | pancreas | 28.8 |
| AC348 | primary | pancreas | 31.9 |
| AC350 | primary | pancreas | 23.2 |
| AC351 | primary | pancreas | 26.7 |
| AC355 | primary | pancreas | 34.2 |
| AC361 | primary | pancreas | 27.7 |
| AC363 | primary | pancreas | 32.5 |
| AC365 | primary | pancreas | 31.2 |
| AC380 | primary | pancreas | 29.4 |
| AC383 | primary | small intestine | 30.7 |
| AC384 | liver met | small intestine | 27.3 |
| AC385 | liver met | pancreas | 26.8 |
| AC58 | liver met | pancreas | 50.7 |
| AC60 | primary | small intestine | 38.8 |
| AC61 | liver met | small intestine | 43 |
| AC71 | liver met | pancreas | 32.1 |
| AC73 | liver met | pancreas | 32 |
| AC75 | liver met | small intestine | 31.1 |
| AC79 | liver met | small intestine | 25.5 |
| AC87 | liver met | pancreas | 32.6 |
| AC89 | liver met | pancreas | 32.8 |
| AC99 | primary | small intestine | 27.8 |
| AC244 | liver met | small intestine | 33.6 |
| AC248 | liver met | small intestine | 30.3 |
| AC252 | liver met | small intestine | 31.3 |
| AC254 | liver met | pancreas | 30.2 |
| AC256 | liver met | pancreas | 28.4 |
| AC257 | liver met | pancreas | 40.2 |
| AC258 | liver met | pancreas | 30.9 |
| AC259 | liver met | small intestine | 29 |
| AC262 | liver met | small intestine | 29.2 |
| AC263 | liver met | small intestine | 30 |
| AC267 | liver met | small intestine | 28.3 |
| AC268 | liver met | small intestine | 32.3 |
| AC269 | liver met | pancreas | 29.7 |
| AC388 | primary | small intestine | 27.9 |
| AC389 | primary | small intestine | 36.8 |
| AC391 | primary | pancreas | 24 |

TABLE 1-continued

EP-NET profiled samples. Mapper reads in millions.

| SampleID | Type | Tissue Origin | Mapped Reads |
|---|---|---|---|
| AC392 | primary | small intestine | 29.5 |
| AC393 | primary | pancreas | 34.7 |
| AC395 | primary | small intestine | 30 |
| AA397 | primary | pancreas | 43.1 |
| AC398 | primary | pancreas | 19 |
| AC399 | primary | pancreas | 19.5 |
| AC400 | primary | pancreas | 25.8 |
| AC403 | primary | pancreas | 23.3 |
| AC405 | primary | pancreas | 25.9 |
| AC408 | primary | pancreas | 26.8 |
| AC409 | liver met | pancreas | 26.3 |
| AC410 | liver met | pancreas | 19.8 |
| AC411 | primary | pancreas | 18.1 |
| AC412 | primary | pancreas | 34.2 |
| AC417 | primary | small intestine | 21.9 |
| AC422 | primary | pancreas | 32.5 |
| AC425 | primary | pancreas | 20.8 |
| AC429 | primary | pancreas | 30.5 |
| AC430 | primary | small intestine | 32.9 |
| AC431 | liver met | pancreas | 28.4 |
| AC462 | primary | pancreas | 27.6 |
| AC468 | primary | small intestine | 26.6 |
| AC472 | primary | pancreas | 30.9 |
| AC473 | primary | pancreas | 30 |
| AC474 | primary | pancreas | 28.8 |
| AC480 | primary | small intestine | 21.3 |
| AC483 | primary | pancreas | 20.8 |
| AC484 | primary | pancreas | 22 |
| AC485 | primary | pancreas | 22.4 |
| AC486 | primary | pancreas | 26.7 |
| AC487 | primary | pancreas | 30.1 |
| AC488 | primary | pancreas | 33.3 |
| AC489 | primary | pancreas | 28.1 |
| AC490 | primary | small intestine | 27.2 |
| AC494 | lymphnode m | small intestine | 27.5 |
| AC495 | lymphnode m | small intestine | 27.1 |
| AC496 | primary | small intestine | 28.7 |
| AC497 | primary | small intestine | 30.4 |
| AC498 | lymphnode m | small intestine | 28.3 |
| AC499 | liver met | pancreas | 31.7 |
| AC500 | liver met | pancreas | 31.9 |
| AC539 | primary | small intestine | 28.8 |
| AC540 | primary | small intestine | 35.2 |
| AC541 | primary | small intestine | 27 |
| AC542 | primary | small intestine | 26.6 |
| AC543 | primary | small intestine | 29 |
| AC603 | primary | small intestine | 31.3 |
| AC604 | primary | pancreas | 30.9 |
| AC606 | primary | small intestine | 21.1 |
| AC607 | primary | pancreas | 30.7 |
| AC608 | primary | pancreas | 15.4 |
| AC609 | mesenteric m | small intestine | 28.6 |
| AC610 | lymphnode m | small intestine | 27.7 |
| AC611 | lymphnode m | small intestine | 32.3 |
| AC612 | primary | small intestine | 22.7 |
| AC577 | primary | rectum | 158.2 |
| AC578 | lymphnode m | rectum | 156.2 |
| AC579 | lymphnode m | rectum | 178.1 |
| AC576 | lymphnode m | small intestine | 18.7 |
| AC630 | primary | small intestine | 23.1 |
| AC631 | primary | small intestine | 18.6 |
| AC632 | lymphnode m | small intestine | 19.4 |
| AC633 | lymphnode m | small intestine | 13.9 |
| AC636 | liver met | rectum | 94.2 |
| AC646 | primary | small intestine | 32.3 |
| AC652 | lymphnode m | rectum | 52.1 |

Assembling an EP-NET Specific Regulatory Model:

The ability to identify MR proteins depends on the availability of accurate models of tissue-specific regulation, representing both direct targets of transcription factors (TF) and least-indirect targets of signaling proteins (SP). It has been shown that both can be effectively inferred by analyzing large, tumor-specific gene expression profile datasets using the Algorithm for the Accurate Reconstruction of Cellular Networks (ARACNe)[19,20], as supported by extensive experimental validation assays[9,10,17,21].

ARACNe analysis of the 211 EP-NET RNASeq profiles produced a tumor-specific regulatory network (interactome) comprising 571,499 regulatory interactions between 5,631 regulatory proteins over 20,136 target genes. Regulator proteins include 1,785 TFs and 3,846 SPs. This network was then used both to assess protein activity on an individual sample basis, for optimal cluster analysis, as well as to elucidate novel master regulators (MRs) of tumor progression.

Figure 11:
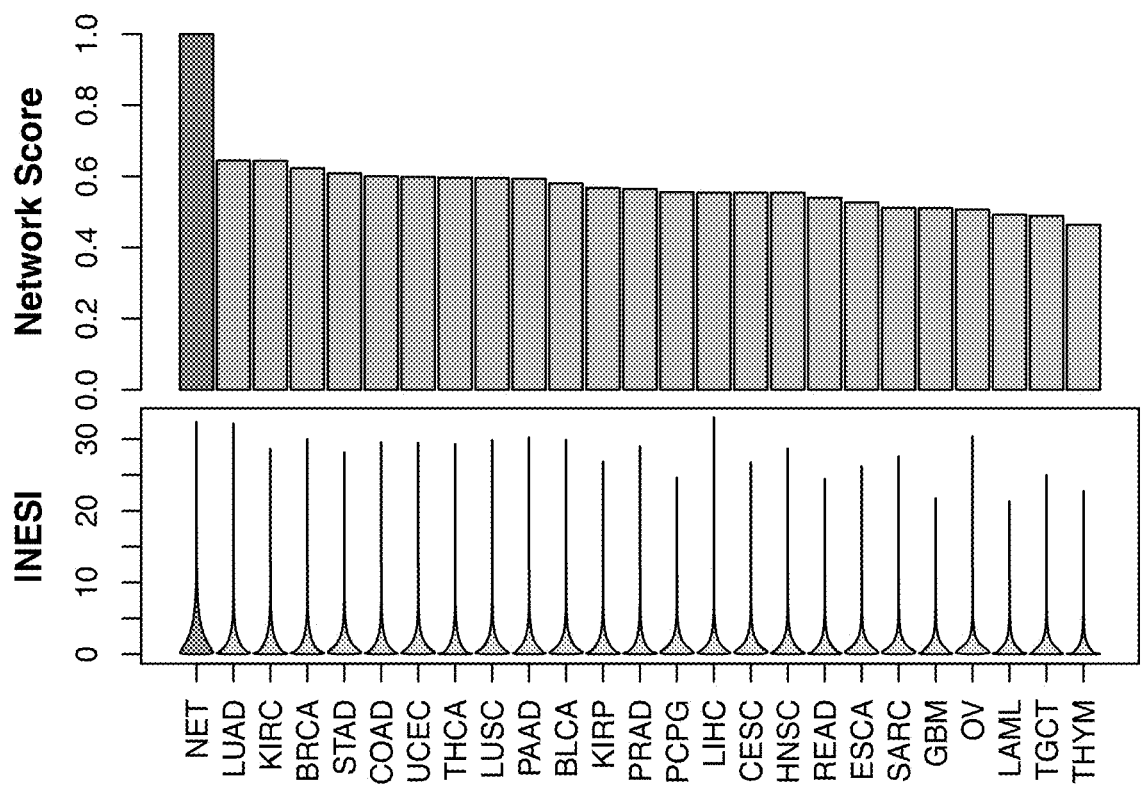
FIG. 11 depicts interactome reliability as models for EP-NET. Violin plot showing the probability density for the absolute normalized enrichment score (|NES|) and integrated Network Score computed as the area over the |NES| cumulative probability (See FIGS. 13A and 13B). NES was computed by VIPER for 211 EP-NET samples and all the regulatory proteins represented in the 25 evaluated interactomes (see Table 2)

Additional evaluation of the ARACNe inferred interactome confirmed that it is highly relevant for the analysis of EP-NET specific samples and that it is substantially distinct from other interactomes previously generated and validated, which would not have been appropriate for the analyses discussed below (see FIG. 12). When the network model is not representative of tissue-specific regulation, the master regulator analysis produces very few and barely significant results. Here, the EP-NET interactome produced the strongest enrichment for 211 EP-NET signatures when compared to 24 additional interactomes (Table 2 and FIG. 11), indicating that EP-NET is the best interactome, among all 25 tested ones, as a model for EP-NET context-specific transcriptional regulation.

TABLE 2

Interactomes

| Acronym | Tumor Type | Samples | Regulators | Targets | Interactions |
|---|---|---|---|---|---|
| BRCA | Breast carcinoma | 1,100 | 6,054 | 19,359 | 331,919 |
| UCEC | Uterine corpus endometrial carcinoma | 546 | 6,055 | 19,716 | 469,845 |
| KIRC | Kidney renal clear cell carcinoma | 534 | 6,054 | 19,843 | 350,478 |
| HNSC | Head and neck carcinoma | 522 | 6,055 | 19,772 | 423,104 |
| LUAD | Lung adenocarcinoma | 517 | 6,055 | 19,742 | 399,513 |
| THCA | Thyroid carcinoma | 509 | 6,053 | 19,861 | 317,582 |
| LUSC | Lung squamous cell carcinoma | 501 | 6,054 | 19,741 | 455,032 |
| PRAD | Prostate adenocarcinoma | 498 | 6,053 | 19,820 | 330,922 |
| COAD | Colon adenocarcinoma | 459 | 6,056 | 19,820 | 413,789 |
| BLCA | Bladder urothelial carcinoma | 408 | 6,054 | 19,785 | 489,101 |
| LIHC | Liver hepatocellular carcinoma | 373 | 6,056 | 19,829 | 469,922 |
| CESC | Cervical carcinoma | 306 | 6,056 | 19,839 | 583,961 |
| OV | Ovarian carcinoma | 299 | 6,007 | 19,140 | 647,358 |
| KIRP | Kidney renal papillary cell carcinoma | 291 | 6,055 | 19,858 | 452,653 |

TABLE 2-continued

Interactomes

| Acronym | Tumor Type | Samples | Regulators | Targets | Interactions |
|---|---|---|---|---|---|
| NET | Neuroendocrine tumor | 211 | 5,631 | 20,136 | 571,499 |
| STAD | Stomach adenocarcinoma | 274 | 6,056 | 21,663 | 561,858 |
| SARC | Sarcoma | 263 | 6,112 | 20,479 | 526,591 |
| ESCA | Esophageal carcinoma | 185 | 5,951 | 18,679 | 529,286 |
| PCPG | Pheochromocytoma and paraganglioma | 184 | 6,056 | 19,861 | 603,617 |
| LAML | Acute myeloid leukemia | 179 | 6,007 | 19,269 | 531,535 |
| PAAD | Pancreatic adenocarcinoma | 179 | 6,056 | 19,858 | 520,756 |
| READ | Rectum adenocarcinoma | 167 | 6,056 | 19,856 | 557,911 |
| GBM | Glioblastoma multiforme | 166 | 6,056 | 19,858 | 563,850 |
| TGCT | Testicular germ cell tumor | 156 | 6,056 | 19,860 | 432,621 |
| THYM | Thymoma | 120 | 6,056 | 19,862 | 387,923 |

Figure 12A:
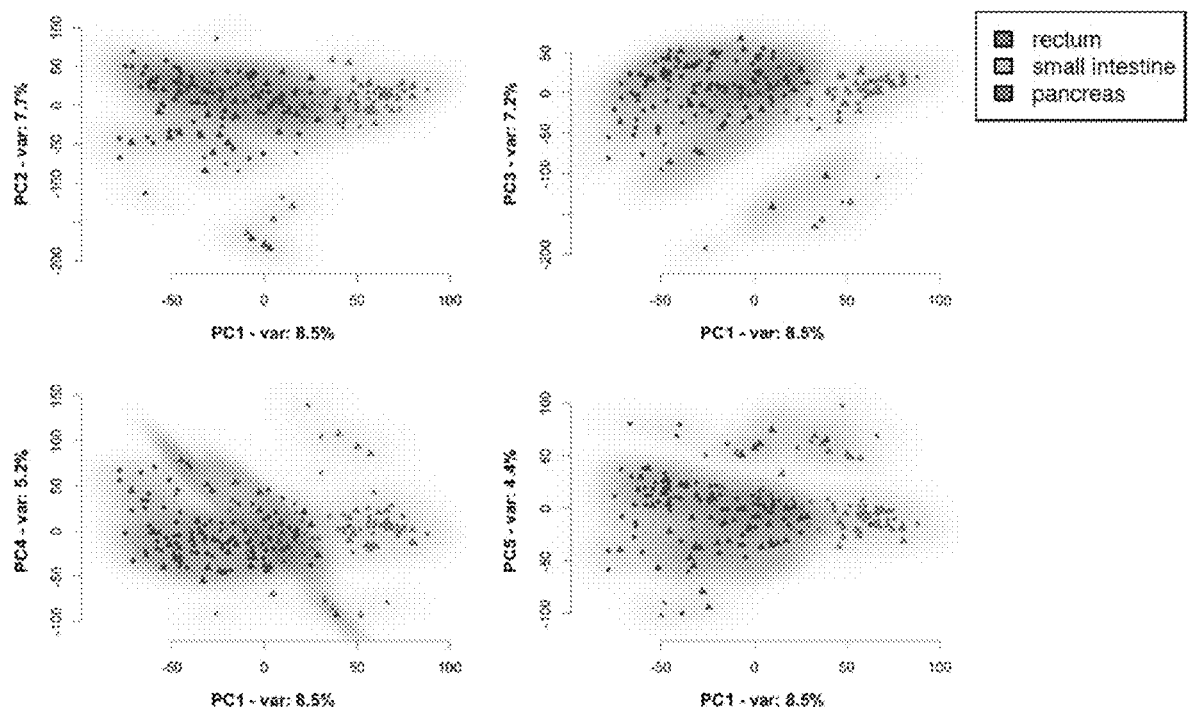
FIGS. 12A-12C depict unsupervised analysis of 211 EP-NET samples. (A) Scatter-plots showing the first 5 principal components, capturing 35% of the variance for 211 EP-NET expression profiles. (B) 2D-tSNE projection for the expression data. (C) 2D-tSNE projection of the VIPER-inferred protein activity for 211 EP-NET samples.
Figure 12B:
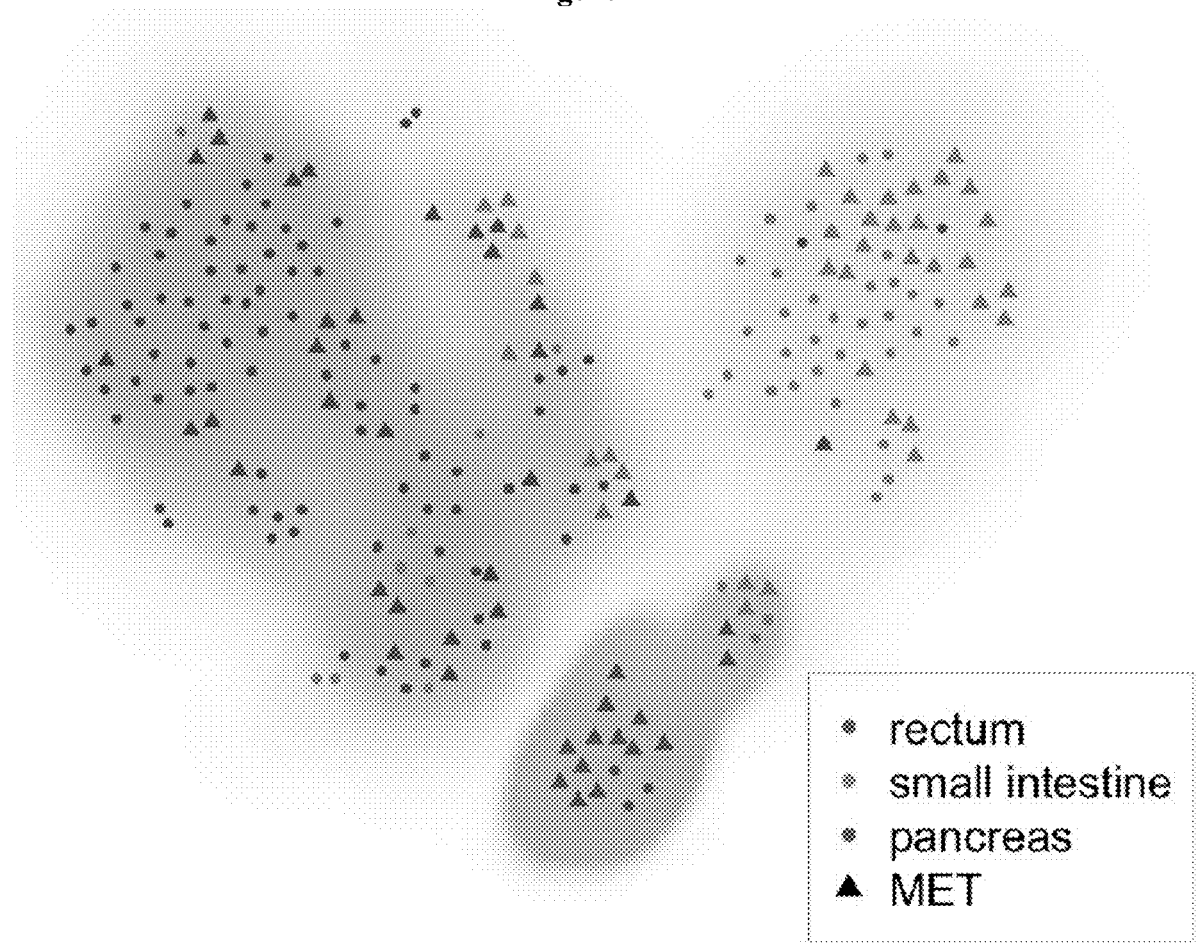
Figure 12C:
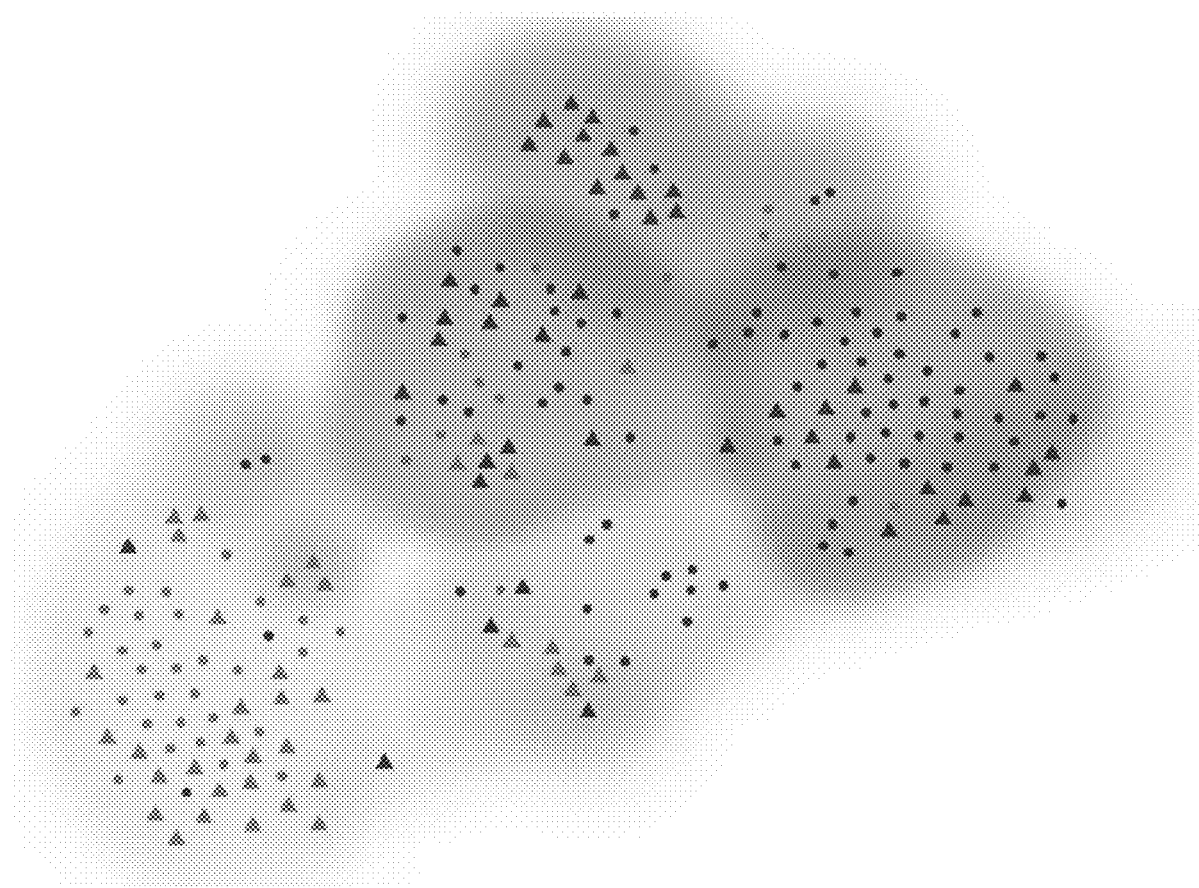

Identification of EP-NET Molecular Subtypes:

Unsupervised analysis of EP-NET profiles suggests a strong tissue-of-origin component present in the transcriptome. Specifically, analysis of the first 5 principal components, based on singular value decomposition (SVD) analysis of the transcriptional data, captured 33% of the total sample variance and partially clustered with primary tumor site, regardless of whether samples represented primary, lymph node, or liver metastases (FIG. 12A). This observation was further confirmed based on a t-Distributed Stochastic Neighbor Embedding (t-SNE) projection of EP-NET transcriptomes in two dimensions (FIG. 12B). FIG. 12A depicts scatter-plots showing the first 5 principal components, capturing 35% of the variance for 211 EP-NET expression profiles. The tissue of origin is indicated by different colors. Primary tumors are shown with circles, while METs are shown with triangles. FIG. 12B depicts 2D-tSNE projection for the expression data. Different colors indicate the different tissue of origin. FIG. 12C depicts 2D-tSNE projection of the VIPER-inferred protein activity for 211 EP-NET samples. The color of the symbols indicates tissue of origin, their shape indicates their status as primary tumor (circles) or METs (triangles). The color of the clouds indicate the cluster membership according to FIG. 7B.

Figure 7A:
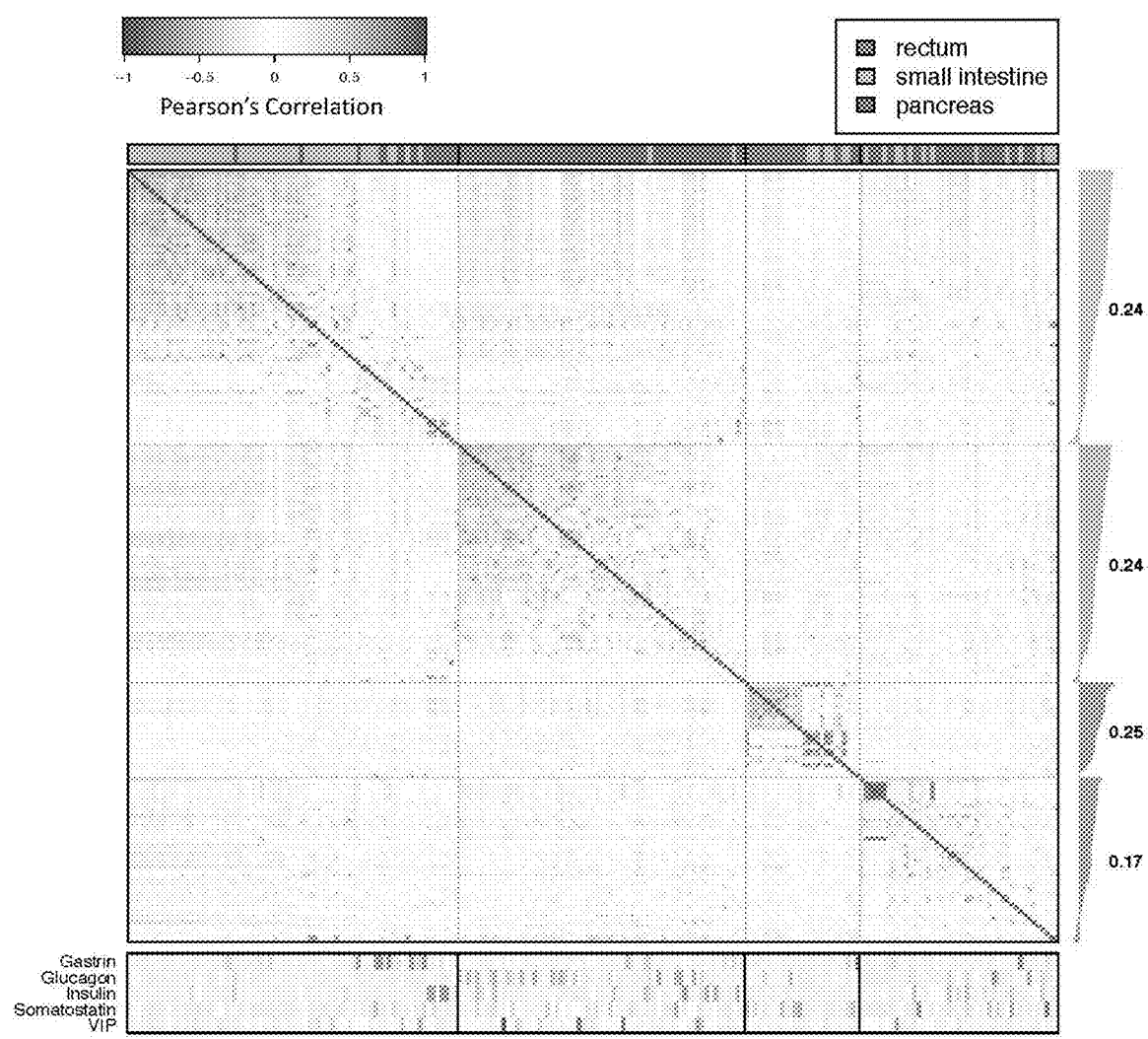
FIGS. 7A and 7B depict EP-NET molecular subtypes. (A) Unsupervised cluster analysis of 211 EP-NET samples based on their gene expression profile. (B) Unsupervised cluster analysis based on the VIPER-inferred protein activity for 5,578 regulatory proteins.
Figure 13A:
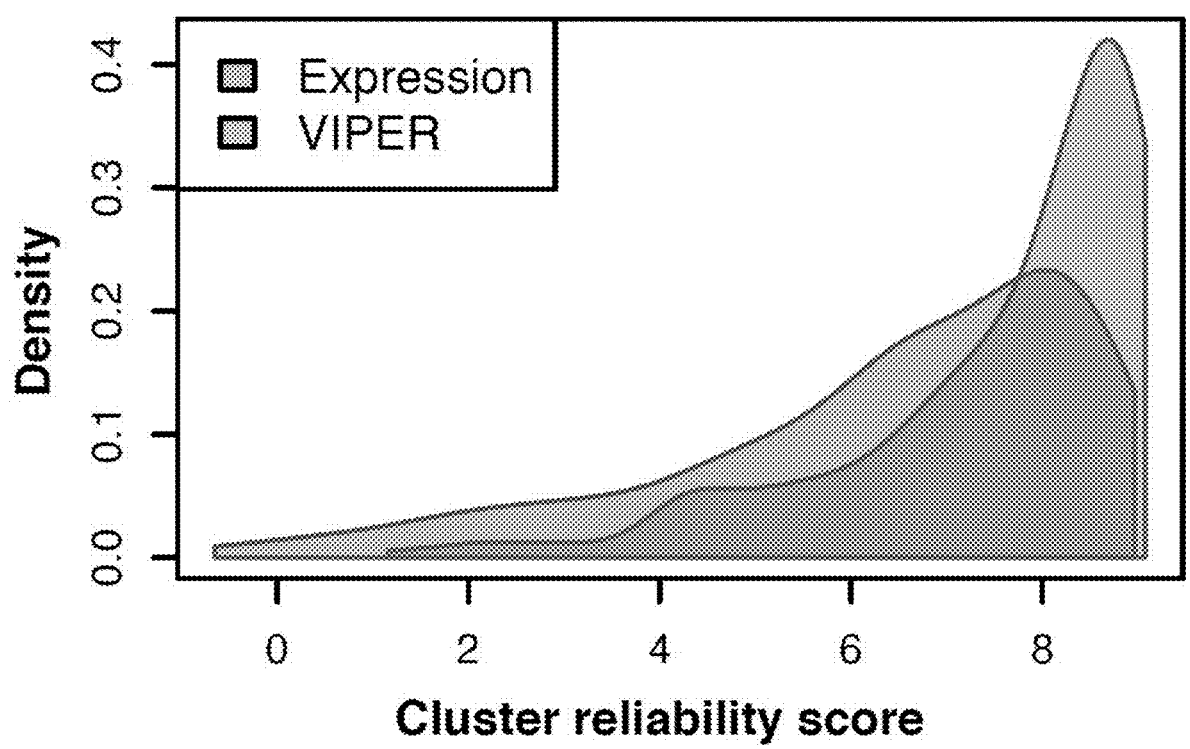
FIGS. 13A-13G depict cluster reliability. (A) Probability density plot for the cluster reliability estimated from the expression profiles and VIPER-inferred protein activity profiles for 211 EP-NET samples (see FIG. 13D). (B) Integrated reliability score for the complete cluster structure computed as the area over the cumulative probability curve. (C) Integrated reliability score for different cluster structures (different number of clusters) for the consensus cluster of 211 EP-NET expression (red) or VIPER-inferred protein activity profiles (blue). (D) Cluster reliability score for 211 EP-NET expression and VIPER-inferred protein activity profiles after consensus clustering in 4 and 5 clusters, respectively. (E and F) Cluster reliability (E) and silhouette score (F) for each sample from the 4 clusters structure based on expression and the 5 clusters structure based on VIPER-inferred protein activity data. (G) Cluster membership for the H-STS xenograft model.
Figure 13B:
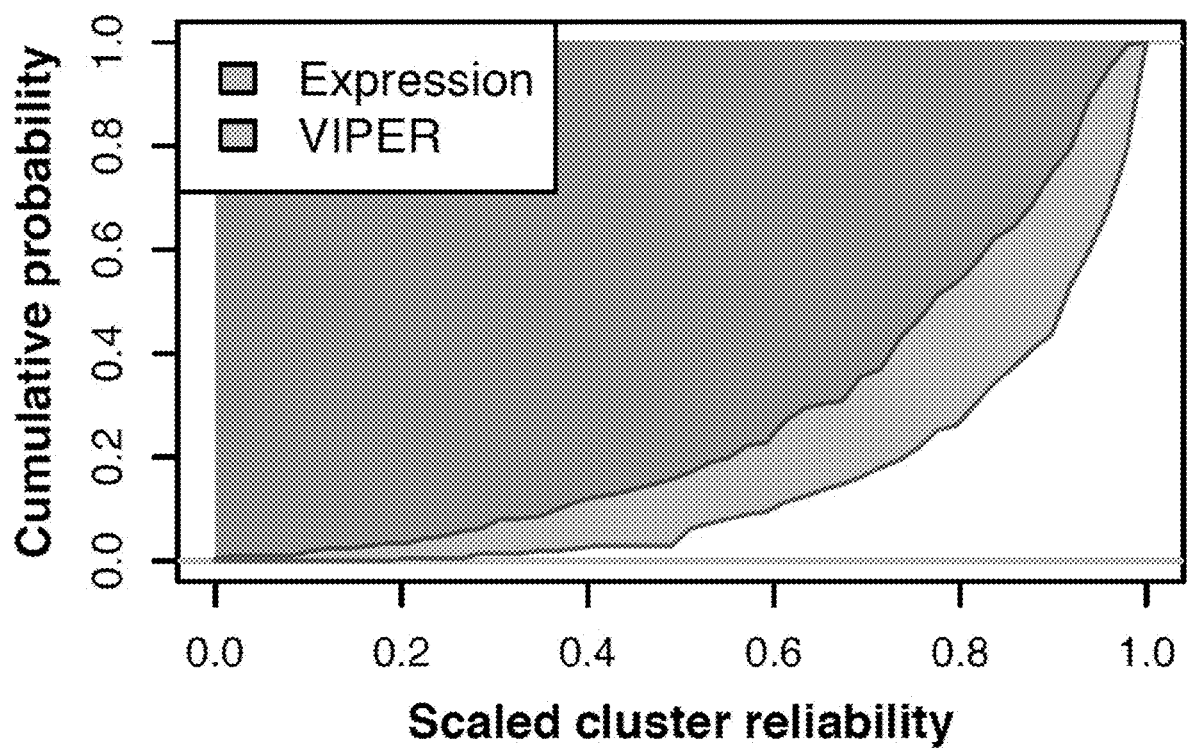
Figure 13C:
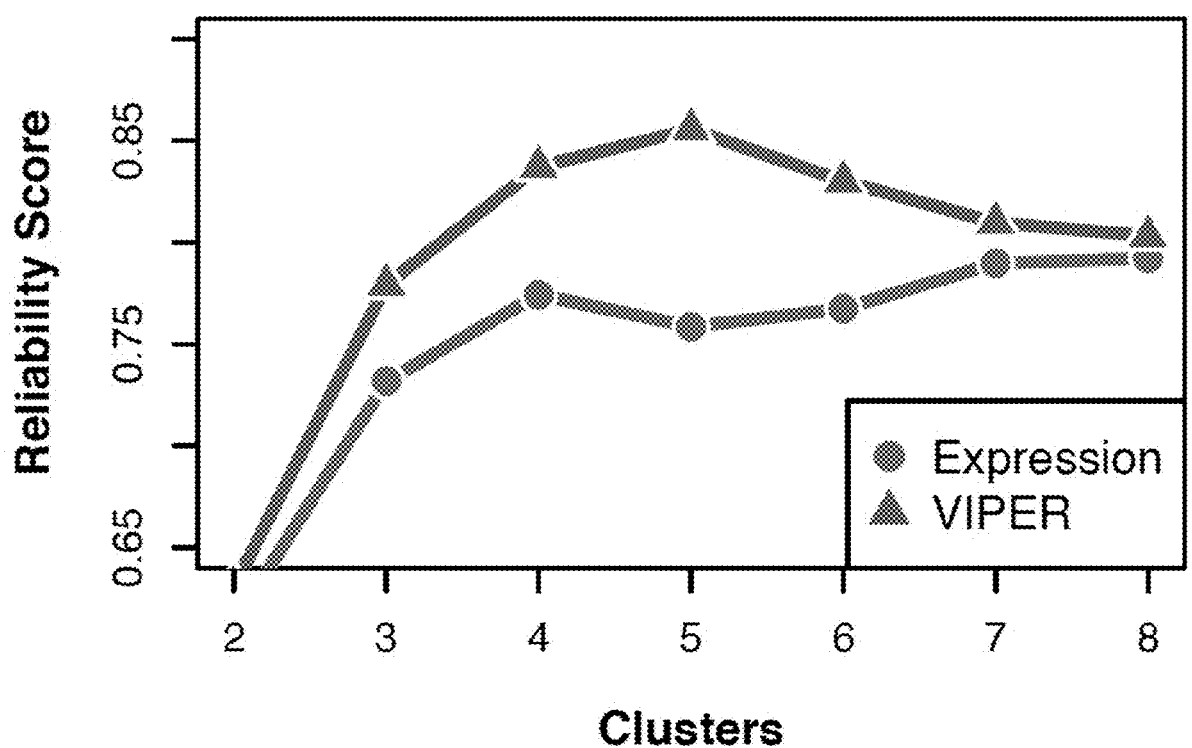

Consistently, Partitioning Around Medoids (PAM)-based consensus clustering, followed by cluster reliability analysis, suggested an optimal partitioning of the samples in four clusters that also partially co-segregated with primary tumor site (FIG. 13C and FIG. 7A). Specifically, clusters 1-3 were highly enriched in SI-NET, Pan-NET and Rec-NET samples, respectively, while clusters 4 included samples from SI-NET and Pan-NET (FIG. 7A).

Figure 13D:
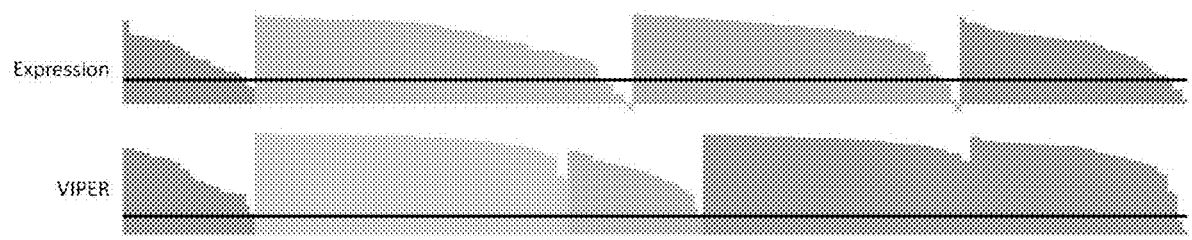
Figure 13E:
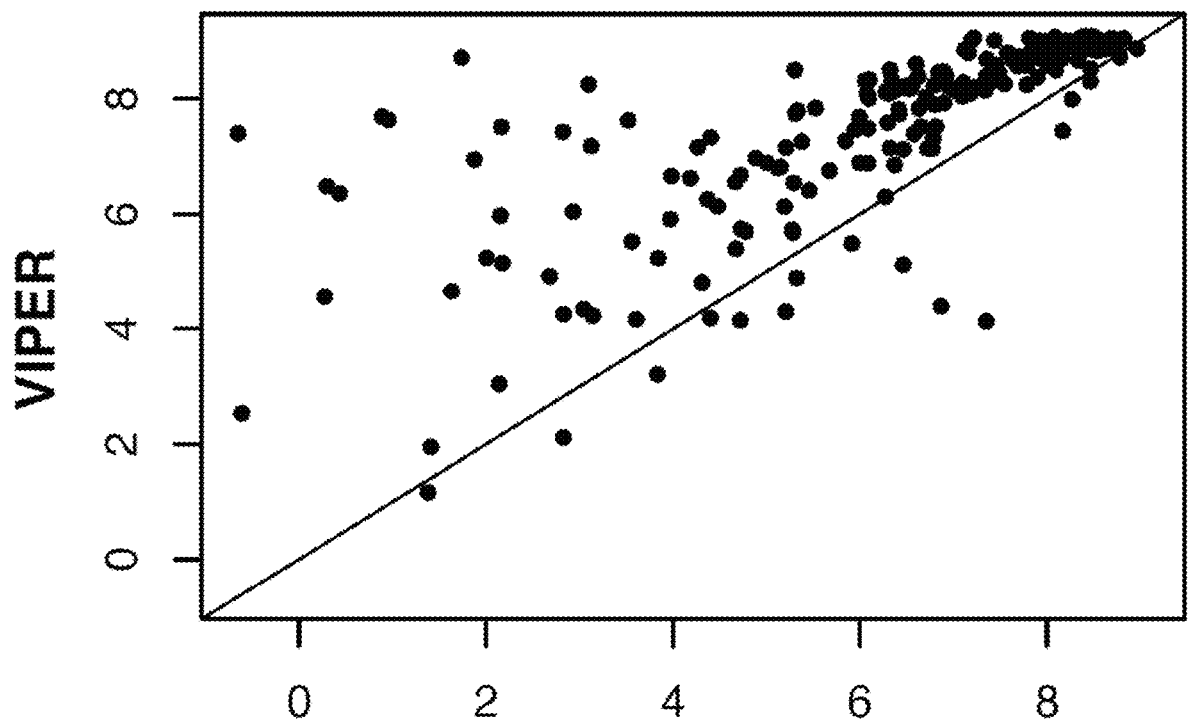
Figure 13F:
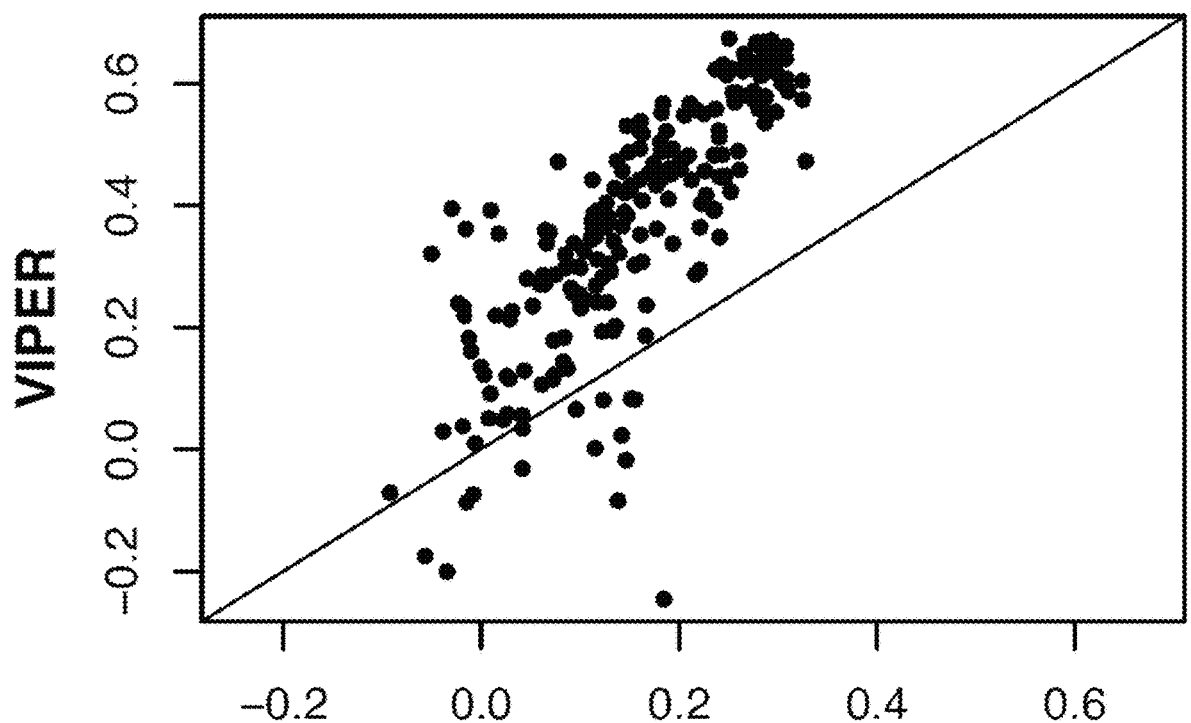
Figure 13G:
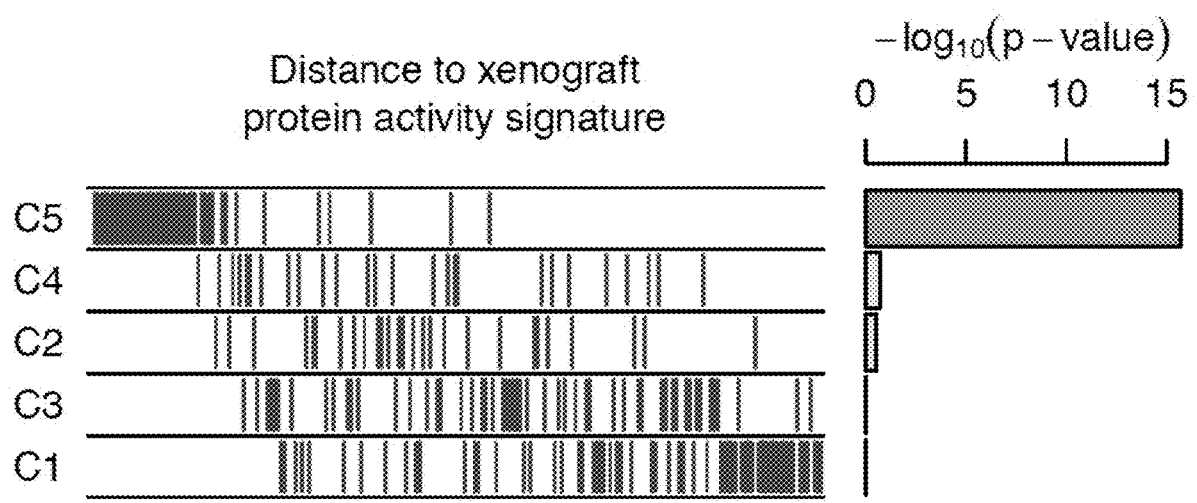
Figure 14A:
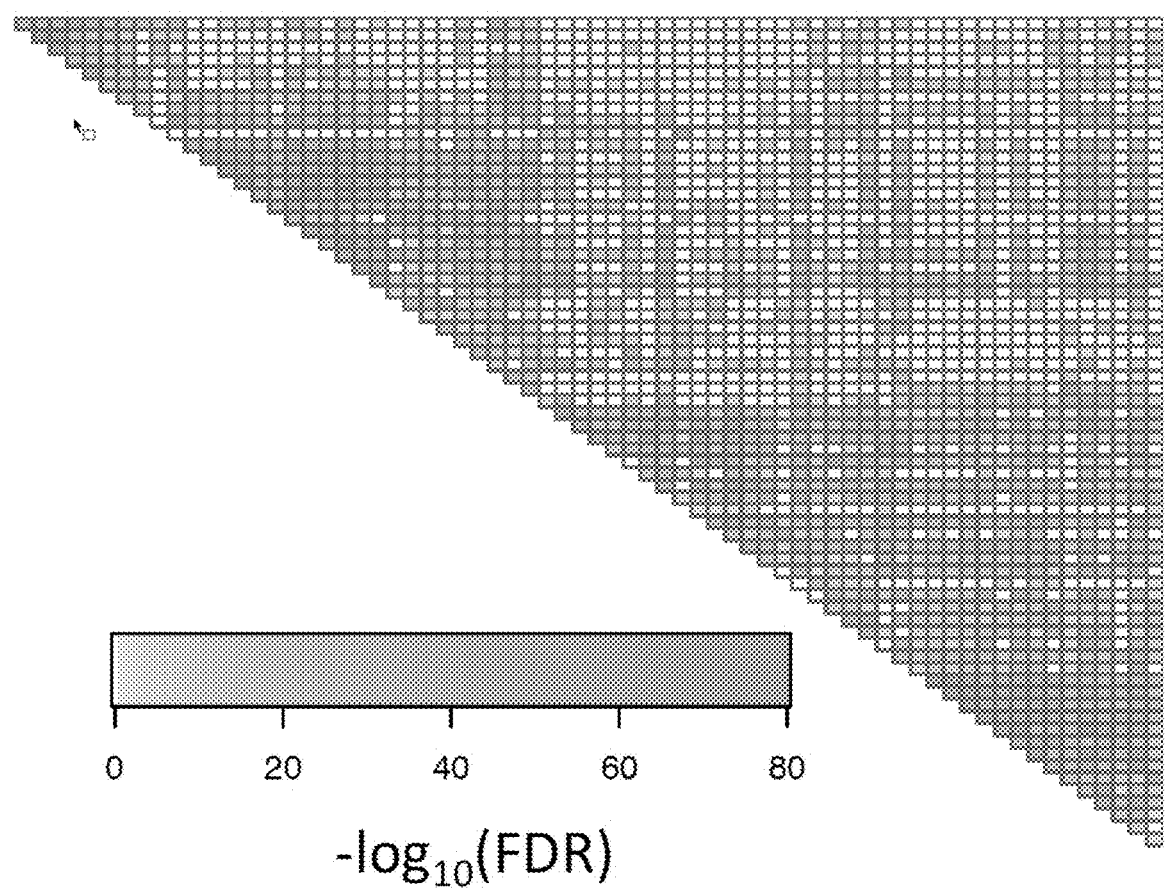
FIGS. 14A and 14B depict metastatic progression MRs. (A) Conservation of the top 25 most activated and top 25 most inactivated MRs between 66 NET liver metastasis. (B) Optimal number of clusters based on the regulators of metastatic progression.
Figure 14B:
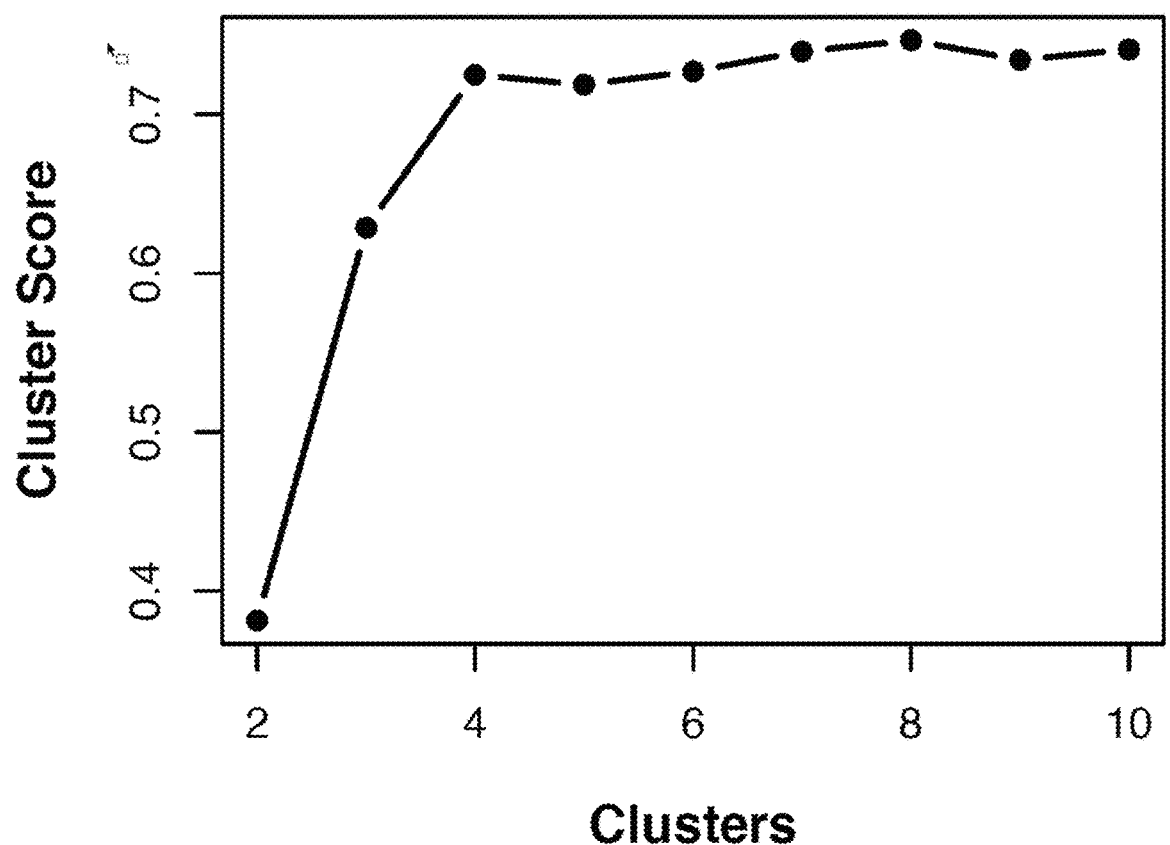

FIG. 13A depicts the probability density plot for the cluster reliability estimated from the expression profiles and VIPER-inferred protein activity profiles for 211 EP-NET samples (see FIG. 13D). FIG. 13B depicts integrated reliability score for the complete cluster structure computed as the area over the cumulative probability curve. FIG. 13C depicts integrated reliability score for different cluster structures (different number of clusters) for the consensus cluster of 211 EP-NET expression (red) or VIPER-inferred protein activity profiles (blue). FIG. 13D depicts cluster reliability score for 211 EP-NET expression and VIPER-inferred protein activity profiles after consensus clustering in 4 and 5 clusters, respectively. The horizontal black line indicates the threshold for FDR<0.01. FIGS. 13E and 13F depict cluster reliability (E) and silhouette score (F) for each sample from the 4 clusters structure based on expression and the 5 clusters structure based on VIPER-inferred protein activity data. FIG. 13G depicts cluster membership for the H-STS xenograft model. Shown is the enrichment of the samples from each of the 5 clusters on the distance to the xenograft model based on the correlation between protein activity signatures. Enrichment significance is shown as $-\log_{10}$ (p-value) by the bar-plot.

Protein activity, inferred from single-sample transcriptome readouts using VIPER, can be a more robust descriptor of cell state than gene expression[18]. The reason is three-fold. First, VIPER-inferred protein activity represents a more direct and mechanistic determinant of cell state, compared to gene expression; second, while individual gene expression measurements are quite noisy and poorly reproducible, VIPER infers protein activity from the expression of a large number (tens to hundreds) of its transcriptional targets (i.e., the protein's regulon), thus resulting in much higher accuracy and reproducibility[18]; third, bias and technical noise that is inconsistent with the regulatory model is effectively filtered out, thus effectively removing a major source of confounding data. The EP-NET interactome can be used to transform the 211 individual transcriptional profiles into equivalent protein-activity profiles for 5,578 of the regulator proteins represented in the network, using VIPER[18].

Figure 7B:
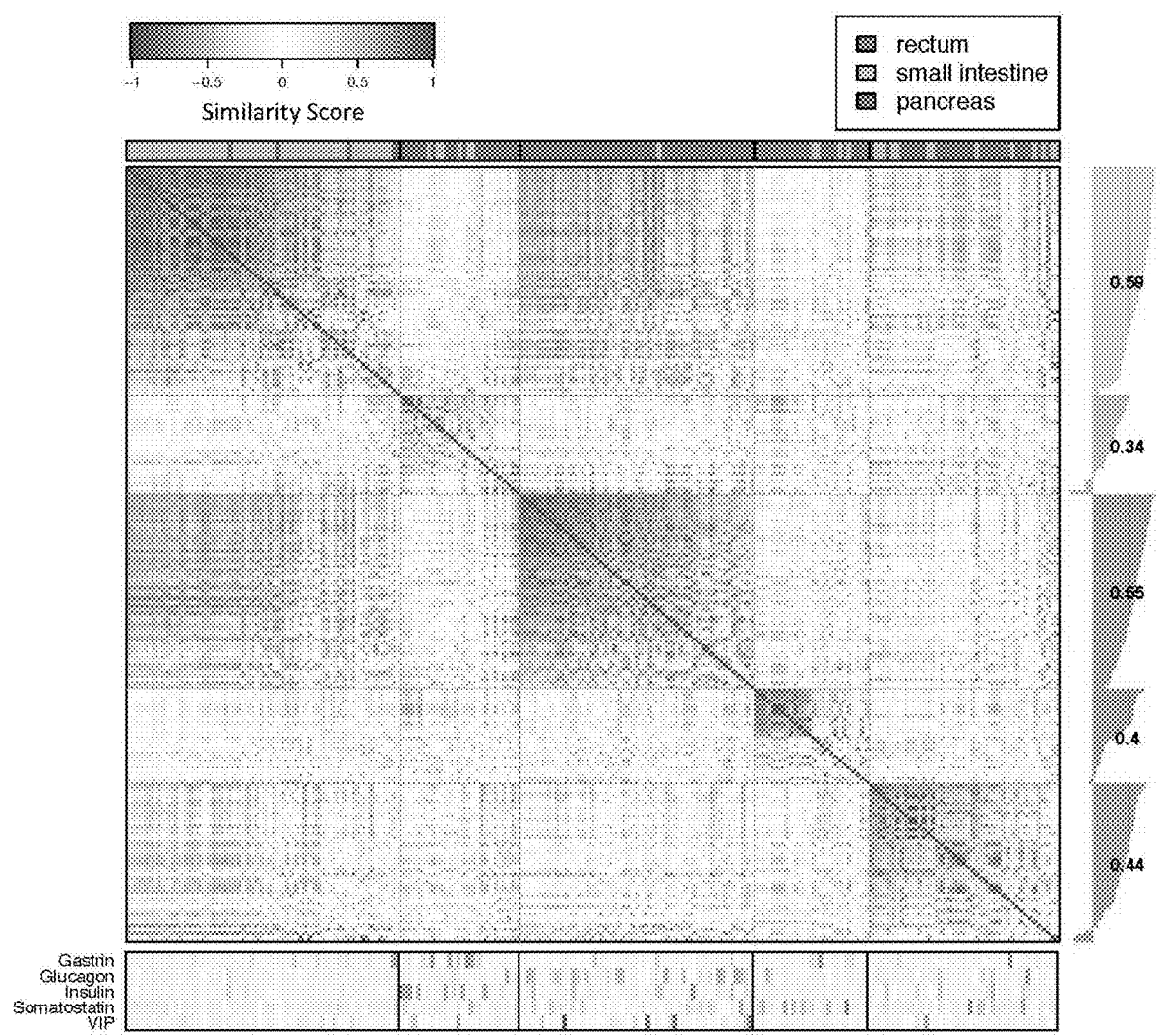

VIPER-inferred protein activity was effective in segregating samples according to tissue of origin. Both, unsupervised PAM-based consensus cluster analysis, and t-SNE projection of the protein-activity data into the two-dimensional space, identified 5 strongly distinct clusters representing molecularly distinct EP-NET subtypes (FIGS. 7B and 12C). These included a SI-NET specific cluster (C1: yellow), a Pan-NET specific cluster (C3, blue), a Rec-NET cluster (C4: red), and two heterogeneous clusters including mainly Pan-NET and SI-NET samples (C2: green and C5: purple), see FIGS. 7B and 12C. Same color scheme was used to represent samples belonging to these clusters in the t-SNE projection, thus highlighting an essentially equivalent clustering structure by both unsupervised analysis approaches (FIGS. 7B and 12C). FIG. 7A shows the results of an unsupervised cluster analysis of 211 EP-NET samples based on their gene expression profile. The heatmap shows the weighted Pearson's correlation coefficient. Samples were partitioned in 4 clusters and sorted according to their silhouette score (indicated by the color bars on the right of the heatmap). Each cluster average silhouette score is indicated by numbers. The tissue of origin is indicated in the top horizontal bar: rectum (red), small intestine (green) and pancreas (blue). The expression level (RPKM) for gastrin, glucagon, insulin, somatostatin and VIP is indicated by the bottom heatmap. FIG. 7B shows the results of an unsupervised cluster analysis based on the VIPER-inferred protein activity for 5,578 regulatory proteins. The heatmap shows the scaled similarity score computed by the aREA technique.

Cluster reliability analysis confirmed that protein-activity based clusters significantly outperformed the noisier gene expression based clustering (FIGS. 13C-13F; $p<10^{-15}$, U-test). Besides the more reliable clusters obtained from protein activity, both clusters structures were remarkably similar (Adjusted Rand index: 0.57, $p<10^{-5}$ by permutation test). Interestingly, Pan-NET tumors were divided across three distinct clusters, consistent with potential cell of origin, including gastrinoma, insulinoma (green), glucagonoma (blue), and non-secretory pancreas-NETs (purple) (FIG. 7). These results clearly support a strong tissue-of-origin epigenetic memory in EP-NETs, independent of tumor stage.

Inference of MR Proteins of Metastatic Progression:

To identify Master Regulator proteins responsible for the metastatic progression (MET) phenotype, the EP-NET interactome can be interrogated with Gene Expression Signatures representing the cell state transition between primary tumors and hepatic metastases (MET-GES). Clinically, metastatic progression to the liver determines a transition to an intractable form of the disease, associated with poor prognosis. As previously shown, some of these MR proteins would represent critical tumor dependencies associated with the metastatic form of the disease, which can be targeted pharmacologically.

To directly account for the potential heterogeneity of tumor progression mechanisms, as well as to support the proposed patient-specific approach to elucidating MR dependencies and associated small molecule inhibitors, 69 metastatic samples were analyzed on an individual basis. Specifically, individual MET-GES signatures were generated by differential expression analysis of each hepatic metastasis sample in a cluster (i.e. C1-C5) against the average of all primary samples in that cluster (FIG. 7B). 3 of the 211 samples cannot be reliably clustered (cluster reliability FDR>0.01), including 1 pancreas and 2 small intestine primary tumors. These samples were not considered for further analysis. Individual MET-GES where then analyzed using VIPER, against the EP-NET interactome, to identify MR proteins responsible for directly regulating the change in gene expression repertoire during metastatic progression.

Figure 8A:
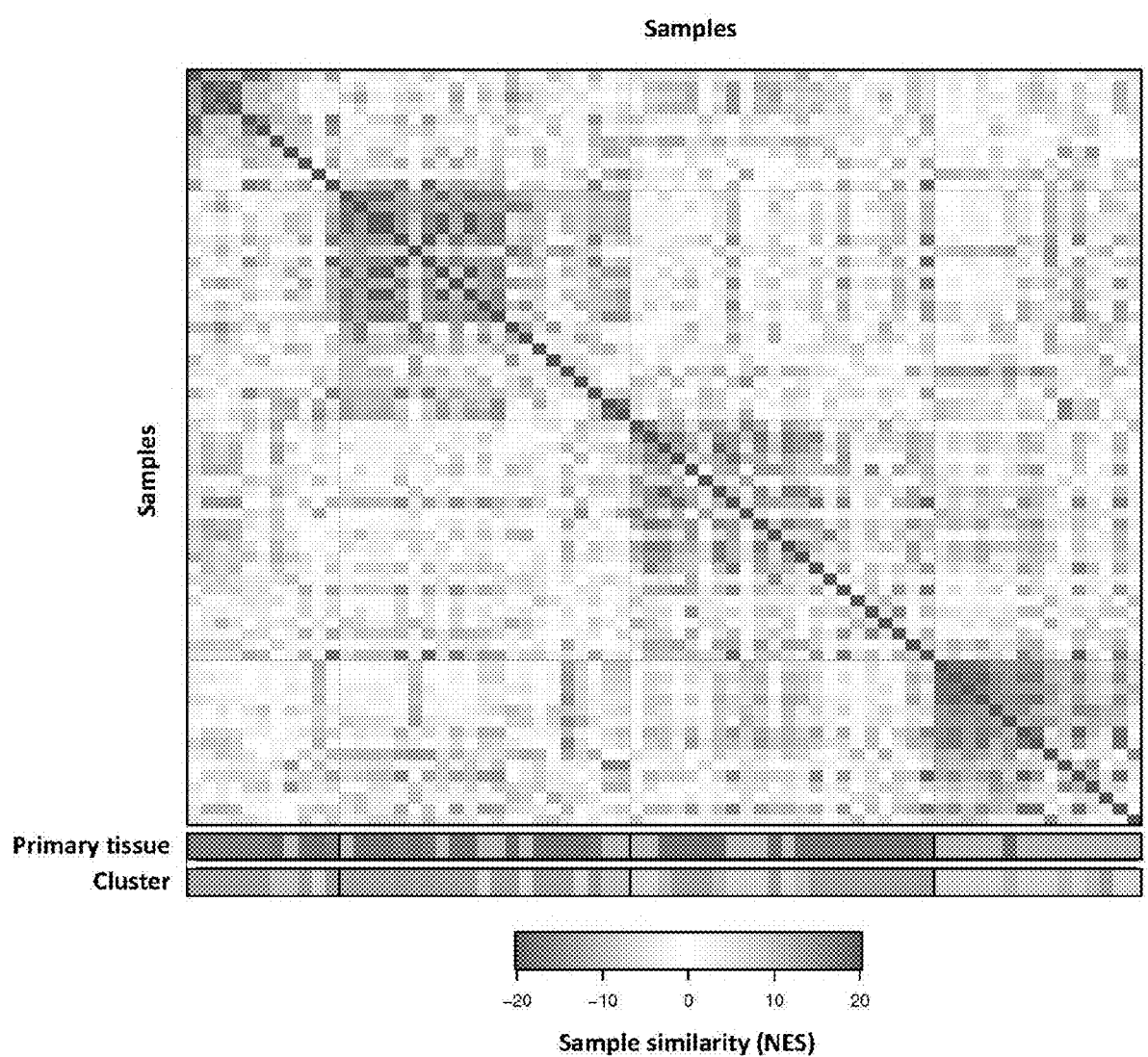
FIGS. 8A and 8B depict master regulators for the metastatic progression. (A) Heatmap showing the conservation of the top 50 most dysregulated proteins in association with liver metastasis between each possible sample pair. (B) Heatmap showing relative protein activity for the top 20 most dysregulated proteins from each of the four clusters.

Metastatic progression MRs were remarkably conserved both within and across the C1-C5 molecular clusters. Indeed, the top 25 most activated and 25 most inactivated MRs, as identified from each metastatic progression signature, were highly enriched in the overall ranking of VIPER-inferred protein activity from other MET-GES signatures. Specifically, 1,416 of the 2,346 possible metastatic sample pairs showed significant MR overlap (FDR<0.01) (FIGS. 8A and 12A).

Figure 8B:
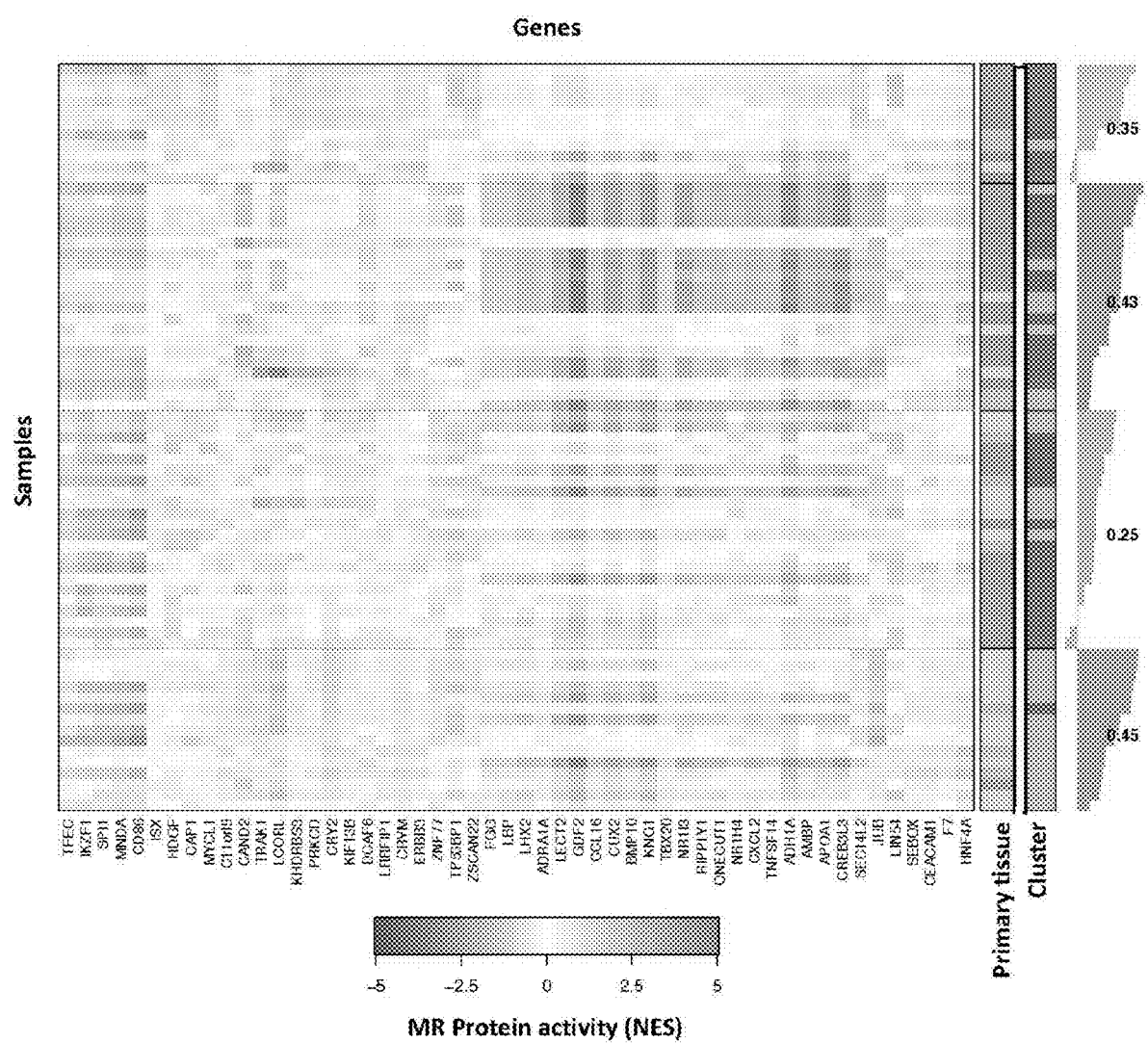

Unsupervised consensus cluster analysis supports the presence of four distinct clusters (MC1-MC4) representing highly conserved, yet distinct mechanisms of metastatic progression (FIG. 8A), each one sharing a large subset of common MRs (FIG. 8B). FIG. 8A depicts heatmap showing the conservation of the top 50 most dysregulated proteins in association with liver metastasis between each possible sample pair. Samples were partitioned in 4 clusters based on metastasis drivers conservation and sorted according to the silhouette score. The tissue of origin is indicated by the first color bar: rectum (red), small intestine (green) and pancreas (blue). The clusters corresponding to FIG. 7B are indicated with the same colors in the second color bar. FIG. 8B depicts heatmap showing relative protein activity for the top 20 most dysregulated proteins from each of the four clusters. Color bars on the right indicate tissue of origin and correspondence to the five clusters depicted in FIG. 7B. Single sample silhouette score and cluster average are indicated to the right of the plot.

Interestingly, when comparing the 5 molecular subtype clusters with the four tumor progression clusters, there was a very weak association between them, with most of the samples from C1 clustering in MC5, which was enriched in SI-NETs and most of samples from C4 falling in MC1, which was enriched in Rec-NETs. However, all three MC-clusters were composed of samples from different subtypes, supporting that the mechanisms of metastatic progression are largely decoupled from primary tumor site and subtype identity.

Selection of Appropriate In Vitro Models for MR Validation and Drug Profiling:

Experimental MR validation on an individual sample basis requires availability of appropriate in vitro and in vivo models. This is especially relevant to assess whether analysis of patient-derived samples can elucidate small molecule compounds that can abrogate tumor viability in vivo by inducing MR activity inversion (i.e., tumor checkpoint collapse). EP-NETs were characterized by the paucity of available high-fidelity models, including both cell lines and xenografts. Five cell lines derived from EP-NET patients that were previously characterized in the literature were considered and shown to present certain features, including expression of chromogranin A and somatostatin receptor II, representing the hallmark of these tumors. Specifically, three isogenic cell lines isolated from a single SI-NET patient including from the primary tumor (P-STS) were considered, from a lymph node metastasis (L-STS) and from a hepatic metastasis (H-STS)[22], an additional cell line isolated from a distinct SI-NET patient (KRJ-I)[23], and a cell line from a poorly differentiated adenocarcinoma of the caecum with neuroendocrine features (NCI-H716).

To assess the value of these cell lines as in vitro models for the individual patient metastases represented in the dataset, cell line-specific MET MRs analysis was performed by generating a MET-GES progression signature for each metastatic cell line against the P-STS cell line, as a representative of a primary tumor. A computation can be performed to determine whether each patient top 100 MRs were enriched in each cell line MRs activity signature by the aREA technique[18].

Figure 9A:
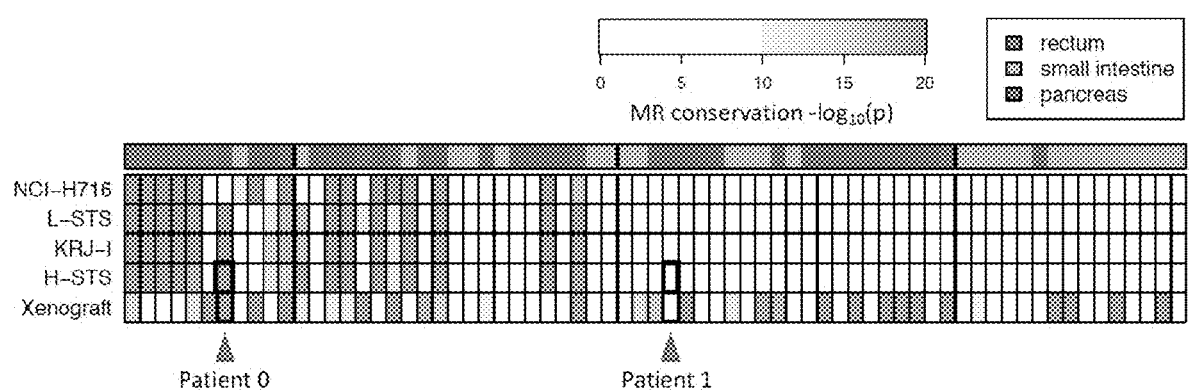
Figure 9B:
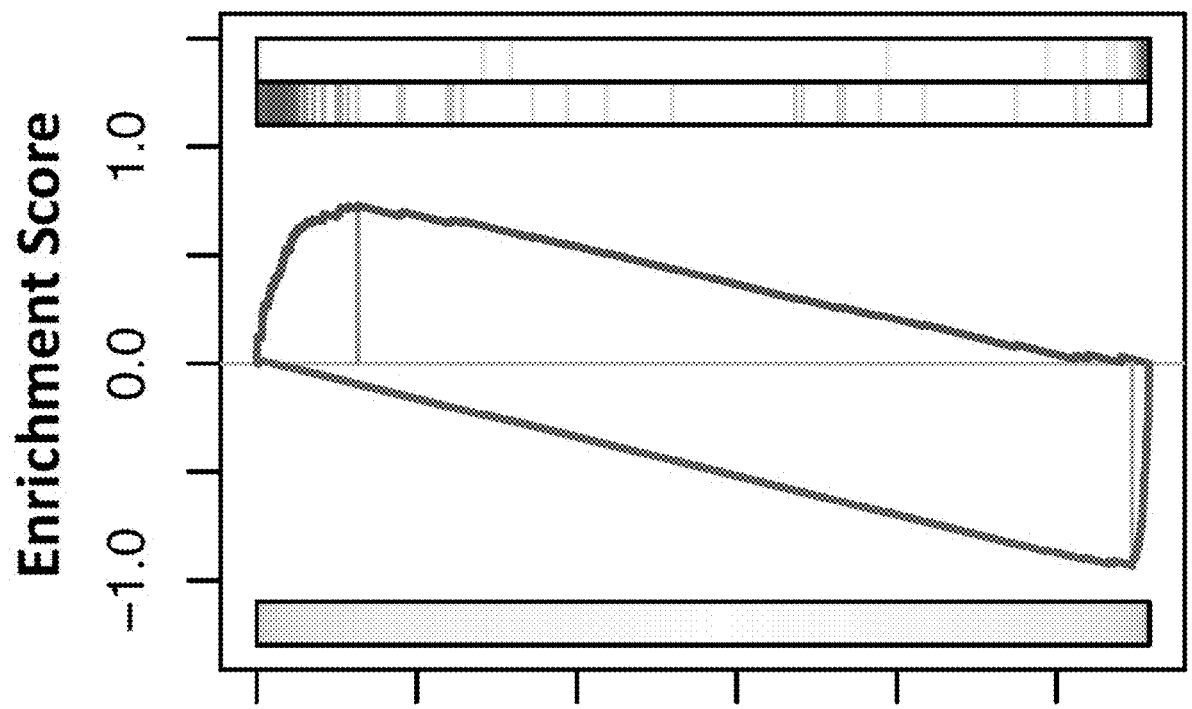

MRs for 20 of the 69 metastatic patient-derived samples were significantly recapitulated by the available EP-NET cell lines. H-STS cell line is of particular interest because it is derived from a metastatic lesion while the isogenic line P-STS was established form the primary NET tumor. H-STS recapitulated the MRs of 17 tumors (Bonferroni's adjusted $p<10^{-10}$, FIG. 9A). In particular, it recapitulated the MRs of a substantial majority of RE-NET samples (8/11, 73%), and of a few SI-NET (2/28, 7.1%) and Pan-NET (7/30, 23%) samples, including the MRs of one Pan-NET patient of interest (P0) on which the oncoTreat analysis is based (FIGS. 9A and 9B). One patient whose MRs were not properly recapitulated by the H-STS cell line was selected for comparison purposes (P1, FIG. 9C). FIG. 9A depicts enrichment of the top 100 most dysregulated proteins from each metastasis on each cell line and the H-STS xenograft model protein activity signature. The color bar on top of the plot indicates the tissue of origin for the primary tumor. The blue triangles indicate two Pan-NET metastasis (patient-0 and patient-1) for which a detailed plot of this analysis is shown in panels B through E. FIGS. 9B-9E depict the results of Gene Set Enrichment Analysis for the top 50 most activated and the top 50 most de-activated proteins in each selected metastasis on the protein activity signature of the H-STS cell line (B and C), and the H-STS xenograft model (D and E). Enrichment score for the de-activated (blue) and activate (red) proteins in the metastasis is shown by the curves. The top 50 most dysregulated proteins in the metastasis are indicated by vertical lines as projected on the H-STS and the xenograft protein activity signatures, which are indicated by the color scale on the bottom of the plot.

Figure 9D:
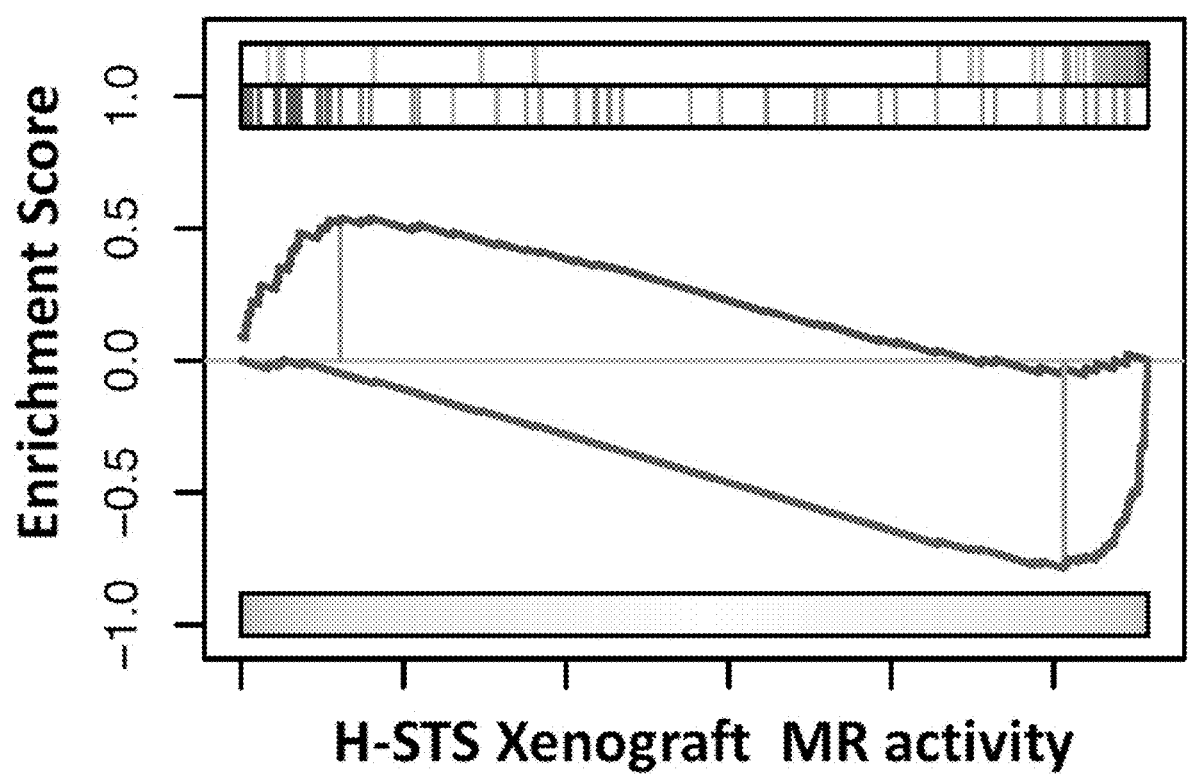
Figure 9E:
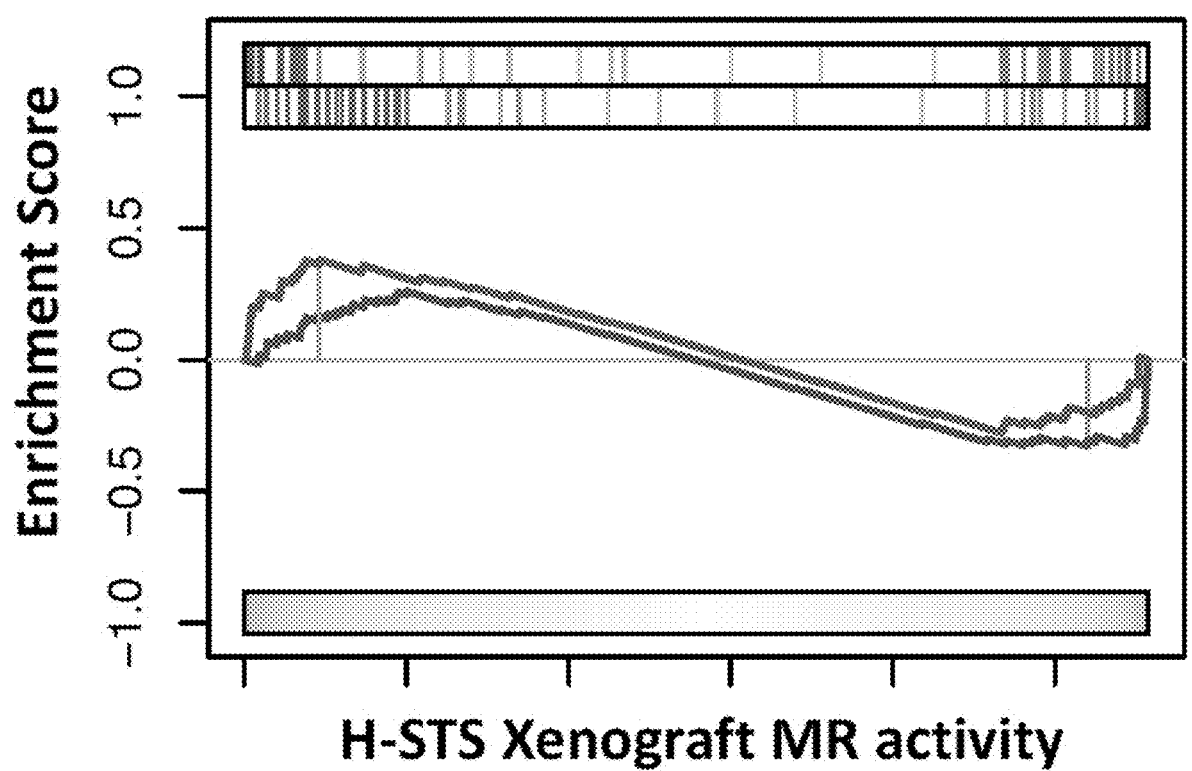

Transcriptome analysis of an H-STS xenograft model indicated a clear similarity to the molecular cluster C5 (purple, FIG. 13G). Interestingly, this xenograft model recapitulated the metastasis MRs of 32 of the 69 metastatic tumors, including 73% of the RE-NET (8 tumors), 32% of the SI-NET (9 tumors) and 50% of the Pan-NET (15 tumors) (FIGS. 9A, 9D and 9E).

Systematic Inference of MR Activity Inhibitors:

To identify candidate small molecule compounds capable of abrogating the MR activity signature driving metastatic progression, a library of 504 compounds previously screened at the Broad Institute, Cambridge, Mass., were interrogated for differential activity against a panel of 242 genomically characterized cancer cell lines (CCL), of which 354 had been previously published[6]. All 504 compounds were re-screened in the available neuroendocrine tumor cell lines, including H-STS, L-STS, P-STS, KRJ-I, and NCI-H716. The top 108 most differentially active compounds in NET-related cells compared to the other 242 CCL were selected, based on their differential activity on cell viability, as measured by the area under the dose response curve (AUC). Dose response curves for these compounds were repeated in the HTS facility at Columbia University and compared to those generated at the Broad. Overall, these studies presented remarkable overlap with an AUC Spearman correlation of 0.71 ($p=1\times10^{-10}$).

To assess the ability of these compounds to induce Tumor Checkpoint collapse (i.e., global inversion of patient-derived MR activity pattern), gene expression profiles were generated at 6 h and 24 h following perturbation of H-STS cells with two sub-lethal compound concentrations, the 72 h $IC_{20}$ and $\frac{1}{10}^{th}$ of that concentration in duplicate. The 24 h time point was considered more informative for long term response. These were produced by 30M SE read Illumina TruSeq profiling of RNA purified from treated cells as well as from cells treated with control media (DMSO). This ensured that the highest compound concentration can be tested that would not induce cell death processes and would thus faithfully recapitulate the compound mechanism of action (MoA) rather than the mechanisms and programs associated with cell demise. While in vivo endpoint phenotypes (e.g., tumor viability) are not effectively recapitulated in 2D cultures in vitro, compound MoA is reasonably well-recapitulated in both contexts. One aim can be to identify compounds capable of inverting MR activity signature in vitro in a relatively faithful model of the tumor regulatory context, to assess whether these compounds would have activity in vivo.

Drug signatures were analyzed with VIPER to assess the change in protein activity before and after the perturbation. Specifically, RX-GES were generated by differential expression of compound-treated vs. control-vehicle-treated cells at all time points and concentrations and analyzed with VIPER against the EP-NET interactome. This ranked all 5,602 regulatory proteins represented in the interactome from the one whose activity was most inhibited to the one whose activity was most increased following drug perturbation. An aREA analysis of patient samples that were well represented by the H-STS xenograft model was performed to assess enrichment of metastatic progression MRs in proteins whose activity was most inverted following drug perturbation. Since validation of these predictions was performed in H-STS mouse xenograft models, the analysis was limited to each NET-MET MRs that were recapitulated in the H-STS xenograft. This does not compromise the generality of the methodology. Rather they allow optimal tuning of the results to available in vitro and in vivo models for optimal design of validation assays. Thus, the OncoTreat methodology uses the ability to prioritize small molecule compounds that optimally reverse a patient-specific MR activity signature.

Figure 10A:
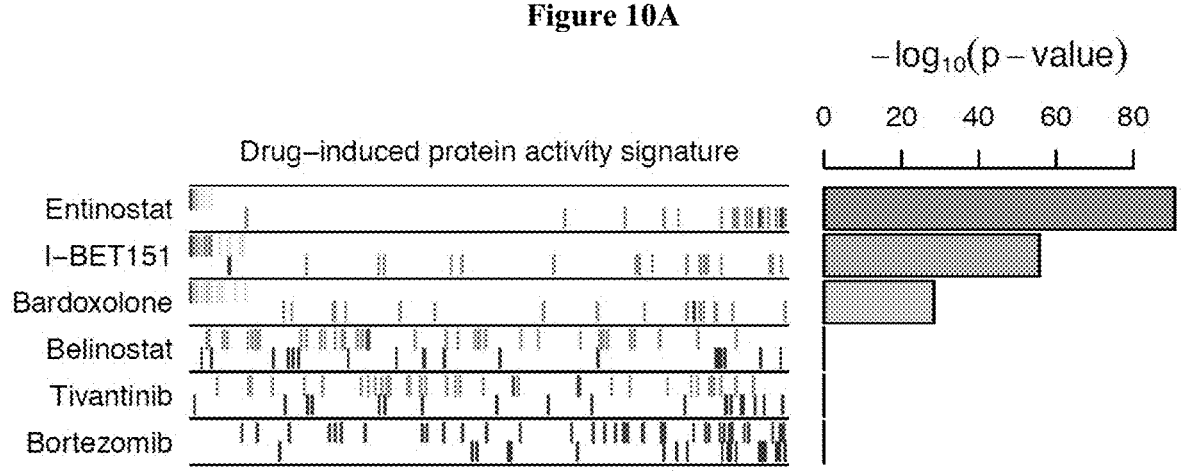
FIGS. 10A-10E depict small molecule compounds reverting the metastasis regulatory check-point. (A) Enrichment of patient-0 metastasis checkpoint MRs on the protein activity signatures induced by 6 selected compounds in the H-STS cells. (B and C) Growth curves for the H-STS xenograft while treated by vehicle control, and each of the 6 selected compounds. (D) Enrichment of patient-0 metastasis checkpoint on the protein activity signatures induced by 4 selected compounds in the H-STS xenograft. (E) Enrichment of H-STS xenograft checkpoint on the protein activity signatures induced by 4 selected compounds in the H-STS xenograft.
Figure 10B:
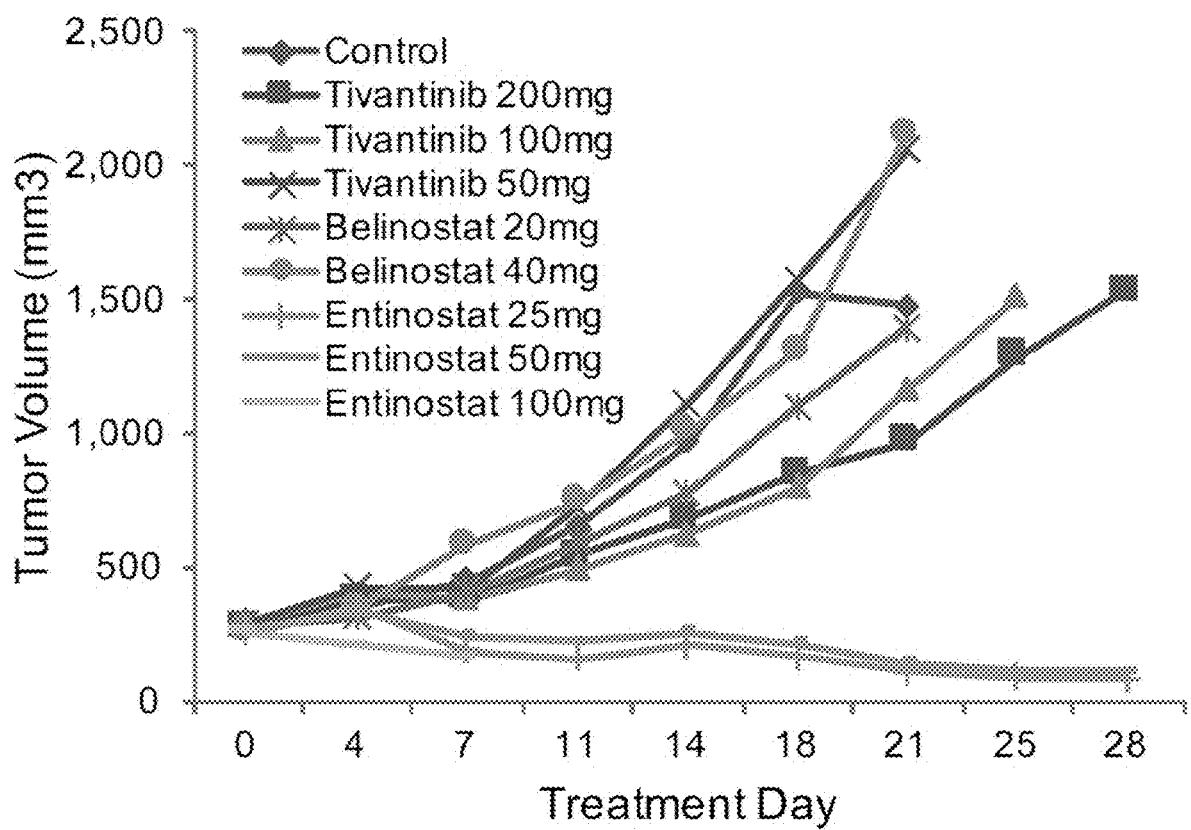
Figure 10C:
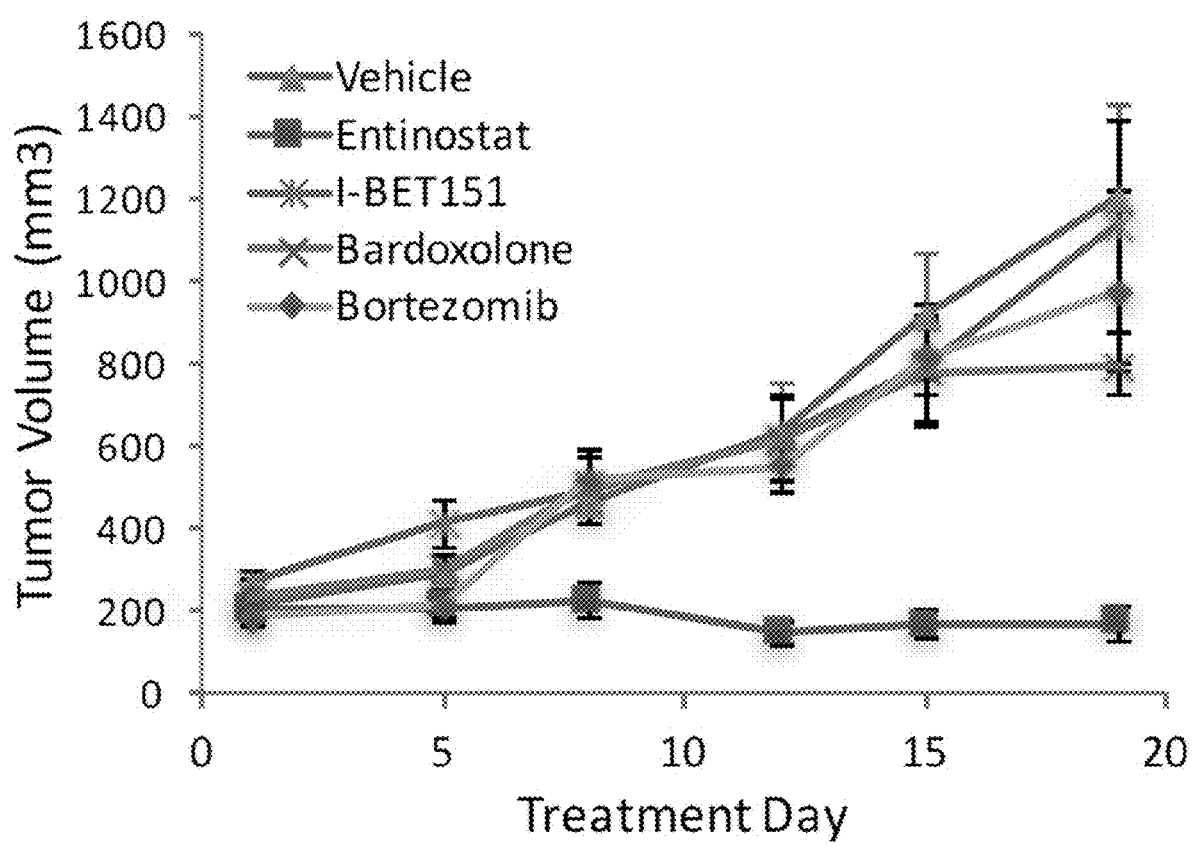
Figure 15:
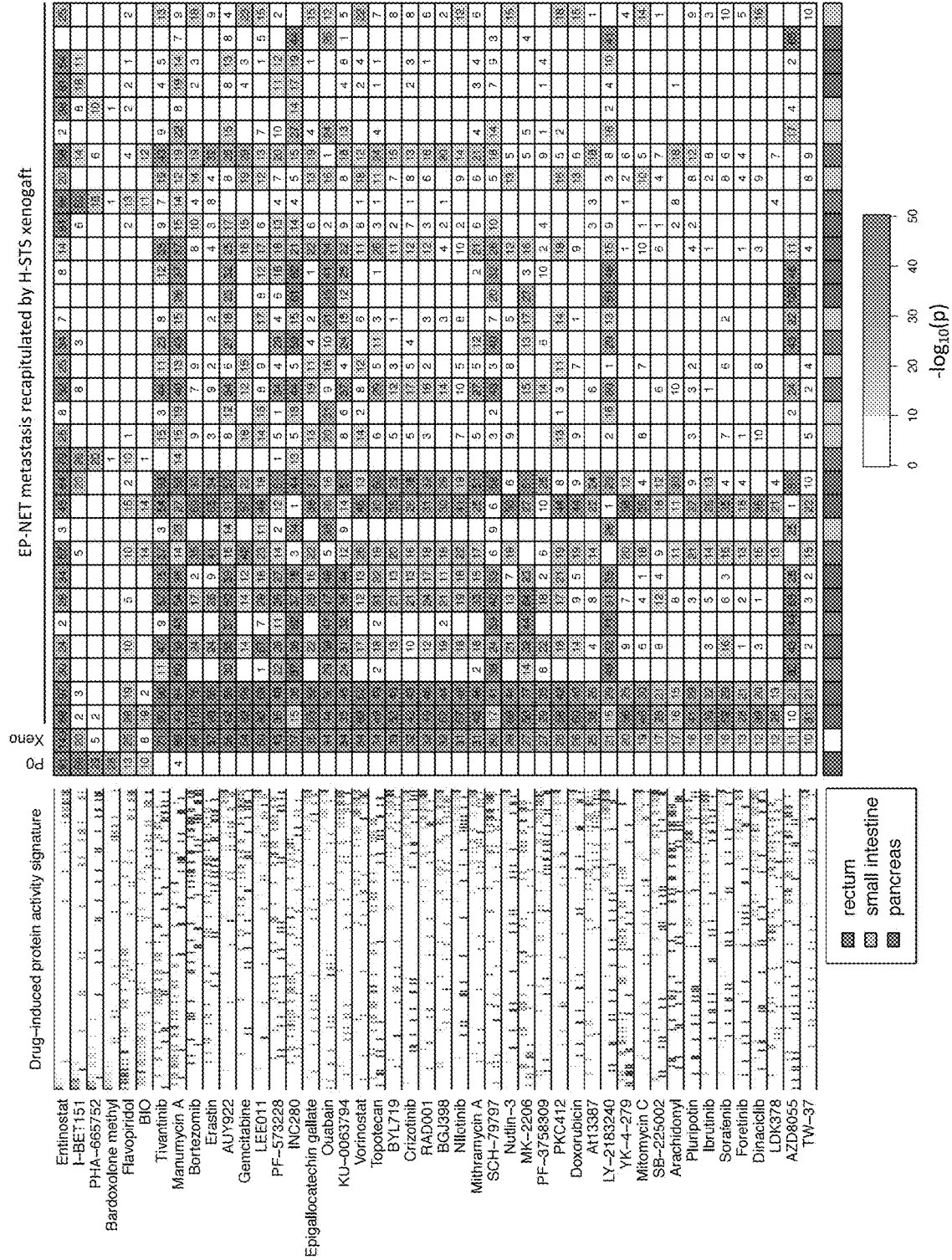
FIG. 15 depicts results of oncoTreat analysis. The heatmap shows the enrichment of the conserved MRs of each tumor and the H-STS xenograft model on the protein activity signature elicited by each drug perturbation on the H-STS cells. Enrichment strength is shown as $-\log_{10}$ (p-value) and indicated by the numbers. Only metastasis showing a significant similarity, at the MR level to the H-STS xenograft model were included in this analysis. The enrichment plot to the left shows the enrichment of the patient-0 MRs recapitulated by the xenograft model, on each drug perturbation protein activity signature.

Three drugs were identified that significantly reverted the selected patient (P0, see FIG. 6A) and H-STS xenograft specific MET-MR activity (Bonferroni's adjusted $p<10^{-10}$), including the HDAC⅓ inhibitor (entinostat), the protein bromodomain inhibitor (I-BET151), and the NF-κB inhibitor (bardoxolone methyl). Among them, entinostat showed the most significant reversal in both, the patient 0 MET-MR program recapitulated by the H-STS xenograft model, and the MRs of the xenograft model (FIGS. 10A-10C). FIG. 15 shows the oncoTreat (or oncoMatch) results for 46 selected compounds on patient 0, H-STS xenograft, and 31 additional tumors whose MRs were shown to be recapitulated by the H-STS xenograft model (see FIG. 9A). FIG. 15 depicts the enrichment of the top 50 most activated (shown in red in the enrichment plots) and the top 50 most deactivated (shown in blue) proteins in patient 0 on the protein activity signature induced by each compound perturbation in the H-STS cell line. The heatmap shows the statistical significance for MR reversal, expressed as $-\log_{10}$ (p-value), as quantified by the aREA technique by measuring the enrichment of each of 32 tumor samples and one xenograft sample MRs on the protein activity signature elicited by compound perturbation of H-STS cells. The colored bar indicates the tissue of origin for each of the evaluated tumors.

Drug Validation In Vivo:

H-STS cells effectively engraft in nude mice and RNASeq of resulting xenograft tumors showed remarkable overlap with patient-derived MRs (FIGS. 9A and 9D). Six compounds were selected for in vivo validation (FIG. 10A), including two compounds significantly abrogating the activity of patient-0 and xenograft MRs: Entinostat (the top prioritized compound), and I-BET151, a bromodomain inhibitor; one compound reverting the patient-0 MRs but not the xenograft MRs: Bardoxolone methyl, an oxidative stress activator/NFκB inhibitor; one compound reverting the xenograft but not patient-0 MRs: Tivantinib, a c-Met inhibitor with complementary activity as a microtubule inhibitor; and one compound showing no significant reversal of either patient-0 or xenograft MRs: PDX101 (Belinostat), a pan-HDAC inhibitor. The latter compound was selected among the ones showing no activity because, from a pharmacological perspective, it should have effects similar to entinostat and yet the two compounds were predicted to be at the opposite end of the MR-signature reversal activity.

In vivo validation in NOD-SCIDS mice xenografts established by subcutaneous injection of H-STS cells was first conducted at Champions Oncology and then independently confirmed in the mouse hospital facility at Columbia University. Mice were enrolled in treatment arms when tumor size reached 250 mm³ and were treated for 25 days. Tumor size was measured twice weekly by digital caliper, see methods. While mild tumor growth inhibition (TGI) was seen with high levels of Tivantinib (43% TGI at 200 mg/kg/dose and 28% TGI at 100 mg/kg/dose), the tumor still progressed, albeit at a slower rate than the controls. Tumors treated with Belinostat showed minimal TGI, with only an 8% TGI at the 20 mg/kg/dose level. In stark contrast, treatment with Entinostat showed high levels of tumor regression (TR), with 68% TR and 112% TGI at 25 mg/kg/dose and 58% TR and 110% TGI at 50 mg/kg/dose. Treatment with Entinostat was toxic at 100 mg/kg/dose, however the single surviving animal from that group showed tumor regression of 49%. These results are summarized in Table 3 and FIG. 10B.

TABLE 3

Tumor Volume and Agent Activity Data

| Group | % TGI | RECIST PD/SD/PR/CR* | % TR |
|---|---|---|---|
| Control | | 3/0/0/0 | n/a |
| ARQ197 200 mg | 43% | 3/0/0/0 | n/a |
| ARQ197 100 mg | 28% | 3/0/0/0 | n/a |
| ARQ197 50 mg | −46% | 3/0/0/0 | n/a |
| PDX101 20 mg | 8% | 3/0/0/0 | n/a |
| PDX101 40 mg | −55% | 3/0/0/0 | n/a |
| MS-27-275 25 mg | 112% | 0/0/3/0 | 68 |
| MS-27-275 50 mg | 110% | 0/0/3/0 | 58 |
| MS-27-275 100 mg** | n/a | 0/0/1/0 | 49 |

Figure 10D:
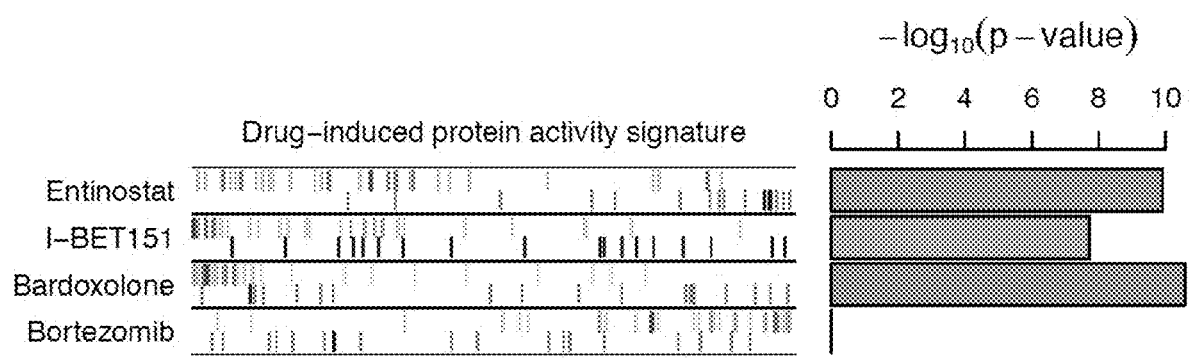

*PD-Progressive Disease; SD-Stable Disease; PR-Partial Response; CR-Complete Response
**Four of five animals died one week into the test, likely as a result of drug toxicity; results are representative of the single surviving animal Follow-up studies at Columbia confirmed the original observation for Entinostat, with complete tumor growth abrogation (FIG. 10C). A weak reduction in tumor growth for Bardoxolone methyl was observed only for the last two time points evaluated, and no significant difference when compared to vehicle control for I-BET151 and Bortezomib (FIG. 10C). In agreement with compound perturbation effect in vitro (FIG. 10A), analysis of xenograft transcriptome 3 hours after $3^{rd}$ drug administration indicated a strong inhibition of patient-0 checkpoint protein activity by Entinostat, I-BET151 and Bardoxolone methyl, and no effect of Bortezomib (FIG. 10D). Similarly, the same analysis showed a significant inhibition of the H-STS xenograft checkpoint only by Entinostat. This is in line with the poor effect of Bardoxolone methyl, I-BET151 and Bortezomib on xenograft tumor growth, and the strong abrogation elicited by Entinostat (FIGS. 10B and 10C). In summary, while the effect of the Entinostat, I-BET151 and Bardoxolone methyl on the reversal of patient-0 checkpoint activity inferred from the in vitro H-STS perturbation assay was confirmed in the xenograft model, only Entinostat reverted the activity of the H-STS xenograft checkpoints and abrogated tumor growth (FIG. 10).

Figure 10E:
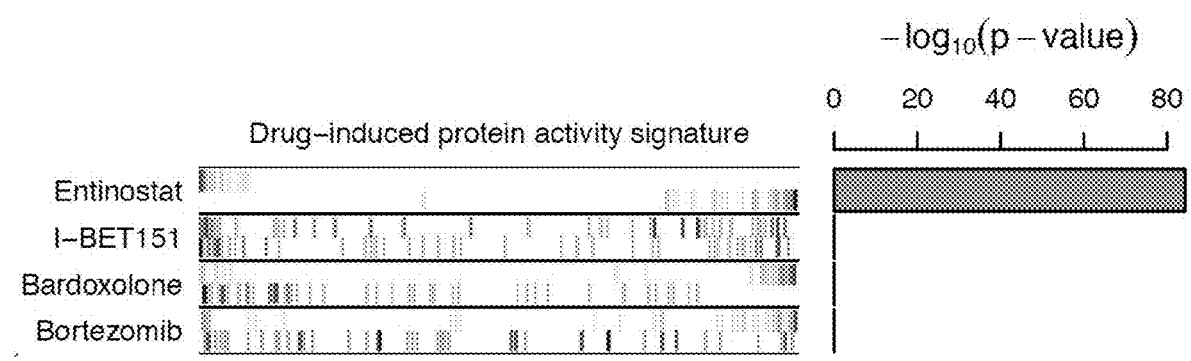

FIG. 10A depicts enrichment of patient-0 metastasis checkpoint MRs on the protein activity signatures induced by 6 selected compounds in the H-STS cells. FIGS. 10B and 10C depict growth curves for the H-STS xenograft while treated by vehicle control, and each of the 6 selected compounds. Curves show tumor volume for individual animals (FIG. 10B) or the mean±SEM of 8 animals (FIG. 10C). FIG. 10D depicts enrichment of patient-0 metastasis checkpoint on the protein activity signatures induced by 4 selected compounds in the H-STS xenograft. FIG. 10E depicts enrichment of H-STS xenograft checkpoint on the protein activity signatures induced by 4 selected compounds in the H-STS xenograft.

Discussion

Despite success, the oncogene addiction paradigm[1] has shown increasing challenges including a diminishing number of novel, high-penetrance actionable targets identifiable by genetic alterations in tumor sequences, lack of actionable mutations in the majority of cancer patients, and high frequency of relapse following targeted therapy. Indeed, only 5% to 11% of patients experience progression free survival increase when treated with targeted inhibitors based on tumor genetics (Mardis personal communication).

Certain results have revealed the existence of a new class of proteins (master regulators) responsible for mechanistically implementing the transcriptional signature of a specific tumor. MR proteins can be efficiently identified by regulatory network based analysis, even on an individual patient basis[18], despite the fact that they are rarely mutated or differentially expressed. This example supports unbiased assessment of FDA approved drugs and investigational compounds in terms of their ability to reverse patient-specific MR activity signatures, using the OncoTreat analysis, is effective in prioritizing compounds that can abrogate tumor viability in vivo.

The OncoTreat methodology was tested in a rare tumor type (EP-NETs), which notoriously lack targetable alterations and are poorly characterized in the literature. This choice was deliberate to show that the proposed approach can be efficiently applied in unbiased fashion even to tumors for which little information is available at the molecular level. Indeed, the more complex component of the analyses presented in this example was the collection and profiling of a large number of EP-NET tumors from 17 collaborating centers to provide adequate data for assembling the regulatory model and for interrogating it with signatures of metastatic progression. The OncoTreat methodology was however, completely generalizable and is tested in a much broader study that covers 14 rare and otherwise untreatable malignancies.

Validation assays confirmed that drugs predicted to have high, medium, and no activity on MR-signature reversal produced tumor regression, tumor growth reduction, and no effect, respectively, thus substantially validating the approach. Remarkably, all of these compounds had been prioritized based on their high differential toxicity in EP-NET cell lines, thus confirming that in vitro toxicity is not a good predictor of in vivo activity, even when the same cell line is used in both assays. It is also important to note the top drugs prioritized by VIPER-based perturbational profile analysis induced profound reversal of virtually all top 50 master regulator proteins (i.e. of the entire tumor checkpoint module). Since it is unlikely that these compounds can represent specific inhibitors and activators of such large and unique protein sets, this support that tumor checkpoints represent tightly auto-regulated modules that can be switched globally off by pharmacological intervention. This had been previously reported, for instance by RNAi mediated silencing of synergistic MR-pairs in glioma[9] and prostate cancer[10], which caused collapse of the entire MR module. Thus, these analyses presented in this Example further confirm the critical role of tumor checkpoint modules as regulatory switches responsible for maintaining the stability of tumor state.

Since the OncoTreat methodology prioritizes compound activity based on patient-specific MR signatures, prioritized drugs are naturally coupled with MR-based biomarkers for the selection of responders vs. non responder cohorts. Interestingly, as shown for EP-NET tumors, patients clustered within a handful of subtypes, each presenting a virtually identical MR activity profile. This support a potential for more universal therapies, despite tumor heterogeneity at the genetic level. As a result, the OncoTreat methodology can be suited to the efficient generation of basket study designs, where patients can be assigned to different treatment arms depending on their specific MR signature.

If a patient that responded to targeted therapy effectively clusters within a relatively small number of distinct MR signatures, this supports that once a sufficient number of PDX model have been tested for each subtype, treatment for additional patients can be determined on the basis of previous response in PDX models that represent a close match for the patient MR activity signature. Additionally, the ability to screen compound in vitro can lead to assessing effective compound activity in reversing MR activity signatures but at concentrations that are not physiologically achievable. This can be addressed for instance by studying compound PD in vivo at maximum tolerated doses, by analyzing the gene expression patterns of the top prioritized compounds following in vivo perturbation of tumor xenografts. This would also address potential issues related to differential compound activity in vitro and in vivo, even though compound mechanism of action, as opposed to phenotypic endpoint, is relatively well-conserved in these contexts.

CONCLUSION

As shown in this Example, the OncoTreat or OncoMatch methodology is a highly innovative and broadly applicable RNA-based approach to precision cancer medicine. It provides a comprehensive and experimentally validated framework for prioritizing therapeutic strategies on an individual patient basis. Specifically, therapeutic strategies are prioritized by simultaneously identifying critical tumor dependencies and the drugs that are optimally suited to abrogate their activity, via context specific regulatory network analysis. This methodology has been tested in a rare tumor context—enteropancreatic neuroendocrine tumors—with full in vivo validation of therapeutic strategies.

LIST OF REFERENCES

1 Weinstein, I. B. Cancer. Addiction to oncogenes—the Achilles heal of cancer. *Science* 297, 63-64 (2002).
2 Commo, F. et al. Impact of centralization on aCGH-based genomic profiles for precision medicine in oncology. *Ann Oncol* 26, 582-588 (2015).
3 MacConaill, L. E. et al. Prospective Enterprise-Level Molecular Genotyping of a Cohort of Cancer Patients. *The Journal of molecular diagnostics: JMD* (2014); 16(6):660-72.
4 Jang, S. & Atkins, M. Which drug, and when, for patients with BRAF-mutant melanoma? *Lancet Oncol.* 14(2), e60-69 (2013).
5 Davoli, A., Hocevar, B. A. & Brown, T. L. Progression and treatment of HER2-positive breast cancer. *Cancer Chemother Pharmacol* 65, 611-623 (2010).
6 Basu, A. et al. An interactive resource to identify cancer genetic and lineage dependencies targeted by small molecules. *Cell* 154, 1151-1161 (2013).
7 Compagno, M. et al. Mutations of multiple genes cause deregulation of NF-kappaB in diffuse large B-cell lymphoma. *Nature* 459, 717-721 (2009).
8 Bisikirska, B. et al. Elucidation and Pharmacological Targeting of Novel Molecular Drivers of Follicular Lymphoma Progression. *Cancer Res* (2016); 76(3):664-74).
9 Carro, M. S. et al. The transcriptional network for mesenchymal transformation of brain tumours. *Nature* 463, 318-325 (2010).
10 Aytes, A. et al. Cross-species regulatory network analysis identifies a synergistic interaction between FOXM1 and CENPF that drives prostate cancer malignancy. *Cancer Cell* 25, 638-651 (2014).
11 Mitrofanova, A., Aytes, A., Shen, C., Abate-Shen, C. & Califano, A. A systems biology approach to predict drug response for human prostate cancer based on in vivo preclinical analyses of mouse models. *Cell Reports* 12, 1-12 (2015).
12 Rodriguez-Barrueco, R. et al. Inhibition of the autocrine IL-6-JAK2-STAT3-calprotectin axis as targeted therapy for HR−/HER2+ breast cancers. *Genes Dev* 29, 1631-1648 (2015).
13 Piovan, E. et al. Direct reversal of glucocorticoid resistance by AKT inhibition in acute lymphoblastic leukemia. *Cancer Cell* 24, 766-776 (2013).
14 Chen, J. C. et al. Identification of Causal Genetic Drivers of Human Disease through Systems-Level Analysis of Regulatory Networks. *Cell* 159, 402-414 (2014).
15 Luo, J., Solimini, N. L. & Elledge, S. J. Principles of cancer therapy: oncogene and non-oncogene addiction. *Cell* 136, 823-837 (2009).
16 Schreiber, S. L. et al. Towards patient-based cancer therapeutics. *Nat Biotechnol* 28, 904-906 (2010).
17 Lefebvre, C. et al. A human B-cell interactome identifies MYB and FOXM1 as master regulators of proliferation in germinal centers. *Mol Syst Biol* 6, 377 (2010).
18 Alvarez, M. J. et al. Functional characterization of somatic mutations in cancer using network-based inference of protein activity. *Nat Genet* (2016); 48(8): 838: 847.
19 Basso, K. et al. Reverse engineering of regulatory networks in human B cells. *Nat Genet* 37, 382-390 (2005).
20 Margolin, A. A. et al. ARACNE: an algorithm for the reconstruction of gene regulatory networks in a mammalian cellular context. *BMC bioinformatics* 7 Suppl 1, S7 (2006).
21 Basso, K. et al. Integrated biochemical and computational approach identifies BCL6 direct target genes controlling multiple pathways in normal germinal center B cells. *Blood* 115, 975-984 (2010).
22 Pfragner, R. et al. Establishment and characterization of three novel cell lines—P-STS, L-STS, H-STS—derived from a human metastatic midgut carcinoid. *Anticancer Res* 29, 1951-1961 (2009).
23 Pfragner, R. et al. Establishment of a continuous cell line from a human carcinoid of the small intestine (KRJ-I). *International journal of oncology* 8, 513-520 (1996).

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the compositions and methods of the disclosed subject matter without departing from the spirit or scope of the disclosed subject matter. Thus, it is intended that the disclosed subject matter include modifications and variations that are within the scope of the appended claims and their equivalents.

All patents and publications in this specification are herein incorporated by reference to the same extent as if each independent patent and publication and sequence was specifically and individually indicated to be incorporated by reference.

What is claimed is:

1. A processing method using a processor foref screening for a therapeutic compound or agent based on an individual subject's sample, comprising:
   identifying a cell or tissue sample from a subject having a disease or disorder;
   identifying a library comprising a plurality of possible therapeutic compounds or agents;
   quantifying a protein activity of each of a plurality of master regulator proteins (MRPs) in the subject's cell or tissue sample to provide a subject sample-specific MRP activity signature comprising a plurality of activated and/or deactivated MRPs characteristic of the disease or disorder, wherein quantifying the protein activity of each MRP comprises measuring the expression level of a plurality of transcriptional targets (regulons) for each MRP, and computationally inferring, using a algorithm processing arrangement, each MRP activity based, at least in part, on the measured regulon expression levels in the context of a tissue-specific regulatory model;
   comparing, for each of the plurality of possible therapeutic compounds or agents; the subject sample-specific MRP activity signature to each of a corresponding plurality of quantified compound-perturbed or agent-perturbed MRP activity signatures of a cell line or of an in vitro model that reflects, prior to perturbation in each case, the subject sample-specific MRP activity signature;
   computing, using the algorithm processing arrangement, for each of the plurality of possible therapeutic compounds or agents; a statistical enrichment of the activated MRPs among the MRPs most deactivated by the compound or agent; and/or a statistical enrichment of the inactivated MRPs among the MRPs most induced by the compound or agent;
   determining, using the algorithm processing arrangement, a subject sample-specific ranking of the compounds or agents according to the degree of enrichment, wherein the compounds or the agents inducing the greatest enrichment are deemed as having the highest therapeutic value for the subject; and
   identifying, among the plurality of possible therapeutic compounds or agents, a therapeutic compound or agent for treating the subject's disease or disorder based on the subject sample and the subject sample-specific ranking validating the efficacy of a ranked drug using an in vivo model.

2. The method of claim 1, wherein, with respect to the subject sample-specific MRP activity signature, the compound or agent induces global inversion of the protein activities of the activated MRPs among the MRPs most inactivated by the compound or agent, and/or of the inactivated MRPs among the MRPs most induced by the compound or agent.

3. The method of claim 1, wherein the compound or agent is selected from the group consisting of small molecule chemical compounds, peptides, nucleic acids, oligonucleotides, antibodies, aptatners, modifications thereof, and combinations thereof.

4. The method of claim 1, wherein thy: disease or disorder is a tumor.

5. The method of claim 4, wherein the tumor is selected from the group consisting of glioblastoma, meningioma, leukemia, lymphoma, sarcoma, carcinoid, neuroendocrine, paraganglioma, melanoma, prostate, pancreatic, bladder, stomach, colon, breast, head & neck, kidney, gastric, small intestine, ovarian, hepatocellular, uterine corpus, and lung carcinoma.

6. The method of claim 1, wherein computationally inferring the protein activity of each MRP, comparing the subject sample-specific MRP activity signature to each of the plurality of quantified compound-perturbed or agent-perturbed MRP activity signatures, and computing, for each compound or agent, the statistical enrichment of the activated MRPs and/or the statistical enrichment of the inactivated MRPs, comprises use of virtual inference of protein activity by enriched regulon analysis (VIPER).

7. The method of claim 1, wherein said sample from said disease or disorder is derived from an in vivo source, and/or derived from an in vitro source.

8. The method of claim 7, wherein said in vitro source is an in vitro model of the disease or disorder that has a similar master regulator signature profile for said disease or disorder.

9. The method of claim 7, wherein said sample is selected from the group consisting of tissue extracts, cells, tissues, organs, blood, blood serum, body fluids and combinations thereof.

10. The method of claim 7, wherein said sample from said disease or disorder is at least one selected from the group consisting of a cell line, cultured cells, cultured tissue and cultured tumor.

11. The method of claim 1, wherein said regulons are inferred by ARACNe.

12. The method of claim 1, wherein the in vivo model comprises a xenograft model.

* * * * *